US010501691B2

(12) United States Patent
Goetz et al.

(10) Patent No.: US 10,501,691 B2
(45) Date of Patent: Dec. 10, 2019

(54) PIPERIDINE DERIVATIVES AND LIQUID-CRYSTALLINE MEDIUM

(71) Applicant: MERCK PATENT GMBH, Darmstadt (DE)

(72) Inventors: Achim Goetz, Alsbach-Haehnlein (DE); Rocco Fortte, Frankfurt am Main (DE); Martin Engel, Darmstadt (DE); Sabrina Maag, Pfungstadt (DE); Thorsten Kodek, Walldorf (DE)

(73) Assignee: MERCK PATENT GMBH, Darmstadt (DE)

( * ) Notice: Subject to any disclaimer, the term of this patent is extended or adjusted under 35 U.S.C. 154(b) by 98 days.

(21) Appl. No.: 15/668,962

(22) Filed: Aug. 4, 2017

(65) Prior Publication Data

US 2018/0037820 A1 Feb. 8, 2018

(30) Foreign Application Priority Data

Aug. 5, 2016 (DE) .................. 10 2016 009 485

(51) Int. Cl.
| | |
|---|---|
| *G02F 1/1333* | (2006.01) |
| *C09K 19/54* | (2006.01) |
| *C07D 211/46* | (2006.01) |
| *C09K 19/30* | (2006.01) |
| *C09K 19/34* | (2006.01) |

(52) U.S. Cl.
CPC .......... *C09K 19/54* (2013.01); *C07D 211/46* (2013.01); *C09K 19/3098* (2013.01); *C09K 19/3402* (2013.01); *C09K 2019/3422* (2013.01)

(58) Field of Classification Search
CPC ............... C09K 19/54; C09K 19/3402; C09K 2019/3422; G02F 1/1333; C07D 211/46

USPC ........................................................ 252/299.5
See application file for complete search history.

(56) References Cited

U.S. PATENT DOCUMENTS

| | | | |
|---|---|---|---|
| 9,631,142 B2 * | 4/2017 | Gotoh | ............... C09K 19/3458 |
| 9,643,924 B2 | 5/2017 | Gotoh et al. | |
| 10,053,425 B2 * | 8/2018 | Gotoh | ............... C09K 19/3483 |
| 2011/0101270 A1 | 5/2011 | Manabe | |
| 2016/0039758 A1 | 2/2016 | Gotoh et al. | |
| 2016/0376505 A1 | 12/2016 | Furusato et al. | |

FOREIGN PATENT DOCUMENTS

| | | |
|---|---|---|
| DE | 102015013980 A1 | 5/2016 |
| EP | 2982731 A1 | 2/2016 |
| WO | 2002018515 A1 | 3/2002 |
| WO | 2009129911 A1 | 10/2009 |
| WO | 2015079797 A1 | 6/2015 |
| WO | 2016111027 A1 | 7/2016 |

OTHER PUBLICATIONS

European Search Report for EP-17184411 dated Oct. 24, 2017.
English Abstract Provided for DE-102015013980, Publication Date: May 12, 2016.
English Abstract Provided for WO-2016111027, Publication Date: Jul. 14, 2016.

\* cited by examiner

*Primary Examiner* — Geraldina Visconti
(74) *Attorney, Agent, or Firm* — Millen White Zelano and Branigan, PC; Csaba Henter

(57) ABSTRACT

Disclosed are compounds of the formula I, liquid-crystalline media comprising the compounds of formula I, and the use of these liquid-crystalline media in liquid-crystal displays.

19 Claims, No Drawings

PIPERIDINE DERIVATIVES AND LIQUID-CRYSTALLINE MEDIUM

The present invention relates to compounds of the formula I defined below, to liquid-crystalline media comprising the compounds of the formula I, and to the use of these liquid-crystalline media in liquid-crystal displays.

The principle of electrically controlled birefringence, the ECB effect or else DAP effect (Deformation of Aligned Phases), was first described in 1971 (M. F. Schieckel and K. Fahrenschon, "Deformation of nematic liquid crystals with vertical orientation in electrical fields", Appl. Phys. Lett. 19 (1971), 3912). This was followed by studies by J. F. Kahn (Appl. Phys. Lett. 20 (1972), 1193) and G. Labrunie and J. Robert (J. Appl. Phys. 44 (1973), 4869).

The studies by J. Robert and F. Clerc (SID 80 Digest Techn. Papers (1980), 30), J. Duchene (Displays 7 (1986), 3) and H. Schad (SID 82 Digest Techn. Papers (1982), 244) showed that liquid-crystalline phases must have high values for the ratio of the elastic constants $K_3/K_1$, high values for optical anisotropy $\Delta n$ and values of dielectric anisotropy $\Delta\varepsilon \leq -0.5$ in order to be usable for highly informative display elements based on the ECB effect. Electrooptical display elements based on the ECB effect have homeotropic edge orientation (VA methodology=Vertical Aligned).

It is also possible to use dielectrically negative liquid-crystal media in displays that use what is called the IPS (In-Plane Switching) effect (S. H. Lee, S. L. Lee, H. Y. Kim, Appl. Phys. Lett. 1998, 73(20), 2881-2883). The same also applies to displays that use what is called the FFS (Fringe Field Switching) effect.

The technical employment of these effects in electrooptical display elements requires liquid-crystalline phases (LC phases) that have to meet a multitude of requirements. Of particular importance here are chemical stability to moisture, air and physical effects such as heat, radiation in the infrared, visible and ultraviolet region, and electrical DC and AC fields.

Moreover, technically usable LC phases are expected to have a liquid-crystalline mesophase within a suitable temperature range and a low viscosity.

Within the series of compounds having a liquid-crystalline mesophase that are known to date, there is no single compound that meets all these requirements. Therefore, mixtures of compounds are generally provided in order to obtain materials usable as LC phases.

Matrix liquid-crystal displays (MLC displays) are known. Non-linear elements used for individual switching of the individual pixels may, for example, be active elements (i.e. transistors). In that case, reference is made to an "active matrix", generally with use of thin-film transistors (TFTs) that are generally disposed on a glass plate as substrate.

A distinction is made between two technologies, namely between TFTs composed of compound semiconductors, for example CdSe, and TFTs based on polycrystalline and, inter alia, amorphous silicon. The latter technology currently has the greatest commercial significance on a global scale.

The TFT matrix has been applied to the inside of one glass plate of the display, while the other glass plate optionally bears the transparent counterelectrode on its inside. Compared to the size of the pixel electrode, the TFT is very small and effectively does not disrupt the image. This technology can also be extended for full colour-capable image displays, wherein a mosaic of red, green and blue filters is arranged such that one filter element is opposite each switchable image element.

The most commonly used TFT displays to date typically work with crossed polarizers in transmission and are backlit. IPS cells or ECB (or VAN) cells are used for TV applications, whereas usually IPS cells or TN (Twisted Nematic) cells are used for monitors, and usually TN cells are used for notebooks, laptops and for mobile applications.

The term "MLC displays" encompasses matrix displays having integrated non-linear elements, i.e. having not only the active matrix but also displays with passive elements such as varistors or diodes (MIM=Metal-Insulator-Metal).

MLC displays are especially suitable for TV applications, monitors and notebooks, or for displays with high information density, for example in automobile and aircraft construction. As well as problems with regard to the angle dependence of contrast and the switching times, difficulties arise in the case of MLC displays that are caused by insufficiently high specific resistivity of liquid-crystal mixtures; see, for example, S. Togashi, K. Sekiguchi, H. Tanabe, E. Yamamoto, K. Sorimachi, E. Tajima, H. Watanabe, H. Shimizu, Proc. Eurodisplay 84, September 1984: A 210-288 Matrix LCD Controlled by Double Stage Diode Rings, p. 141 ff., Paris; M. Stromer, Proc. Eurodisplay 84, September 1984: Design of Thin Film Transistors for Matrix Addressing of Television Liquid Crystal Displays, p. 145 ff., Paris. With decreasing resistivity, there is a deterioration in the contrast of an MLC display. Since the specific resistivity of the liquid-crystal mixture generally decreases through interaction with the inner surfaces of the display over the lifetime of an MLC display, a high (initial) resistivity is important for displays that have to have acceptable resistivity values over a long service life.

Displays that use the ECB effect have become established as what are called VAN (Vertically Aligned Nematic) displays alongside IPS displays (e.g. S. D. Yeo, Presentation 15.3: "A LC Display for the TV Application", SID 2004 International Symposium, Digest of Technical Papers, XXXV, Book II, p. 758 and 759) and the TN displays that have long been known as one of the three currently most important newer types of liquid-crystal displays particularly for television applications.

The most important designs here include: MVA (Multi-Domain Vertical Alignment, e.g.: H. Yoshide et al., Presentation 3.1: "MVA LCD for Notebook or Mobile PCs . . . ", SID 2004 International Symposium, Digest of Technical Papers, XXXV, Book I, p. 6 to 9 and C. T. Liu et al., Presentation 15.1: "A 46-inch TFT-LCD HDTV Technology . . . ", SID 2004 International Symposium, Digest of Technical Papers, XXXV, Book II, p. 750 to 753), PVA (Patterned Vertical Alignment, e.g.: Kim, Sang Soo, Presentation 15.4: "Super PVA Sets New State-of-the-Art for LCD-TV", SID 2004 International Symposium, Digest of Technical Papers, XXXV, Book II, p. 760 to 763) and ASV (Advanced Super View, e.g.: Shigeta, Mitzuhiro and Fukuoka, Hirofumi, Presentation 15.2: "Development of High Quality LCDTV", SID 2004 International Symposium, Digest of Technical Papers, XXXV, Book II, p. 754 to 757).

In general form, the technologies are compared, for example, in Souk, Jun, SID Seminar 2004, Seminar M-6: "Recent Advances in LCD Technology", Seminar Lecture Notes, M-6/1 to M-6/26 and Miller, Ian, SID Seminar 2004, Seminar M-7: "LCD-Television", Seminar Lecture Notes, M-7/1 to M-7/32. Even though the switching times of modern ECB displays have already been distinctly improved by drive methods with overdrive (e.g. Kim, Hyeon Kyeong et al., Presentation 9.1: "A 57-in. Broad UXGA TFT-LCD for HDTV Application", SID 2004 International Symposium, Digest of Technical Papers, XXXV, Book I, p. 106 to 109), the achievement of video-capable switching times, especially in the switching of grey stages, is a problem that has not yet been solved satisfactorily.

Like ASV displays, ECB displays use liquid-crystalline media with negative dielectric anisotropy ($\Delta\varepsilon$), whereas TN displays and all IPS displays in common use to date use liquid-crystalline media with positive dielectric anisotropy. However, it is alternatively also possible to use dielectrically negative liquid-crystalline media in displays based on the IPS or FFS effect. In liquid-crystal displays of this kind, the liquid crystals are used as dielectrics, the optical properties of which change reversibly on application of an electrical voltage.

Since the operating voltage should generally be at a minimum in displays, i.e. including displays according to these mentioned effects, liquid-crystalline media that are generally composed predominantly of liquid-crystal compounds that all have the same sign of dielectric anisotropy and have a maximum magnitude of dielectric anisotropy are used. In general, relatively small proportions at most of neutral compounds and if at all possible no compounds having an opposite sign of dielectric anisotropy to that of the medium are used. In the case of liquid-crystalline media with negative dielectric anisotropy for ECB displays, for example, predominantly compounds having negative dielectric anisotropy are thus used. The liquid-crystalline media used generally consist predominantly and usually actually very substantially of liquid-crystal compounds having negative dielectric anisotropy.

For many practical applications in liquid-crystal displays, however, the known liquid-crystalline media do not have sufficient stability. Particularly the stability thereof to irradiation by UV, but also even by the standard backlighting, leads to a deterioration in the electrical properties in particular. For example, there is a significant increase in conductivity.

For stabilization of liquid-crystal mixtures, the use of sterically hindered amines, called "hindered amine light stabilizers", HALS for short, has already been proposed.

Nematic liquid-crystal mixtures having negative dielectric anisotropy that contain a small amount of TINUVIN®770, a compound of the formula as stabilizer are described, for example, in WO 2009/129911 A1. However, the corresponding liquid-crystal mixtures do not have adequate properties for some practical applications. Among other factors, they can sometimes not be stable enough to stress resulting from irradiation with typical CCFL (Cold Cathode Fluorescent Lamp) backlighting and/or have problems with regard to low-temperature stability.

Similar liquid-crystal mixtures are also known, for example, from EP 2 182 046 A1, WO 2008/009417 A1, WO 2009/021671 A1 and WO 2009/115186 A1. These liquid-crystal mixtures, according to the description therein, may optionally also comprise stabilizers of various kinds, for example phenols and sterically hindered amines (HALS).

These liquid-crystal mixtures may, in a different degree according to the application, in some cases show a deterioration in one or more parameters of relevance in the operation of a liquid-crystal display. More particularly, there can be a drop in the voltage holding ratio (VHR for short) thereof after stress. Moreover, a yellowish discolouration can occur in the event of extreme stress.

Furthermore, the use of various stabilizers in liquid-crystalline media is described, for example, in JP (S)55-023169 (A), JP (H)05-117324 (A), WO 02/18515 A1 and JP (H) 09-291282 (A).

TINUVIN® 123, a compound of the formula

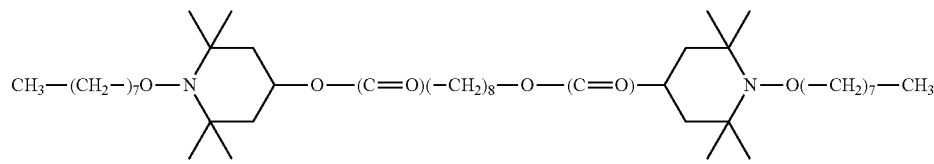

has also been suggested for stabilization purposes.

HALS with various substituents on the nitrogen atom are compared with regard to their $pK_B$ values in Ohkatsu, Y., J. of Japan Petroleum Institute, 51 (2008), p. 191-204. The following types of structural formulae are described here:

| Type | Active group of the stabilizer |
|---|---|
| "HALS" | RO—⟨piperidine⟩N—H |
| "R-HALS" or "NR-HALS" | RO—⟨piperidine⟩N—R |
| "NOR-HALS" | RO—⟨piperidine⟩N—OR |

The compound TEMPOL, of the following formula

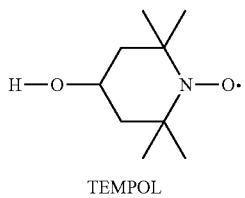

TEMPOL is known; it is mentioned, for example, in Miéville, P. et al., Angew. Chem., 122 (2010), p. 6318-6321. It is commercially available from various manufacturers and is used, for example, in formulations for precursors for polyolefins, polystyrenes, polyamides, coatings and PVC as polymerization inhibitor and, especially in combination with UV absorbers, as light or UV stabilizer.

Prior art liquid-crystal media with appropriately low drive voltages have relatively low electrical resistances or an as yet inadequate, i.e. excessively low, voltage holding ratio (VHR) and, in the displays, often lead to unwanted flicker and/or inadequate transmission. Moreover, they are not sufficiently stable to thermal and/or UV stress, at least when they have a correspondingly high polarity as necessary for low drive voltages.

On the other hand, the drive voltage of the prior art displays having a high VHR is often too high, especially for displays that do not have direct connection or through-connection to the power supply grid, for example displays for mobile applications.

Moreover, the phase region of the liquid-crystal mixture has to be sufficiently broad for envisaged display applications.

Furthermore, attention has to be paid to suitable switching times of the liquid-crystal media in the displays. This is particularly important for displays for television or multimedia applications. For improvement of the switching times, there have been repeated past proposals to optimize the rotational viscosity ($\gamma_1$) of liquid-crystal media, i.e. to implement media having a minimum rotational viscosity. However, the effects achieved are inadequate for many applications.

In addition, adequate stability of the media to extreme stresses, especially to UV and/or thermal stress, has to be assured, particularly in the case of applications in displays in mobile devices, for example mobile phones.

A disadvantage of MLC displays known to date is based on their comparatively low contrast, the relatively high viewing angle dependence and the difficulty in generating shades of grey in these displays, and also their inadequate VHR and their inadequate lifetime.

There is thus still a great need for MLC displays having very high specific resistivity coupled with a simultaneously wide working temperature range, short switching times and a low threshold voltage, with the aid of which it is possible to produce various shades of grey and which especially have a good and stable VHR.

The problem addressed by the invention is that of providing compounds which, in liquid-crystalline mixtures, contribute to advantageous properties in such a way that useful and improved MLC displays, especially those that are based on the ECB effect or on the IPS or FFS effect and also include mobile applications, become obtainable. A particular problem addressed is that of providing compounds and liquid-crystalline media and MLC displays comprising these media that have the above-specified disadvantages only to a lesser degree, if at all, and simultaneously have very high specific resistivities, and moreover also enable working, particularly for mobile systems, even at extremely high and extremely low temperatures.

This object is achieved by the subject-matter of the independent claims. Preferred embodiments are specified in the corresponding dependent claims, and the items, preferred embodiments and special features of the present invention are described hereinafter.

The present invention firstly provides a compound of the formula I

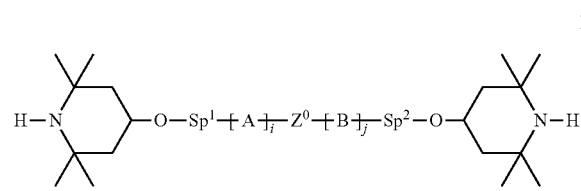

I where
Sp$^1$ and Sp$^2$ are each independently a spacer group,
A and B are each independently a radical selected from the following groups:
  a) the group consisting of trans-1,4-cyclohexylene, 1,4-cyclohexenylene and 1,4'-bicyclohexylene, in which one or two nonadjacent CH$_2$ groups may also be replaced by —O— and/or —S— and in which one or more hydrogen atoms may also be replaced by F,
  b) the group consisting of 1,4-phenylene and 1,3-phenylene, in which one or two nonadjacent CH groups may also be replaced by N and in which one or more hydrogen atoms may also be replaced by L, and
  c) the group consisting of

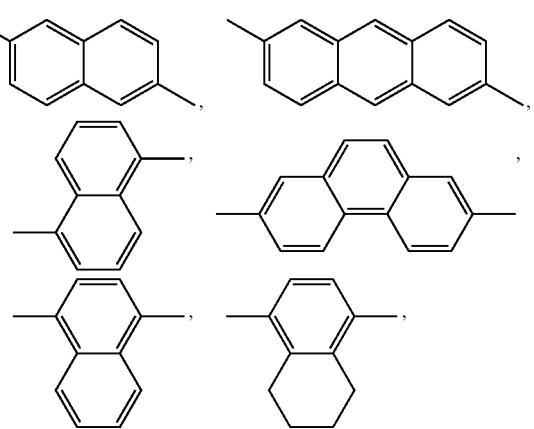

in which one or more hydrogen atoms in these radicals may also be replaced by L, and/or one or more double bonds may be replaced by single bonds, and/or one or more CH groups may be replaced by N,
i and j are each independently 0 or 1,
Z$^0$ is a single bond, —CH$_2$—, —CF$_2$—, —CO—, —O—, —NH—, —NH—(CO)—, —CH$_2$CH$_2$—, —CH═CH—, —CF$_2$O—, —OCF$_2$—, —CH$_2$O—, —OCH$_2$—, —COO—, —OCO—, —C$_2$F$_4$— or —CF═CF—, preferably a single bond, —CF$_2$O— or —COO—, and L is the same or different at each instance and is F, Cl, CN or a straight-chain or branched, in each case optionally fluorinated alkyl, alkoxy, arylalkyl or alkylarylalkyl having 1 to 15 carbon atoms, in which one or more nonadjacent $CH_2$ groups may also be replaced by —O— and/or —S—.

B is preferably trans-1,4-cyclohexylene in which one or more nonadjacent $CH_2$ groups may also be replaced by —O— and/or —S— and in which one or more hydrogen atoms may also be replaced by F, or 1,4-phenylene in which one or two nonadjacent CH groups may also be replaced by N and in which one or more hydrogen atoms may also be replaced by L.

The invention includes embodiments where i and j are each 0, where i and j are each 1, and where one of i and j is 0 and the other of i and j is 1.

In the present invention, it has advantageously been recognized that the inventive compounds of formula I surprisingly have favourable properties and are especially suitable for stabilizing liquid-crystal mixtures both against UV stress and against thermal stress considerably, in many cases to a sufficient degree.

It has also been found that the compounds of formula I have adequate polarity and solubility in liquid-crystalline media. Furthermore, they may have adequate molecular flexibility and favourable interaction and anchoring to surfaces. This combination of properties can advantageously contribute to achieving effective and efficient stabilization of liquid-crystalline media.

It has also been found that, surprisingly, the compounds according to the invention are especially suitable for stabilizing liquid-crystalline media having a nematic phase and negative dielectric anisotropy, especially in the presence of an alignment layer composed, for example, of polyimide.

The present invention thus further provides for the use of one or more compounds of formula I for stabilization of a liquid-crystalline medium, preferably a liquid-crystalline medium having a nematic phase and negative dielectric anisotropy.

As further subject-matter, the present invention provides a process for preparing the inventive compounds of formula I, wherein 4-hydroxy-2,2,6,6-tetramethylpiperidinyloxyl, also called 4-hydroxy-TEMPO or TEMPOL, is used in the process.

In the present invention, it has been recognized that the inventive compounds of the formula I can be prepared in a surprisingly efficient process by using TEMPOL as a starting material. The advantageous compounds of formula I can thus be obtained in an appropriate and useful manner through the use of TEMPOL, or are obtainable thereby.

The present invention further provides a liquid-crystalline medium comprising one or more inventive compounds of formula I and one or more mesogenic compounds.

It has advantageously been recognized that the compounds of formula I can surprisingly effectively and efficiently stabilize liquid-crystalline media, especially against UV and/or thermal stress. Thus, in accordance with the invention, liquid-crystalline media that enable reliable functioning and performance even under comparatively demanding conditions and over comparatively long periods are provided. For example, unwanted display effects such as image sticking or mura can be avoided or distinctly reduced even under extreme conditions or after extreme stresses.

Adequate stabilization of liquid-crystal mixtures both against UV stress and against thermal stress can especially also be achieved when, in addition to the compound of the formula I or the compounds of the formula I, one or more further compounds, preferably phenolic stabilizers, are present in the liquid-crystal mixture. These further compounds are preferably used as stabilizers against thermal stresses.

A further item of subject-matter relates to electrooptical displays or electrooptical components comprising a medium according to the invention.

It has been found that, surprisingly, it is possible to achieve liquid-crystal displays having good stability to break down as a result of thermal and UV stress and have a stable high VHR, even including the initial VHR when the liquid-crystal mixtures according to the invention are used in these display devices.

The media according to the invention are especially suitable for electrooptical displays with active matrix addressing based on the ECB effect and for IPS and FFS displays.

Without thus restricting the present invention, the detailed description of the items, preferred embodiments and special features that follows is intended to clearly illustrate the invention and describe particular embodiments in more detail.

The present invention provides compounds of the formula I having advantageous properties for the stabilization of liquid-crystalline media in particular.

The compounds according to the invention here each have two tetramethylpiperidinyl groups each joined to one another via an ether bond and the further groups shown in the formula I. Thus, in an advantageous manner, two ether-bonded HALS groups, i.e. specific sterically hindered secondary amines bearing no hydrogen atoms on the α-carbon atoms, per molecule are provided in such a way that they are able to effectively and efficiently stabilize liquid-crystal mixtures both against UV stress and against thermal stress.

The presently provided combination of structural elements of formula I, especially the two HALS groups, the direct ether bonds and the further defined groups, including the spacer groups and any lateral substituents, besides the direct stabilizing effect by the HALS groups gives sufficient polarity and solubility in liquid-crystalline media and sufficient molecular flexibility and, as the case may be, favourable interaction and anchoring with surfaces.

This combination of properties can advantageously contribute to achieving sufficient stabilization of liquid-crystalline media. More particularly, it has been recognized that the use of the compounds according to the invention and of media comprising these compounds is advantageous in liquid-crystal displays in which surface influences, for example originating from alignment layers of polyimide and the associated interactions, can be significant.

According to the formula I, $Sp^1$ and $Sp^2$ are each independently a spacer group. The term "spacer group" is known to those skilled in the art and is described in the literature; see, for example, Pure Appl. Chem. 73(5), 888 (2001) and C. Tschierske, G. Pelzl, S. Diele, Angew. Chem. 2004, 116, 6340-6368.

In this context, the spacer groups are advantageously and preferably flexible linking or bridging groups, i.e. flexible segments. In a preferred embodiment, $Sp^1$ and $Sp^2$ are each independently straight-chain or branched alkylene, preferably straight-chain alkylene, having 1 to 12 carbon atoms which is optionally mono- or polysubstituted by F, Cl or CN, and in which one or more nonadjacent $CH_2$ groups may each independently be replaced by —O—, —S—, —NH—, —CO—, —COO—, —OCO—, —OCO—O—, —CH═CH— or —C≡C—. The optional replacement is effected in such a way that no two oxygen atoms are directly bonded to one another in the molecule.

Typical and particularly preferred spacer groups $Sp^1$ and $Sp^2$, in each case independently, are, for example, —$(CH_2)_{p1}$—, —$(CH_2CH_2O)_{q1}$—$CH_2CH_2$—, —$CH_2CH_2$—S—$CH_2CH_2$— and —$CH_2CH_2$—NH—$CH_2CH_2$—, in which p1 is an integer from 1 to 12, more preferably 2 to 12, and q1 is an integer from 1 to 3.

Particularly preferred groups are, for example, straight-chain ethylene, propylene, butylene, pentylene, hexylene, heptylene, octylene, nonylene, decylene, undecylene, dodecylene, octadecylene, ethylenoxyethylene, methylenoxybutylene, ethylenethioethylene, ethylene-N-methyliminoethylene, 1-methylalkylene, ethenylene, propenylene and butenylene.

In a particularly preferred embodiment, $Sp^1$ and $Sp^2$, in each case independently, are ethylene, propylene, butylene, pentylene, hexylene, heptylene, and especially propylene.

In one embodiment, $Sp^1$ and $Sp^2$ do not include a group —CO—.

It is preferable that $Sp^1$ and $Sp^2$ have the same definition, i.e. the same structure.

In one embodiment,

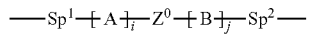

is straight-chain or branched alkylene, preferably having 9 to 16 carbon atoms, which is optionally mono- or polysubstituted by F, Cl or CN, and in which one or more nonadjacent $CH_2$ groups may also each independently be replaced by —O—, —S—, —NH—, —CO—, —COO—, —OCO—, —OCO—O—, —CH=CH— or —C≡C—.

In a further embodiment, the above grouping is not —C(O)-alkyl-C(O)—.

In a preferred embodiment,

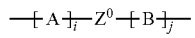

is a group selected from -Cyc-, -Phe-, -Cyc-Cyc-, -Cyc-Phe-, -Phe-Cyc-, -Phe-Phe-, -Cyc-Z-Cyc-, -Cyc-Z-Phe-, -Phe-Z-Cyc- and -Phe-Z-Phe-, where Cyc is trans-1,4-cyclohexylene, in which one or more nonadjacent $CH_2$ groups may also be replaced by —O— and/or —S— and in which one or more hydrogen atoms may also be replaced by F, Phe is 1,3-phenylene or 1,4-phenylene, preferably 1,4-phenylene, in which one or two nonadjacent CH groups may also be replaced by N and in which one or more hydrogen atoms may also be replaced by L, Z is —$CH_2$—, —$CF_2$—, —CO—, —O—, —NH—, —NH—(CO)—, —$CH_2CH_2$—, —CH=CH—, —$CF_2O$—, —$OCF_2$—, —$CH_2O$—, —$OCH_2$—, —COO—, —OCO—, —$C_2F_4$— or —CF=CF—, and L has the definition given above for formula I.

Preferably,

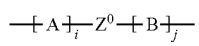

has one of the following structures:

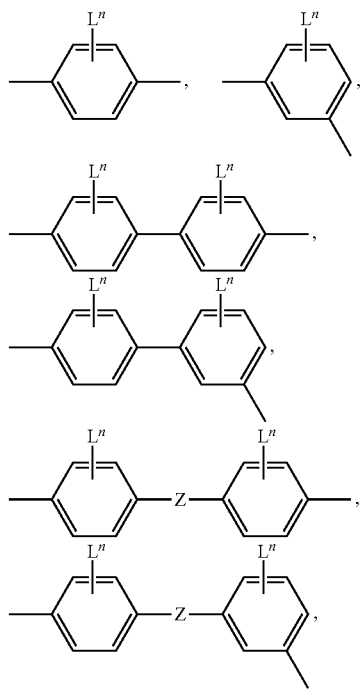

where

Z is —$CH_2$—, —$CF_2$—, —CO—, —O—, —NH—, —NH—(CO)—, —$CH_2CH_2$—, —CH=CH—, —$CF_2O$—, —$OCF_2$—, —$CH_2O$—, —$OCH_2$—, —COO—, —OCO—, —$C_2F_4$— or —CF=CF—, preferably —$CF_2O$— or —COO—, and $L^n$ is in each case independently 1, 2, 3 or 4, preferably 1 or 2, optional substituents L, where L is the same or different at each instance and is F, Cl, CN or a straight-chain or branched, in each case optionally fluorinated alkyl, alkoxy, arylalkyl or alkylarylalkyl having 1 to 15 carbon atoms, in which one or more nonadjacent $CH_2$ groups may also be replaced by —O— and/or —S—.

In one embodiment, the group

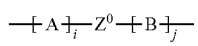

comprises one of the following structures:

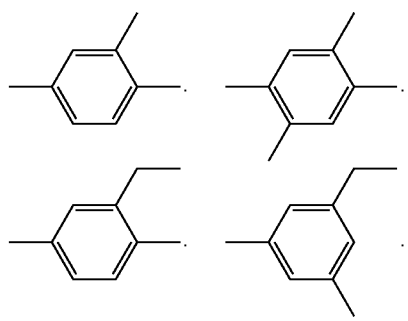

-continued

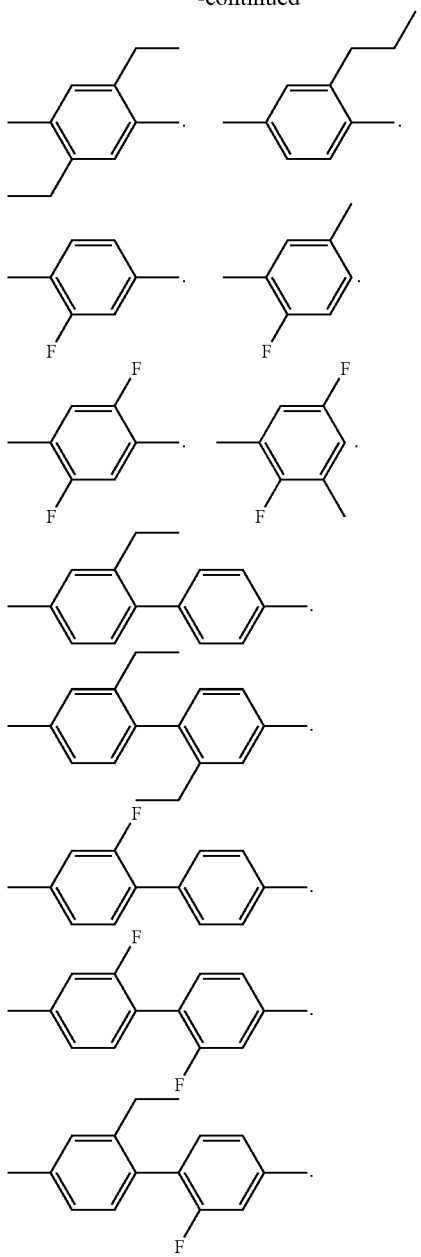

-continued

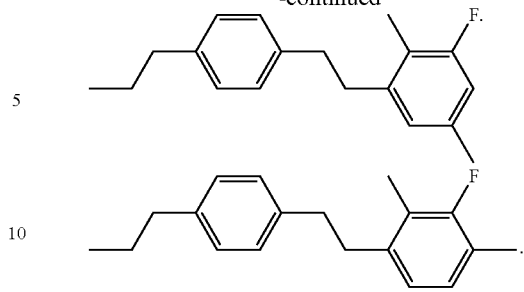

where the group preferably consists of one of these structures.

In a preferred embodiment, compounds of the formula I where i=1 and j=0 are provided.

In a particularly preferred embodiment of the invention, the compound(s) of the invention is/are selected from compounds of the formula I-A

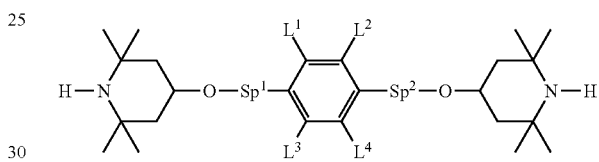

I-A where $Sp^1$ and $Sp^2$ have the definitions given above and $L^1$ to $L^4$ are each independently H, F or straight-chain or branched, in each case optionally fluorinated alkyl having 1 to 7 carbon atoms, in which one or more nonadjacent $CH_2$ groups may also be replaced by —O—.

More particularly, $L^1$ to $L^4$ are more preferably each independently H, F or straight-chain alkyl having 1 to 6 carbon atoms. In one embodiment, at least two of $L^1$ to $L^4$ are H, where the remaining group(s) from $L^1$ to $L^4$ is/are selected from F, methyl, ethyl and propyl.

If i=0 and j=0, in a preferred embodiment, the $Sp^1$, $Z^0$ and $Sp^2$ groups together form an unbranched alkyl group, preferably having at least 9 carbon atoms, further preferably having 9 to 16 carbon atoms.

Particularly preferred compounds of the formula I are selected from the following compounds of the formulae I-1 to I-12:

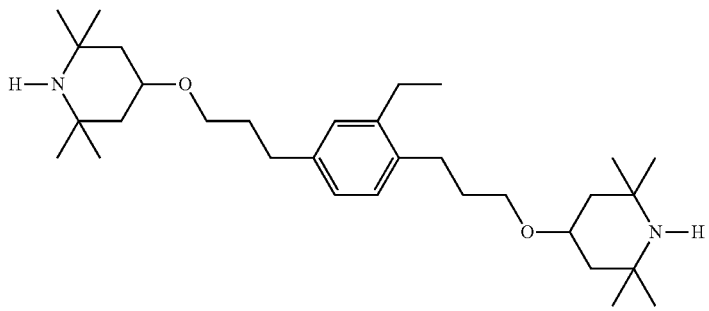

I-1

-continued
I-2
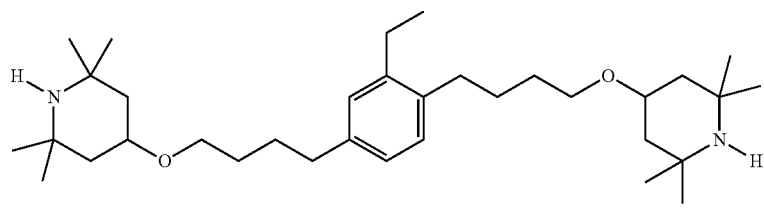
I-3
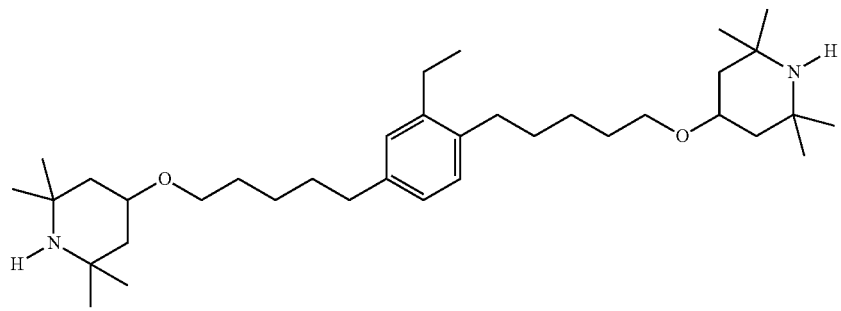
I-4
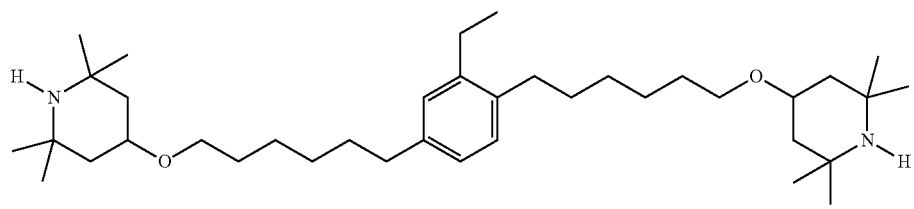
I-5
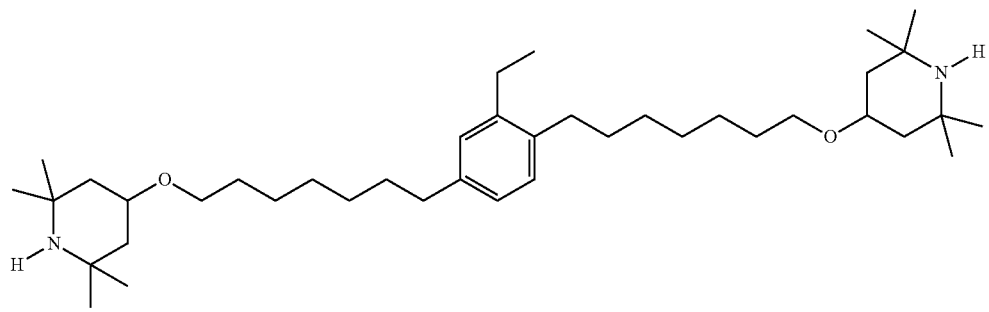
I-6
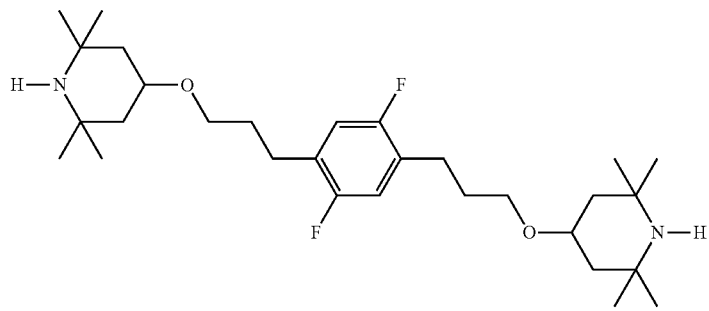
I-7
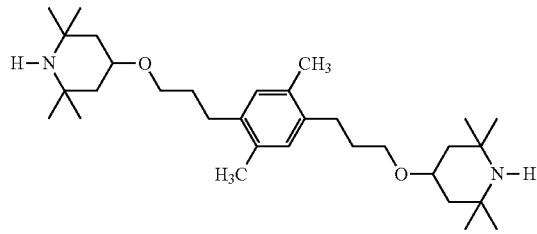
I-8
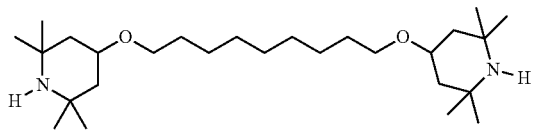

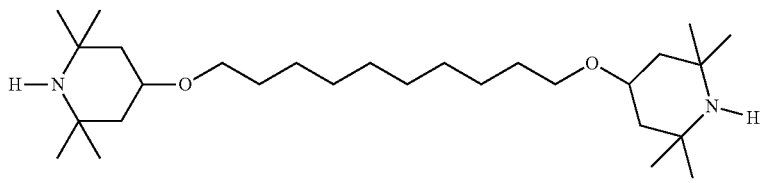

I-9

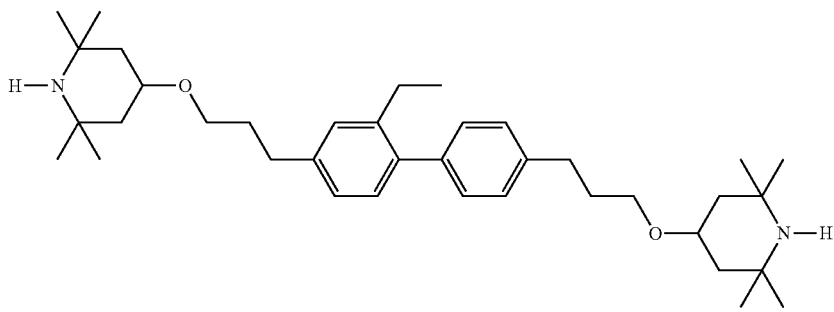

I-10

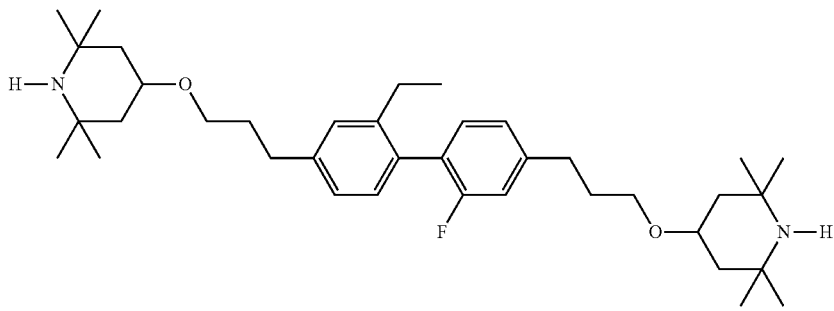

I-11

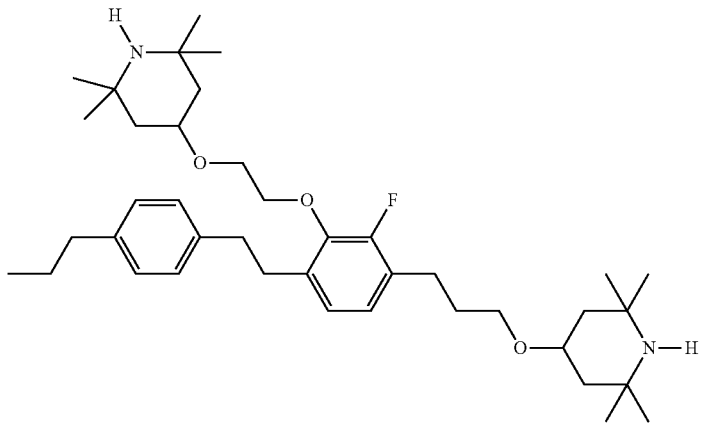

I-12

In a particularly preferred embodiment, the compound of the formula I is a compound of the formula I-1, I-2, I-3, I-4, I-5, I-6 or I-7, especially I-1.

These compounds are of particularly excellent suitability as stabilizers in liquid-crystal mixtures, in which case they especially stabilize the VHR of the mixtures against UV stress.

The inventive compounds of the formula I can be prepared by standard methods known from the literature and, as the case may be, standard modifications known to those skilled in the art (see, for example, Houben-Weyl, Methoden der Organischen Chemie [Methods of Organic Chemistry], Thieme-Verlag, Stuttgart).

In the present case, it has advantageously been recognized that a particularly favourable and effective process for preparing the compounds of the formula I can be provided by using TEMPOL as a starting material.

A general synthesis method for preparation of compounds according to the invention is shown below.

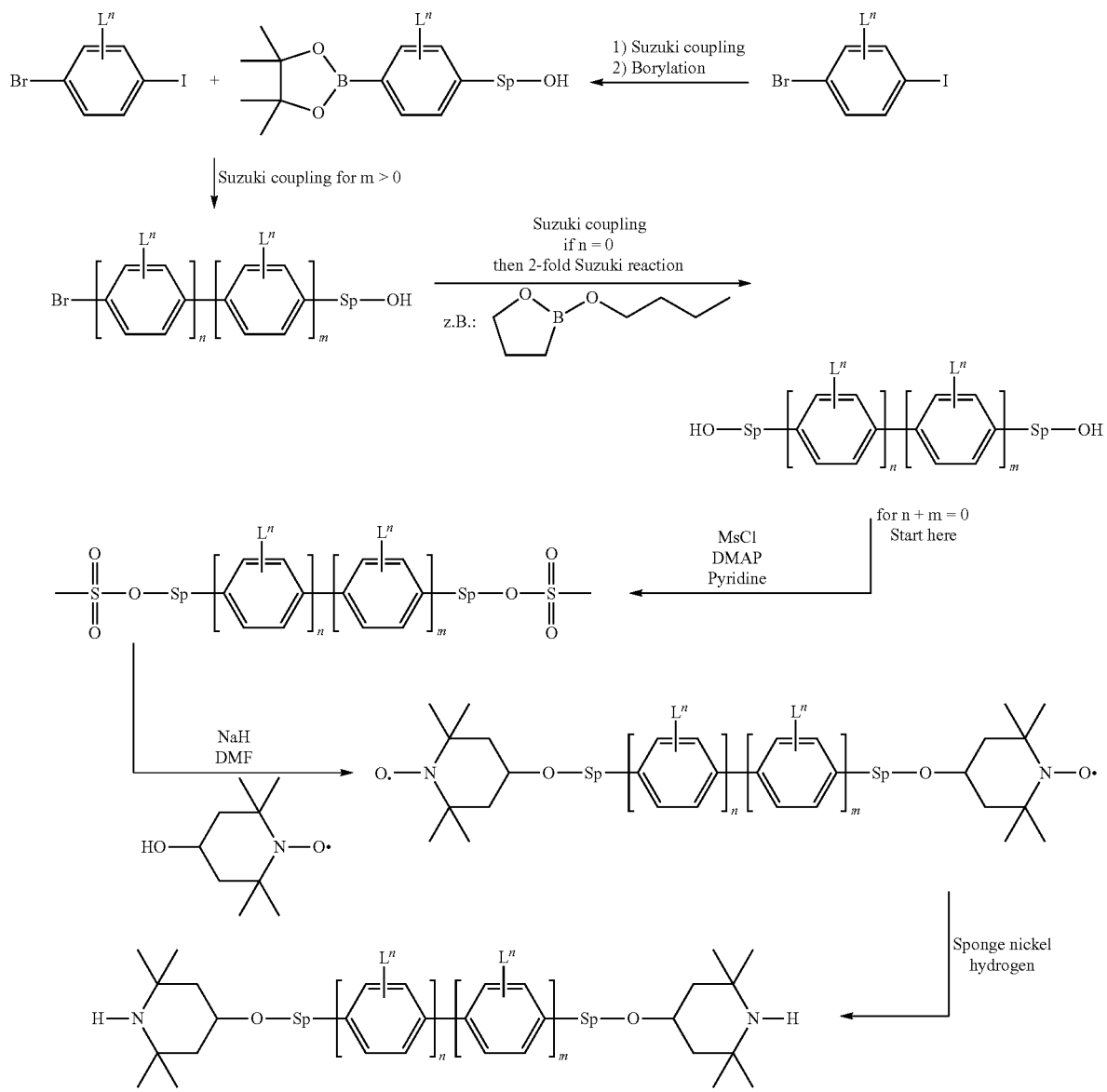

where n and m are each independently 0 or 1 and L" is in each case independently 1, 2, 3 or 4 optional substituents L, where L is the same or different at each instance and is F, Cl, CN or a straight-chain or branched, in each case optionally fluorinated alkyl, alkoxy, arylalkyl or alkylarylalkyl having 1 to 15 carbon atoms, in which one or more nonadjacent $CH_2$ groups may also be replaced by —O— and/or —S—.

According to the invention, one or more compounds of the formula I can advantageously be used for stabilization of liquid-crystalline media. More particularly, the compounds according to the invention can have a favourable effect on stability in the case of dielectrically negative liquid-crystalline media, especially in the presence of one or more alignment layers of polyimide, for example. In the displays according to the invention, this can advantageously lead to particularly short switching times with a simultaneously high voltage holding ratio (VHR).

For this purpose, a method of stabilizing a liquid-crystalline medium is provided, wherein one or more compounds of the formula I are added to the medium.

In a preferred embodiment, the stabilization relates to a liquid-crystalline medium having a negative dielectric anisotropy. In this case, at the most appreciable amounts of dielectrically uncharged liquid-crystal compounds and generally only very small amounts of dielectrically positive compounds, if any, are used, since liquid-crystal displays are generally supposed to have minimum drive voltages.

Preferably, the liquid-crystalline media according to the invention comprise one or more compounds selected from the group of compounds of the formulae II-1 to II-4

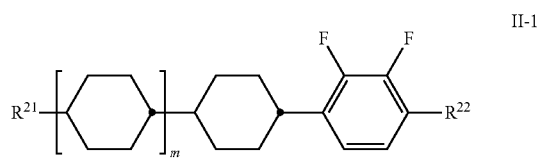

-continued

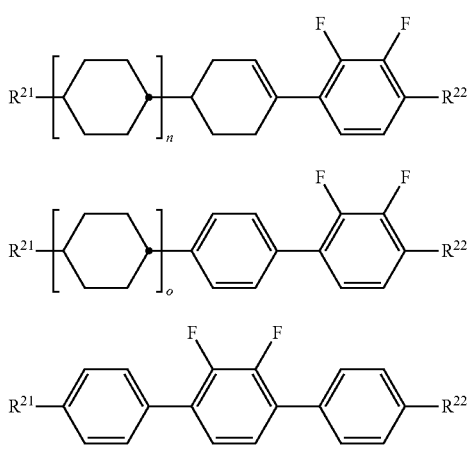

where
R$^{21}$ is a unsubstituted alkyl radical having 1 to 7 carbon atoms,
R$^{22}$ is an unsubstituted alkyl radical having 1 to 7 carbon atoms, or an unsubstituted alkoxy radical having 1 to 6 carbon atoms,
and
m, n and o are each independently 0 or 1.

It has been found that, surprisingly, it is possible to achieve liquid-crystal mixtures which, especially in ECB displays and for IPS or FFS displays with active matrix addressing, have a low threshold voltage coupled with short switching times and simultaneously have a sufficiently broad nematic phase, a favourable, relatively low birefringence (Δn), good stability to breakdown by thermal and UV stress and a stable high VHR when nematic liquid-crystal mixtures comprising at least one compound of the formula I and at least one compound selected from the group of compounds of the formulae II-1 to II-4, preferably of the formula II-3, are used.

The mixtures according to the invention preferably exhibit very broad nematic phase regions with clearing points ≥70° C., very favourable values for the capacitative threshold, relatively high values for VHR and simultaneously good low-temperature stabilities at −20° C. and −30° C., and also very low rotational viscosities. Moreover, the mixtures according to the invention preferably feature a good ratio of clearing point and rotational viscosity, and a high negative dielectric anisotropy.

It has also been found that, surprisingly, it is possible to achieve liquid-crystalline media having a suitably high Δε, a suitable phase region and a suitable Δn, which have the disadvantages of the prior art materials at least to a considerably lesser degree, if at all. More particularly, it has been found here, surprisingly, that the compounds of the formula I, even when they are used alone without additional thermal stabilizers, lead to considerable stabilization, in many cases sufficient stabilization, of liquid-crystal mixtures both against UV stress and against thermal stress.

Preferably, the medium according to the invention comprises one or more compounds selected from the group of compounds of the formulae II-1 to II-4 in a total concentration in the range from 10% or more to 80% or less, preferably from 15% or more to 70% or less, more preferably from 20% or more to 60% or less.

Especially preferably, the medium according to the invention comprises
one or more compounds of the formula II-1 in a total concentration in the range of 5% or more to 30% or less and/or
one or more compounds of the formula II-2 in a total concentration in the range of 3% or more to 30% or less and/or
one or more compounds of the formula II-3 in a total concentration in the range of 5% or more to 30% or less and/or
one or more compounds of the formula II-4 in a total concentration in the range of 1% or more to 30% or less.

In a preferred embodiment of the present invention, the media according to the invention comprise one or more compounds of the formula II-1, preferably one or more compounds selected from the group of compounds of the formulae II-1-1 and II-1-2

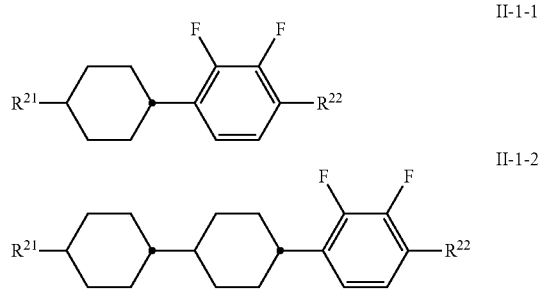

where R$^{21}$ and R$^{22}$ have the definition given above for formula II-1, and preferably
R$^{21}$ is an alkyl radical having 2 to 5 carbon atoms, more preferably having 3 to 5 carbon atoms, and
R$^{22}$ is an alkyl or alkoxy radical having 2 to 5 carbon atoms, more preferably an alkoxy radical having 2 to 4 carbon atoms, or an alkylenyloxy radical having 2 to 4 carbon atoms.

In a preferred embodiment of the present invention, the media according to the invention comprise one or more compounds of the formula II-2, more preferably one or more compounds selected from the group of compounds of the formulae II-2-1 and II-2-2

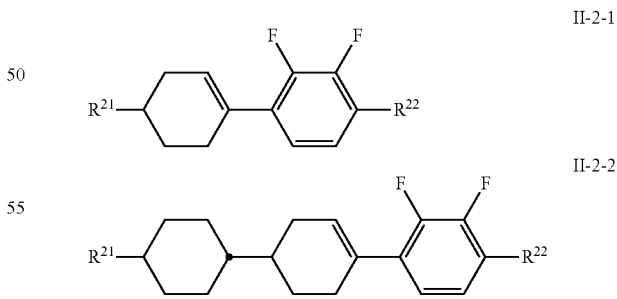

where R$^{21}$ and R$^{22}$ have the definition given above for formula II-2, and preferably
R$^{21}$ is an alkyl radical having 2 to 5 carbon atoms, more preferably having 3 to 5 carbon atoms, and
R$^{22}$ is an alkyl or alkoxy radical having 2 to 5 carbon atoms, more preferably an alkoxy radical having 2 to 4 carbon atoms or an alkylenyloxy radical having 2 to 4 carbon atoms.

In a preferred embodiment of the present invention, the media according to the invention comprise one or more compounds of the formula II-3, more preferably one or more compounds selected from the group of compounds of the formulae II-3-1 and II-3-2, most preferably of the formula II-3-2,

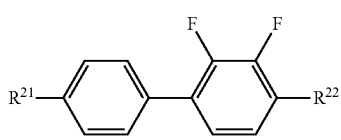

II-3-1

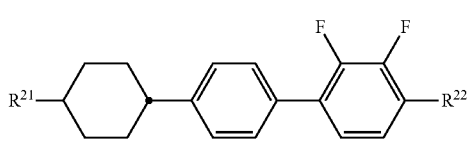

II-3-2 where $R^{21}$ and $R^{22}$ have the definition given above for formula II-3, and preferably
$R^{21}$ is an alkyl radical having 2 to 5 carbon atoms, more preferably having 3 to 5 carbon atoms, and
$R^{22}$ is an alkyl or alkoxy radical having 2 to 5 carbon atoms, more preferably an alkoxy radical having 2 to 4 carbon atoms or an alkylenyloxy radical having 2 to 4 carbon atoms.

In a further preferred embodiment, the medium comprises one or more compounds of the formula II-4, more preferably of the formula II-4-a,

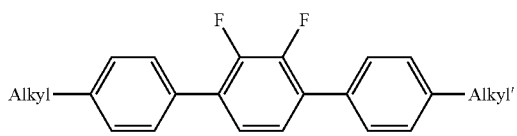

II-4-a where
Alkyl and Alkyl' are independently alkyl having 1 to 7 carbon atoms, preferably having 2 to 5 carbon atoms.

In a particularly preferred embodiment, the media according to the invention may additionally comprise one or more compounds of the formula III-3 and/or formula IV,

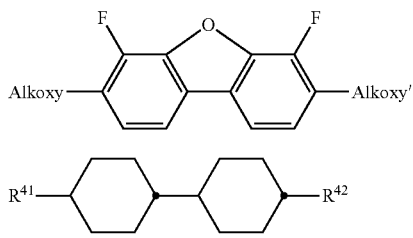

III-3

IV where
Alkoxy, Alkoxy' are independently an alkoxy radical having 1 to 5 carbon atoms,
$R^{41}$ is an unsubstituted alkyl radical having 1 to 7 carbon atoms or an unsubstituted alkenyl radical having 2 to 7 carbon atoms, and
$R^{42}$ is an unsubstituted alkyl radical having 1 to 7 carbon atoms, an unsubstituted alkoxy radical having 1 to 6 carbon atoms or an unsubstituted alkenyl radical having 2 to 7 carbon atoms.

More preferably, the medium according to the invention, in addition to the compounds selected from the group of compounds of the formulae II-1 to II-4, comprises one or more compounds of the formula III-3 in a total concentration in the range from 1% or more to 20% or less, preferably from 2% or more to 15% or less, more preferably from 3% or more to 10% or less.

In addition, the medium according to the invention may comprise one or more compounds of the formulae III-1 and III-2

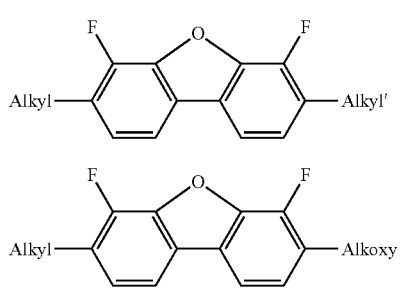

III-1

III-2 where
Alkyl, Alkyl' are alkyl having 1 to 7 carbon atoms, preferably having 2-5 carbon atoms,
and
Alkoxy, Alkoxy' are alkoxy having 1 to 7 carbon atoms, preferably having 2 to 5 carbon atoms.

Preferably, the media according to the present invention comprise one or more dielectrically uncharged compounds of the formula IV in a total concentration in the range from 5% or more to 90% or less, preferably from 10% or more to 80% or less, more preferably from 20% or more to 70% or less.

In a particularly preferred embodiment, the medium according to the invention comprises one or more compounds of the formula IV selected from the group of compounds of the formulae IV-1 to IV-4

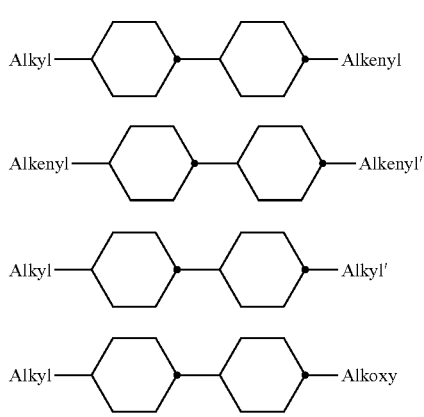

IV-1

IV-2

IV-3

IV-4 where
Alkyl and Alkyl' are independently alkyl having 1 to 7 carbon atoms, preferably having 2 to 5 carbon atoms, Alkenyl is an alkenyl radical having 2 to 5 carbon atoms, preferably having 2 to 4 carbon atoms, more preferably 2 carbon atoms, Alkenyl' is an alkenyl radical having 2 to 5 carbon atoms, preferably having 2 to 4 carbon atoms, more preferably having 2 to 3 carbon atoms, and Alkoxy is alkoxy having 1 to 5 carbon atoms, preferably having 2 to 4 carbon atoms.

In a particularly preferred embodiment, the media according to the invention comprise one or more compounds of the formula IV-1 and/or one or more compounds of the formula IV-2.

In addition, the liquid-crystalline media according to the invention may optionally comprise one or more compounds of the formula V

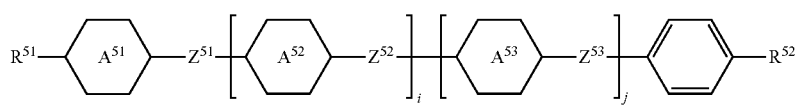

where $R^{51}$ and $R^{52}$ independently have one of the definitions given for $R^{21}$ and $R^{22}$, preferably alkyl having 1 to 7 carbon atoms, alkoxy having 1 to 7 carbon atoms and alkoxyalkyl, alkenyl or alkenyloxy having 2 to 7 carbon atoms, particularly n-alkyl having 1 to 5 carbon atoms, n-alkoxy having 2 to 5 carbon atoms and alkenyl or alkenyloxy having 2 to 4 carbon atoms, and

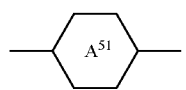

to

if present, are each independently

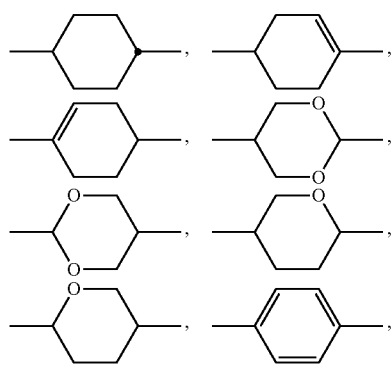

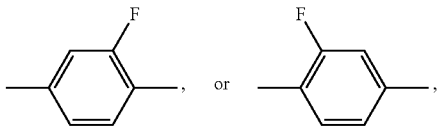

preferably

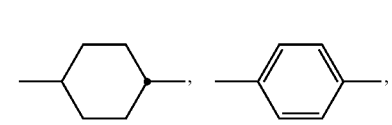

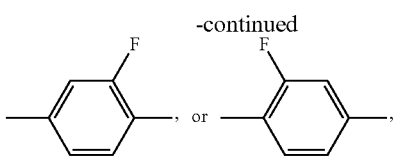

preferably

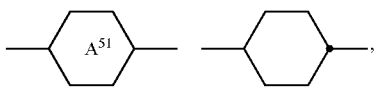

and, if present,

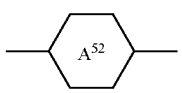

is preferably

$Z^{51}$ to $Z^{53}$ are each independently —$CH_2$—$CH_2$—, —$CH_2$—O—, —CH=CH—, —C≡C—, —COO— or a single bond, preferably —$CH_2$—$CH_2$—, —$CH_2$—O— or a single bond, preferably a single bond, i and j are each independently 0 or 1, and (i+j) is preferably 0 or 1.

Preferably, the media according to the invention comprise the following compounds in the total concentrations specified:

5-60% by weight of one or more compounds selected from the group of compounds of the formulae II-1 to II-4 and III-1 to III-3, and/or 10-60% by weight of one or more compounds selected from the group of compounds of the formulae II-1 to II-4 and/or 10-60% by weight of one or more compounds of the formulae IV and/or V, where the total content of all the compounds in the medium is 100%.

In a further preferred embodiment, the medium comprises one or more compounds of the formula V selected from the group of compounds of the formulae V-1 to V-10, preferably selected from the group of compounds of the formulae V-1 to V-5

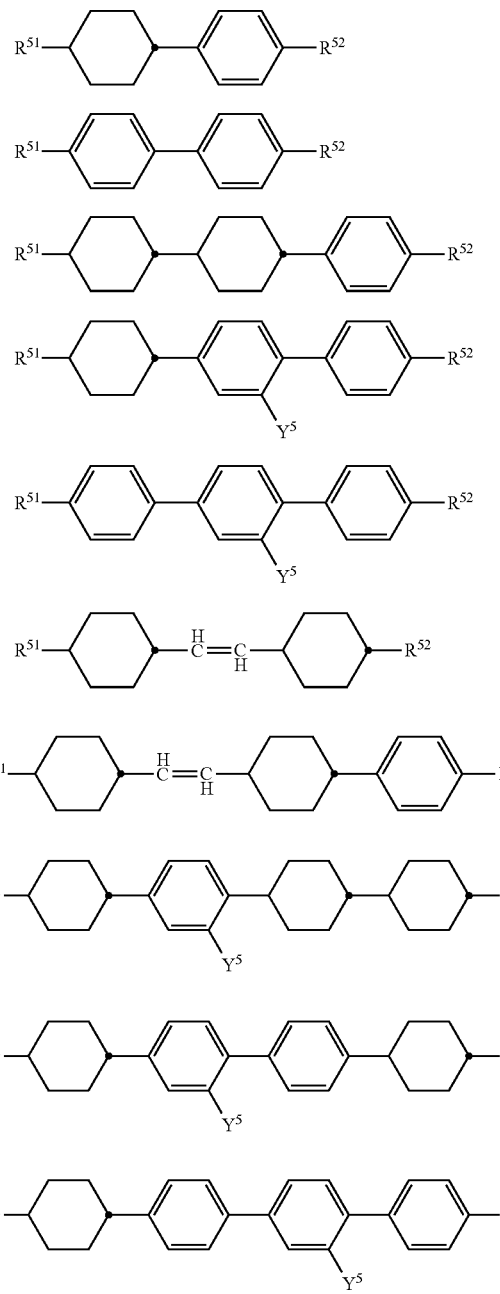

in which the radicals have the definitions given above under formula V and
$Y^5$ is H or F,
and preferably
$R^{51}$ is alkyl having 1 to 7 carbon atoms or alkenyl having 2 to 7 carbon atoms and
$R^{52}$ is alkyl having 1 to 7 carbon atoms, alkenyl having 2 to 7 carbon atoms or alkoxy having 1 to 6 carbon atoms.

In a further preferred embodiment, the medium according to the invention comprises one or more compounds of the formula V-1 selected from the group of compounds of the formulae V-1a and V-1b, preferably of the formula V-1b,

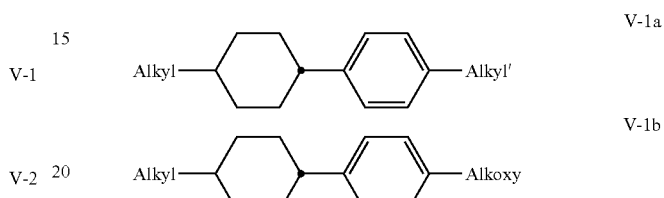

in which
Alkyl and Alkyl' are independently alkyl having 1 to 7 carbon atoms, preferably having 2 to 5 carbon atoms,
Alkoxy is alkoxy having 1 to 5 carbon atoms, preferably having 2 to 4 carbon atoms.

In a further preferred embodiment, the medium comprises one or more compounds of the formula V-3 selected from the group of compounds of the formulae V-3a and V-3b

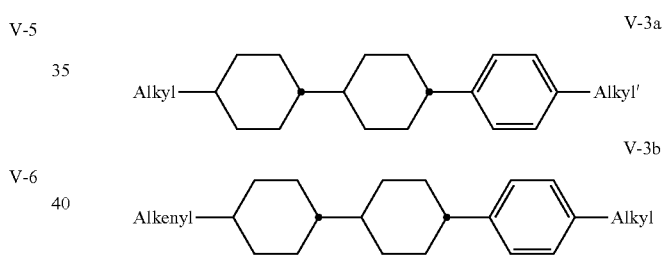

in which
Alkyl and Alkyl' are independently alkyl having 1 to 7 carbon atoms, preferably having 2 to 5 carbon atoms, and
Alkenyl is alkenyl having 2 to 7 carbon atoms, preferably having 2 to 5 carbon atoms.

In a further preferred embodiment, the medium comprises one or more compounds of the formula V-4 selected from the group of compounds of the formulae V-4a and V-4b

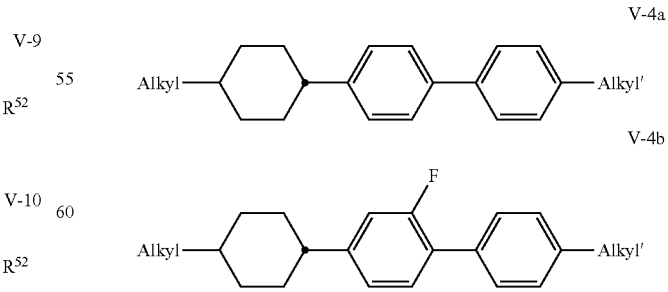

in which
Alkyl and Alkyl' are independently alkyl having 1 to 7 carbon atoms, preferably having 2 to 5 carbon atoms.

The present invention also relates to a method of stabilizing a liquid-crystalline medium comprising one or more compounds selected from the group of compounds of the formulae II-1 to II-4 and/or one or more compounds of the formula IV and/or one or more compounds of the formula V, wherein one or more compounds of the formula I are added to the medium.

The liquid-crystal media according to the present invention may comprise one or more chiral compounds.

In a particularly preferred embodiment of the present invention, the liquid-crystalline media comprise one or more compounds of the formula

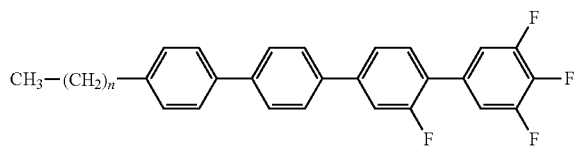

in which n is 0, 1, 2, 3, 4, 5 or 6, preferably 2 or 4, more preferably 2, preferably in a concentration of 0.1% to 5%, more preferably of 0.2% to 1%.

Particularly preferred embodiments of the present invention fulfil one or more of the conditions which follow, where the acronyms (abbreviations) are elucidated in Tables A to C and illustrated by examples in Table D.

i. The liquid-crystalline medium has a birefringence of 0.06 or more, more preferably of 0.07 or more.
ii. The liquid-crystalline medium has a birefringence of 0.13 or less, more preferably of 0.12 or less.
iii. The liquid-crystalline medium has a birefringence in the range from 0.09 or more to 0.12 or less.
iv. The liquid-crystalline medium has a negative dielectric anisotropy with a magnitude of 2.0 or more, more preferably of 2.5 or more.
v. The liquid-crystalline medium has a negative dielectric anisotropy with a magnitude of 5.5 or less, more preferably of 5.0 or less.
vi. The liquid-crystalline medium has a negative dielectric anisotropy with a magnitude in the range from 3.0 or more to 4.5 or less.
vii. The liquid-crystalline medium comprises one or more particularly preferred compounds of the formula IV selected from the following formulae:

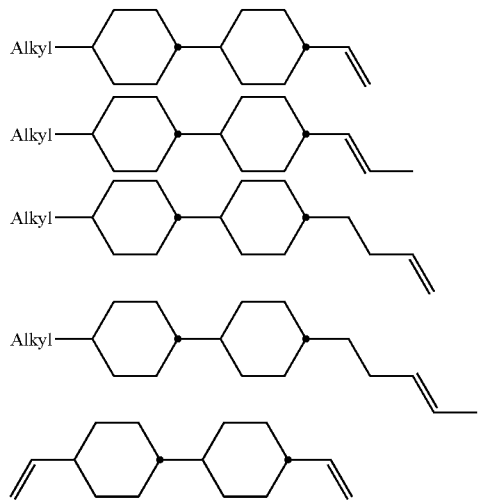

-continued

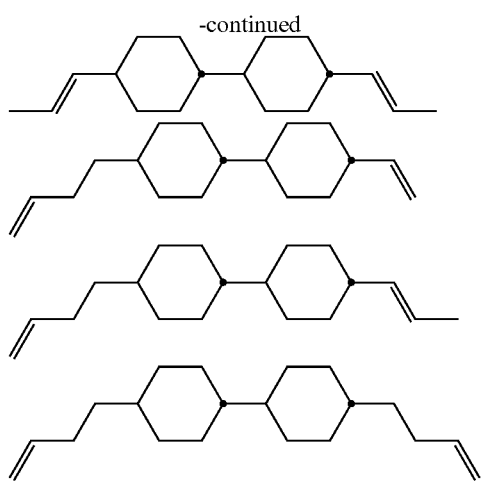

in which alkyl has the definition given above and is preferably in each case independently alkyl having 1 to 6 and more preferably having 2 to 5 carbon atoms, and especially preferably n-alkyl.
viii. The total concentration of the compounds of the formula IV in the overall mixture is 20% or more, preferably 30% or more, and is preferably in the range from 20% or more to 49% or less, more preferably in the range from 29% or more to 47% or less, and most preferably in the range from 37% or more to 44% or less.
ix. The liquid-crystalline medium comprises one or more compounds of the formula IV selected from the group of compounds of the following formulae: CC-n-V and/or CC-n-Vm, especially CC-3-V, preferably in a concentration of up to 50% or less, more preferably up to 42% or less, and optionally additionally CC-3-V1, preferably in a concentration of up to 15% or less, and/or CC-4-V, preferably in a concentration of up to 20% or less, more preferably up to 10% or less.
x. The total concentration of the compounds III-1 to III-3 in the overall mixture is in the range from 1% or more to 20% or less, preferably from 2% or more to 15% or less, more preferably from 3% or more to 10% or less.
xi. The total concentration of the compounds of the formula CC-3-V in the overall mixture is 18% or more, preferably 25% or more.
xii. The proportion of compounds of the formulae II-1 to II-4 and III-1 to III-3 in the overall mixture is 50% or more and preferably 75% or less.
xiii. The liquid-crystalline medium consists essentially of compounds of the formulae I, II-1 to II-4, III, IV and V, preferably of compounds of the formulae I, II-1 to II-4 and IV.
xiv. The liquid-crystalline medium comprises one or more compounds of the formula IV, preferably of the formulae IV-1 and/or IV-2, preferably in a total concentration of 20% or more, especially of 25% or more, and most preferably from 30% or more to 45% or less.

Preferably, the liquid-crystal mixture has a nematic phase region having a breadth of at least 80 K and a flow viscosity $v_{20}$ of not more than 30 mm$^2 \cdot$s$^{-1}$ at 20° C.

The liquid-crystal mixture according to the invention preferably has a Δε of −0.5 to −8.0, further preferably of −1.5 to −6.0, and most preferably of −2.0 to −5.0, where Δε is the dielectric anisotropy.

The rotational viscosity $\gamma_1$ is preferably 200 mPa·s or less, especially 150 mPa·s or less, more preferably 120 mPa·s or less.

The preferred mixtures of the invention with negative Δε are suitable for all VA-TFT applications, for example VAN, MVA, (S)-PVA and ASV. In addition, they are suitable for IPS (In plane switching), FFS (Fringe field switching) and PALC applications with negative Δε.

The nematic liquid-crystal mixtures in the displays according to the invention generally comprise two components A and B which in turn consist of one or more individual compounds.

The liquid-crystalline media according to the invention preferably comprise 4 to 15, especially 5 to 12 and more preferably 10 or fewer compounds. These are preferably selected from the group of compounds of the formulae I, II-1 to II-4, and/or IV and/or V.

The liquid-crystalline media according to the invention may optionally also comprise more than 18 compounds. In this case, they preferably comprise 18 to 25 compounds.

As well as compounds of the formulae I to V, it is also possible for other constituents to be present, for example in an amount of up to 45%, but preferably up to 35%, especially up to 10% of the overall mixture.

Optionally, the preferred inventive media with negative Δε may also comprise a dielectrically positive component, the overall concentration of which is preferably 10% or less, based on the overall medium.

In a preferred embodiment, the liquid-crystal media of the invention comprise compounds selected from the group of compounds of the formulae I, II-1 to II-4, III-3, IV and V, preferably selected from the group of compounds of the formulae I and II-1 to II-4, and preferably consist predominantly, more preferably essentially and most preferably virtually entirely of the compounds of the formulae specified.

The liquid-crystal media according to the invention preferably each have a nematic phase at least from −20° C. or less to 70° C. or more, further preferably from −30° C. or less to 80° C. or more, more preferably from −40° C. or less to 85° C. or more, and most preferably from −40° C. or less to 90° C. or more.

In this context, the expression "have a nematic phase" means firstly that, at low temperatures, no smectic phase and no crystallization is observed at the appropriate temperature, and secondly that there is still no occurrence of clarification from the nematic phase in the course of heating. The study at low temperatures is conducted in a flow viscometer at the appropriate temperature and verified by storage in test cells of a layer thickness corresponding to the electrooptical application for at least 100 hours. If the storage stability at a temperature of −20° C. in a corresponding test cell is 1000 h or more, the medium is regarded as stable at this temperature. At temperatures of −30° C. and −40° C., the corresponding periods of time are 500 h and 250 h respectively. At high temperatures, the clearing point is measured by standard methods in capillaries.

In a preferred embodiment, the liquid-crystal media according to the invention are characterized by values of optical anisotropies in the moderate to low range. The birefringence values are preferably in the range from 0.065 or more to 0.13 or less, more preferably in the range from 0.080 or more to 0.12 or less and most preferably in the range from 0.085 or more to 0.110 or less.

In a preferred embodiment, the liquid-crystal media according to the invention have a negative dielectric anisotropy and have relatively high values for the magnitude of the dielectric anisotropy ($|\Delta\varepsilon|$) that are preferably in the range from 2.0 or more to 5.5 or less, preferably to 5.0 or less, preferably from 2.5 or more to 4.7 or less, more preferably from 3.0 or more to 4.7 or less and most preferably from 3.2 or more to 4.5 or less.

The liquid-crystal media according to the invention have relatively low values for the threshold voltage ($V_0$) in the range from 1.7 V or more to 2.5 V or less, preferably from 1.8 V or more to 2.4 V or less, more preferably from 1.9 V or more to 2.3 V or less and most preferably from 1.95 V or more to 2.1 V or less.

In a further preferred embodiment, the liquid-crystal media according to the invention preferably have relatively low values for the mean dielectric anisotropy ($\varepsilon_{av.} \equiv (\varepsilon_\| + 2\varepsilon_\perp)/3$) that are preferably in the range from 5.0 or more to 8.0 or less, preferably from 5.4 or more to 7.5 or less, even more preferably from 5.5 or more to 7.3 or less, especially preferably from 5.6 or more to 7.1 or less and very especially preferably from 5.7 or more to 6.8 or less.

Moreover, the liquid-crystal media according to the invention have high values for the VHR in liquid-crystal cells.

In freshly filled cells at 20° C. in the cells, these values are preferably not less than 95%, preferably not less than 97%, more preferably not less than 98% and most preferably not less than 99%, and after 5 minutes in the oven at 100° C. in the cells are preferably not less than 80%, preferably not less than 85%, more preferably not less than 90% and most preferably not less than 95%.

In general, liquid-crystal media having a low drive voltage or threshold voltage have a lower VHR than those having a greater drive voltage or threshold voltage, and vice versa.

These preferred values for the individual physical properties are preferably also observed in combination in each case by the media according to the invention.

In the present context, the term "compounds", also written as "compound(s)", unless explicitly stated otherwise, means either one compound or multiple compounds.

The individual compounds, unless stated otherwise, are generally each used in the mixtures in concentrations of 1% or more to 30% or less, preferably of 2% or more to 30% or less, and more preferably of 3% or more to 16% or less.

In a preferred embodiment, the liquid-crystalline media according to the invention comprise
the compound of the formula I,
one or more compounds of the formula IV, preferably selected from the group of compounds of the formulae CC-n-V and CC-n-Vm, preferably CC-3-V, CC-3-V1, CC-4-V and CC-5-V, more preferably selected from the group of compounds CC-3-V, CC-3-V1 and CC-4-V, most preferably the compound CC-3-V and optionally additionally the compound CC-4-V and/or CC-3-V1,
one or more compounds of the formula II-1-1, preferably of the formula CY-n-Om, more preferably selected from the group of compounds of the formulae CY-3-O2, CY-3-O4, CY-5-O2 and CY-5-O4,
one or more compounds of the formula II-1-2, preferably selected from the group of compounds of the formulae CCY-n-m and CCY-n-Om, preferably of the formula CCY-n-Om, preferably selected from the group of compounds of the formulae CCY-2-O2, CCY-3-O1, CCY-3-O3, CCY-4-O2, CCY-3-O2 and CCY-5-O2,
optionally one or more compounds of the formula II-2-2, preferably of the formula CLY-n-Om, more preferably selected from the group of compounds of the formulae CLY-2-O4, CLY-3-O2 and CLY-3-O3,
one or more compounds of the formula II-3-2, preferably of the formula CPY-n-Om, more preferably selected from the group of compounds of the formulae CPY-2-O2 and CPY-3-O2, CPY-4-O2 and CPY-5-O2,
one or more compounds of the formula II-4, preferably of the formula PYP-n-m, more preferably selected from the group of compounds of the formulae PYP-2-3 and PYP-2-4, and
one or more compounds of the formula III-3, preferably the compound of the formula B-2O-O5.

Preferably, the total concentration of the one or more compounds of the formula I in the medium according to the invention, based on the overall medium, is 5000 ppm or less, more preferably 2000 ppm or less, even more preferably 1000 ppm or less, especially preferably 500 ppm or less and most preferably 250 ppm or less.

In one embodiment, the concentration of the one or more compounds of the formula I in the medium according to the invention, based on the overall medium, is in the range from 1 ppm to 5000 ppm, preferably in the range from 1 ppm to 2000 ppm, more preferably in the range from 1 ppm to 1000 ppm, especially preferably in the range from 1 ppm to 500 ppm and very especially preferably in the range from 1 ppm to 250 ppm. In a particularly preferred embodiment, the concentration of the one or more compounds of the formula I in the medium according to the invention, based on the overall medium, is in the range from 5 ppm to 2000 ppm, and especially in the range from 10 ppm to 500 ppm.

In one embodiment, one or more further stabilizers, preferably phenolic stabilizers, may be added to the liquid-crystal mixtures according to the invention in addition to the compound of the formula I or the compounds of the formula I, in order to have a further favourable effect on, or possibly even to assure, adequate stabilization against UV and thermal stress, especially against thermal stress.

In a particularly preferred embodiment, the media according to the invention comprise one or more compounds selected from the group of compounds of the formulae OH-1 to OH-6

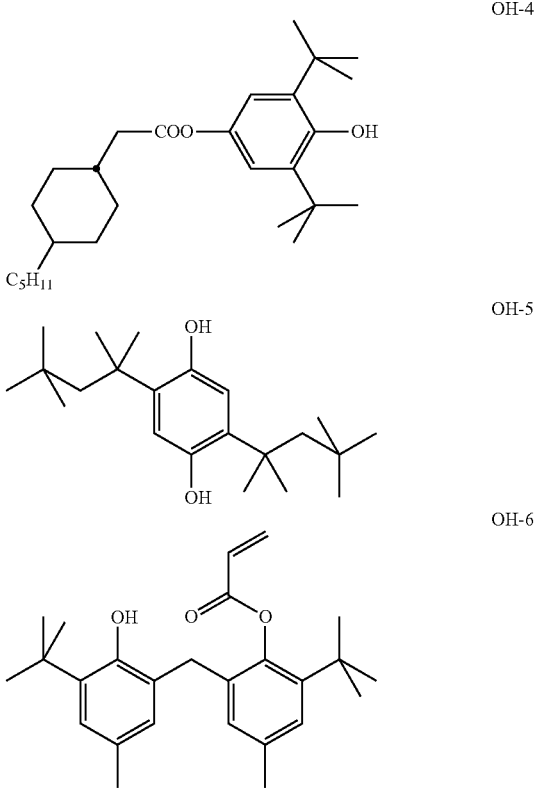

These compounds are of excellent suitability for stabilization of the media against thermal stresses.

In another preferred embodiment of the present invention, the media according to the invention may also have adequate stability when they do not comprise any phenol compound and are especially selected from the group of compounds of the formulae OH-1 to OH-6.

In the present context, moreover, a process for producing a liquid-crystalline medium is provided, in which one or more compounds of the formula I are mixed with one or more compounds of the formulae II-1 to II-4 and optionally one or more compounds of the formula III-3 and/or optionally with one or more compounds of the formula IV.

In a preferred embodiment, the liquid-crystal media according to the invention additionally comprise one or more polymerizable compounds, especially one or more polymer precursors comprising one or more reactive compounds, preferably reactive mesogens and, if required, also further additives, for example polymerization initiators and/or polymerization moderators in the customary amounts. The amount of these additives used totals 0% or more to 10% or less, based on the amount of the overall mixture, preferably 0.1% or more to 2% or less.

The concentration of these polymerizable compounds and polymer precursors is not taken into account in the specification of the concentrations and the concentration ranges of the liquid-crystal compounds in the liquid-crystal media.

The liquid-crystal media according to the invention may, if required, also comprise further additives, for example additional stabilizers and/or pleochroic dyes and/or chiral dopants in the customary amounts. The amount of these additives used preferably totals 0% or more to 10% or less, based on the amount of the overall mixture, more preferably 0.1% or more to 6% or less. The concentration of the individual compounds used is preferably 0.1% or more to 3% or less. The concentration of these and similar additives is generally not taken into account in the specification of the concentrations and the concentration ranges of the liquid-crystal compounds in the liquid-crystal media.

A further aspect of the present invention is the use of the medium according to the invention in an electrooptical display or in an electrooptical component.

The present invention also provides electrooptical displays or electrooptical components comprising liquid-crystalline media according to the invention.

Preference is given to the electrooptical displays that are driven by means of an active matrix addressing device, and especially those based on the VA effect or the ECB effect or the IPS or FFS effect. Particular preference is given to electrooptical displays, especially with active matrix addressing, that are based on the IPS or FFS effect.

According to the present invention, the elements comprise all their respective isotopes. More particularly, in the compounds, one or more H may be replaced by D, and this is also particularly preferred in some embodiments. A correspondingly high deuteration level of the corresponding compounds enables, for example, detection and recognition of the compounds. This is very helpful in some cases especially for the compounds of the formula I.

According to the present invention, the following terms have the following meanings:

alkyl more preferably straight-chain alkyl, especially $CH_3—$, $C_2H_5—$, $n-C_3H_7$, $n-C_4H_9$- or $n-C_5H_{11}—$, alkenyl more preferably $CH_2=CH—$, $E-CH_3—CH=CH—$, $CH_2=CH—CH_2—CH_2—$, $E-CH_3—CH=CH—CH_2—CH_2—$ or $E-(n-C_3H_7)—CH=CH—$, and alkoxy more preferably straight-chain alkoxy, especially $CH_3O—$, $C_2H_5O—$, $n-C_3H_7O—$, $n-C_4H_9O—$ or $n-C_5H_{11}O—$.

In respect of the present invention, in connection with the specification of the constituents of the compositions, unless stated otherwise in the individual case:

"comprise": the concentration of the constituents in question in the composition is preferably 5% or more, more preferably 10% or more and most preferably 20% or more, "predominantly consisting of": the concentration of the constituents in question in the composition is preferably 50% or more, more preferably 55% or more and most preferably 60% or more, "essentially consisting of": the concentration of the constituents in question in the composition is preferably 80% or more, more preferably 90% or more and most preferably 95% or more, and "virtually entirely consisting of": the concentration of the constituents in question in the composition is preferably 98% or more, more preferably 99% or more and most preferably 100.0%.

This applies both to the media as compositions with their constituents, which may be components and compounds, and to the components with their constituents, the compounds. Only in relation to the concentration of a single compound in relation to the overall medium does the term "comprise" mean that the concentration of the compound in question is preferably 1% or more, more preferably 2% or more, most preferably 4% or more.

In respect of the present invention, "≤" means not more than, preferably less than, and "≥" means not less than, preferably greater than.

In respect of the present invention,

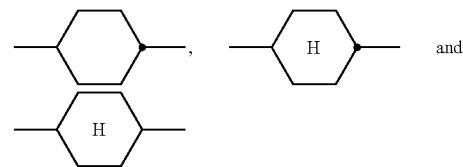

mean trans-1,4-cyclohexylene and

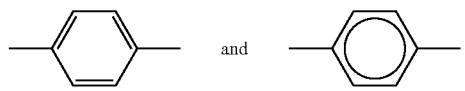

mean 1,4-phenylene.

In respect of the present invention, the term "dielectrically positive compounds" means those compounds having a $\Delta\epsilon>1.5$, "dielectrically uncharged compounds" those having $-1.5\leq\Delta\epsilon\leq1.5$, and "dielectrically negative" compounds those having $\Delta\epsilon<-1.5$. In this case, the dielectric anisotropy of the compounds is determined by dissolving 10% of the compounds in a liquid-crystalline host and determining the capacitance of the resulting mixture in at least one test cell in each case having layer thickness 20 μm with homeotropic and homogeneous surface orientation at 1 kHz. The measurement voltage is typically 0.5 V to 1.0 V, but it is always lower than the capacitative threshold of the respective liquid crystal mixture under examination.

The host mixture used for dielectrically positive and dielectrically uncharged compounds is ZLI-4792, and that used for dielectrically negative compounds is ZLI-2857, both from Merck KGaA, Germany. The change in the dielectric constant of the host mixture after addition of the compound to be examined and extrapolation to 100% of the compounds used are used to obtain the values for the particular compounds to be examined. The compound to be examined is dissolved in a concentration of 10% in the host mixture. If the solubility of the substance is too low for this, the concentration is halved stepwise until the study can be effected at the desired temperature.

The compositions consist of two or more compounds, preferably of 3 or more to 30 or fewer, more preferably of 6 or more to 20 or fewer and most preferably of 10 or more to 16 or fewer compounds that are mixed in a conventional manner. In general, the desired amount of the components used in a smaller amount is dissolved in the components that make up the main constituent of the mixture. This is appropriately effected at elevated temperature. If the temperature chosen is above the clearing point of the main constituent, the completion of the dissolution operation can be observed particularly easily. However, it is also possible to produce the liquid crystal mixtures in other customary ways, for example using preliminary mixtures or from what is called a "multi-bottle system".

The mixtures according to the invention exhibit very broad nematic phase regions, preferably with clearing points of 65° C. or more, very favourable values for the capacitative threshold, relatively high values for the holding ratio and simultaneously very good low-temperature stabilities at −30° C. and −40° C. In addition, the mixtures according to the invention feature low rotational viscosities $\gamma_1$.

It will be self-evident to the person skilled in the art that the media according to the invention for use in VA, IPS, FFS or PALC displays may also comprise compounds in which, for example, H, N, O, Cl, F are replaced by the corresponding isotopes.

The construction of the liquid crystal displays according to the invention corresponds to the standard geometries as described, for example, in EP 0 240 379 A1.

By means of suitable additives, it is possible to modify the liquid crystal phases according to the invention such that they are usable in any kind of ECB, VAN, IPS, FFS, GH or ASM-VA LCD display, for example, that has become known to date.

Table E below specifies possible dopants which can generally be added to the mixtures according to the invention. If the mixtures comprise one or more dopants, it is used in amounts of 0.01% to 4%, preferably 0.1% to 1.0%.

Additional stabilizers which may be added, for example, to the mixtures according to the invention, preferably in amounts of 0.01% to 6%, especially 0.1% to 3%, are specified below in Table F.

For the purposes of the present invention, all concentrations, unless explicitly noted otherwise, are stated in percent by mass and relate to the corresponding mixture or mixture component, unless explicitly stated otherwise.

According to the present invention, all the values specified for temperatures, for example the melting point $T(C,N)$, the transition from the smectic (S) to the nematic (N) phase $T(S,N)$ and the clearing point $T(N,I)$, are reported in degrees Celsius (° C.), and all temperature differentials are correspondingly reported as degrees of difference (° or degrees), unless explicitly stated otherwise.

The term "threshold voltage" in respect of the present invention relates to the capacitative threshold ($V_0$), also called the Fréedericksz threshold, unless explicitly stated otherwise.

All physical properties are and were determined according to "Merck Liquid Crystals, Physical Properties of Liquid Crystals", Status November 1997, Merck KGaA, Germany and apply to a temperature of 20° C., and $\Delta n$ is determined at 589 nm and $\Delta \varepsilon$ at 1 kHz, unless explicitly stated otherwise in each case.

The electrooptical properties, for example the threshold voltage ($V_0$) (capacitative measurement), and likewise the switching characteristics, are determined in test cells manufactured by Merck Japan. These test cells have substrates composed of soda-lime glass and are designed in an ECB or VA configuration with polyimide alignment layers (SE-1211 with **26 diluent (mixing ratio 1:1), both from Nissan Chemicals, Japan), which are rubbed at right angles to one another and bring about a homeotropic orientation of the liquid crystals. The area of the transparent, virtually square electrodes composed of ITO is 1 cm$^2$.

The liquid-crystal mixtures used, unless stated otherwise, have not been admixed with a chiral dopant, but they are also particularly suitable for applications where such a doping is required.

The VHR is determined in test cells produced by Merck Japan. The test cells have substrates composed of soda-lime glass and have been provided with polyimide alignment layers having a layer thickness of 50 nm. The cell gap is a uniform 6.5 µm. The area of the transparent electrodes composed of ITO is 1 cm$^2$.

Unless stated otherwise, the VHR is determined at 20° C. (VHR$_{20}$) and after 5 minutes in an oven at 100° C. (VHR$_{100}$) in a commercially available instrument from Autronic Melchers, Germany. The voltage used has a frequency within a range from 1 Hz to 60 Hz, unless stated more precisely.

The accuracy of the measurements of the VHR depends on the particular value of the VHR. The accuracy decreases with decreasing values. The deviations that are generally observed at values in the different size ranges are compiled in terms of their order of magnitude in the table which follows.

| VHR range VHR values | | Deviation (relative) $\Delta_G$VHR/VHR/% |
|---|---|---|
| from | to | about |
| 99.6% | 100% | +/−0.1 |
| 99.0% | 99.6% | +/−0.2 |
| 98% | 99% | +/−0.3 |
| 95% | 98% | +/−0.5 |
| 90% | 95% | +/−1 |
| 80% | 90% | +/−2 |
| 60% | 80% | +/−4 |
| 40% | 60% | +/−8 |
| 20% | 40% | +/−10 |
| 10% | 20% | +/−20 |

Stability against irradiation with UV is examined in a commercial "Suntest CPS" instrument from Heraeus, Germany. This involves irradiating the sealed test cells without additional thermal stress for between 30 min and 2.0 hours, if not stated explicitly. The irradiation output in the wavelength range from 300 nm to 800 nm is 765 W/m$^2$, if not stated explicitly. A UV cut-off filter having a cut-off wavelength of 310 nm is used to simulate "window glass mode". In each test series, for every condition, at least four test cells are examined and the respective results are reported as mean values of the corresponding individual measurements.

The decrease in the voltage holding ratio ($\Delta$VHR) which is typically caused by the stress, for example by irradiation with UV by LCD backlighting, is determined by the following equation (1):

$$\Delta VHR(t) = VHR(t) - VHR(t=0) \tag{1}$$

The rotational viscosity is determined by the rotating permanent magnet method, and the flow viscosity in a modified Ubbelohde viscometer. For the liquid crystal mixtures ZLI-2293, ZLI-4792 and MLC-6608, all products from Merck KGaA, Darmstadt, Germany, the values of rotational viscosity determined at 20° C. are 161 mPa·s, 133 mPa·s and 186 mPa·s respectively, and the flow viscosity (v) values 21 mm$^2$·s$^{-1}$, 14 mm$^2$·s$^{-1}$ and 27 mm$^2$·s$^{-1}$ respectively.

Unless explicitly stated otherwise, the following symbols are used:

$V_o$ threshold voltage, capacitative [V] at 20° C.,
$n_e$ extraordinary refractive index measured at 20° C. and 589 nm,
$n_o$ ordinary refractive index measured at 20° C. and 589 nm,
$\Delta n$ optical anisotropy measured at 20° C. and 589 nm,
$\varepsilon_\perp$ dielectric susceptibility at right angles to the director at 20° C. and 1 kHz,
$\varepsilon_\parallel$ dielectric susceptibility parallel to the director at 20° C. and 1 kHz,
$\Delta\varepsilon$ dielectric anisotropy at 20° C. and 1 kHz,
cp. or $T(N,I)$ clearing point [° C.],
v flow viscosity measured at 20° C. [mm$^2$·s$^{-1}$],
$\gamma_1$ rotational viscosity measured at 20° C. [mPa·s],
$K_1$ elastic constant, "splay" deformation at 20° C. [pN],
$K_2$ elastic constant, "twist" deformation at 20° C. [pN],
$K_3$ elastic constant, "bend" deformation at 20° C. [pN],
LTS low-temperature stability of the phase, determined in test cells, VHR voltage holding ratio,
ΔVHR decrease in the voltage holding ratio and
$S_{rel}$ relative stability of the VHR.

The examples which follow illustrate the present invention without restricting it. However, they show the person skilled in the art preferred mixing concepts with compounds usable with preference and the respective concentrations thereof, and the combinations thereof with one another. Moreover, the examples illustrate which properties and combinations of properties are obtainable.

In respect of the present invention and in the examples which follow, the structures of the liquid-crystal compounds are stated in the form of acronyms that are transformed into chemical formulae according to Tables A to C below. All $C_nH_{2n+1}$, $C_mH_{2m+1}$ and $C_lH_{2l+1}$ or $C_nH_{2n}$, $C_mH_{2m}$ and $C_lH_{2l}$ radicals are straight-chain alkyl radicals or alkylene radicals respectively having n, m and l carbon atoms, where m, n and l are each independently an integer, preferably 1 to 6. Table A gives the codes for the ring elements of the cycles in the compound, Table B lists the bridging elements, and Table C lists the meanings of the symbols for the left-hand and right-hand end groups of the molecules. The acronyms are composed of the codes for the ring elements with optional linking groups, followed by a first hyphen and the codes for the left-hand end group, and a second hyphen and the codes for the right-hand end group. Table D collates example structures of compounds with their respective abbreviations.

TABLE A

Ring elements

TABLE A-continued
| | Ring elements | | |
|---|---|---|---|
| n3f | 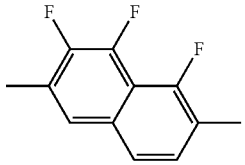 | nN3fI | 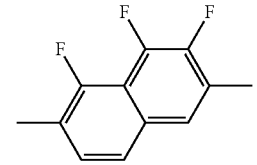 |
| th | 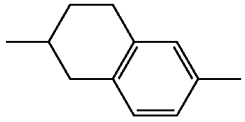 | thI | 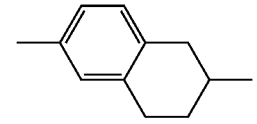 |
| tH2f | 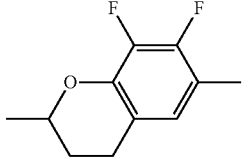 | tH2fI | 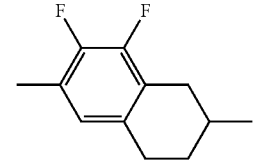 |
| o2f | 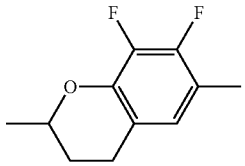 | o2fI | 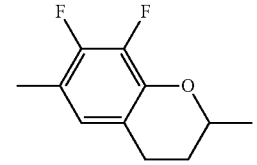 |
| dh | 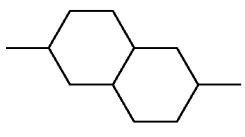 | B | 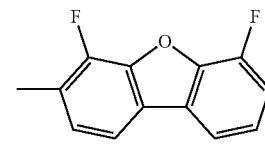 |
| | | B(S) | 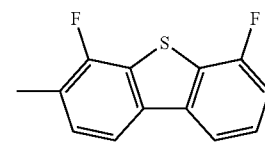 |
| K |  | KI | 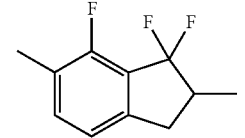 |
| L | 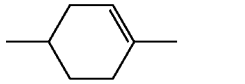 | LI |  |
| F | 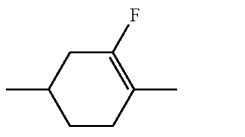 | FI | 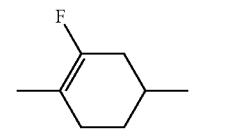 |

TABLE B

| | Bridging elements | |
|---|---|---|
| E | —CH$_2$—CH$_2$— | |
| V | —CH=CH— | |
| T | —C≡C— | |
| W | —CF$_2$—CF$_2$— | |
| B | —CF=CF— | |

TABLE B-continued

| | Bridging elements | | | |
|---|---|---|---|---|
| Z | —CO—O— | ZI | —O—CO— |
| X | —CF=CH— | XI | —CH=CF— |
| O | —CH$_2$—O— | OI | —O—CH$_2$— |
| Q | —CF$_2$—O— | QI | —O—CF$_2$— |

TABLE C

End groups

| Left-hand end, individually or in combination | | Right-hand end, individually or in combination | |
|---|---|---|---|
| -n- | C$_n$H$_{2n+1}$— | -n | —C$_n$H$_{2n+1}$ |
| -nO- | C$_n$H$_{2n+1}$—O— | -nO | —O—C$_n$H$_{2n+1}$ |
| -V- | CH$_2$=CH— | -V | —CH=CH$_2$ |
| -nV- | C$_n$H$_{2n+1}$—CH=CH— | -nV | —C$_n$H$_{2n}$—CH=CH$_2$ |
| -Vn- | CH$_2$=CH—C$_n$H$_{2n}$— | -Vn | —CH=CH—C$_n$H$_{2n+1}$ |
| -nVm- | C$_n$H$_{2n+1}$—CH=CH—C$_m$H$_{2m}$— | -nVm | —C$_n$H$_{2n}$—CH=CH—C$_m$H$_{2m+1}$ |
| -N- | N≡C— | -N | —C≡N |
| -S- | S=C=N— | -S | —N=C=S |
| -F- | F— | -F | —F |
| -Cl- | Cl— | -Cl | —Cl |
| -M- | CFH$_2$— | -M | —CFH$_2$ |
| -D- | CF$_2$H— | -D | —CF$_2$H |
| -T- | CF$_3$— | -T | —CF$_3$ |
| -MO- | CFH$_2$O— | -OM | —OCFH$_2$ |
| -DO- | CF$_2$HO— | -OD | —OCF$_2$H |
| -TO- | CF$_3$O— | -OT | —OCF$_3$ |
| -A- | H—C≡C— | -A | —C≡C—H |
| -nA- | C$_n$H$_{2n+1}$—C≡C— | -An | —C≡C—C$_n$H$_{2n+1}$ |
| -NA- | N≡C—C≡C— | -AN | —C≡C—C≡N |

| Left-hand end, in combination only | | Right-hand end, in combination only | |
|---|---|---|---|
| -...n...- | —C$_n$H$_{2n}$— | -...n... | —C$_n$H$_{2n}$— |
| -...M...- | —CFH— | -...M... | —CFH— |
| -...D...- | —CF$_2$— | -...D... | —CF$_2$— |
| -...V...- | —CH=CH— | -...V... | —CH=CH— |
| -...Z...- | —CO—O— | -...Z... | —CO—O— |
| -...ZI...- | —O—CO— | -...ZI... | —O—CO— |
| -...K...- | —CO— | -...K... | —CO— |
| -...W...- | —CF=CF— | -...W... | —CF=CF— | in which n and m are each integers and the three dots "..." are placeholders for other abbreviations from this table.

Preferably, the mixtures according to the invention comprise, as well as the compounds of the formula I, one or more compounds from the compounds specified below.

In this context, n, m and l are each independently an integer, preferably 1 to 6.

TABLE D

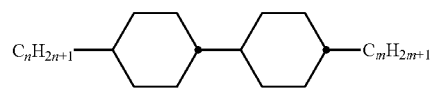

CC-n-m

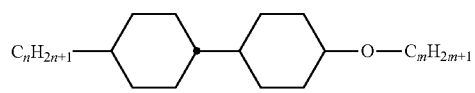

CC-n-Om

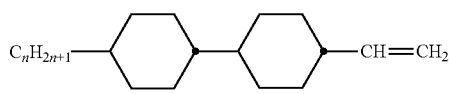

TABLE D-continued
CC-n-V
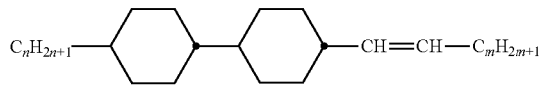
CC-n-Vm
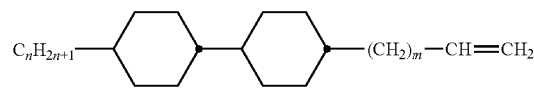
CC-n-mV
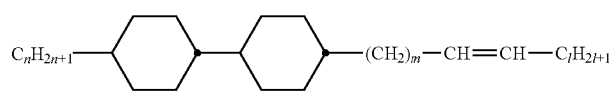
CC-n-mVl
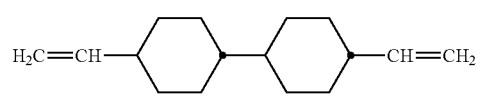
CC-V-V
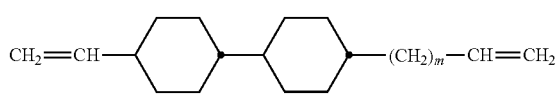
CC-V-mV
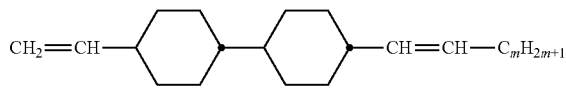
CC-V-Vm
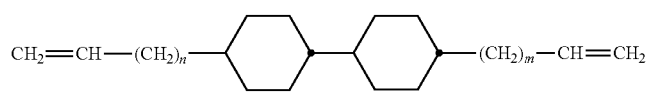
CC-Vn-mV
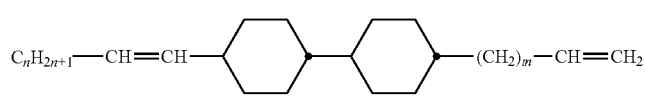
CC-nV-mV
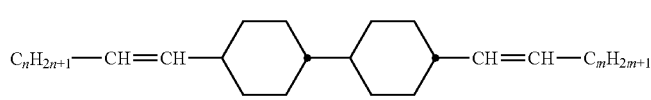
CC-nV-Vm
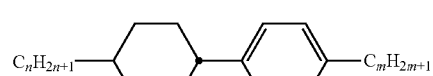
CP-n-m
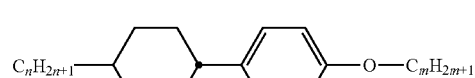
CP-n-Om TABLE D-continued
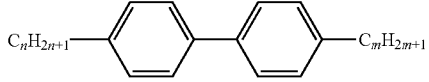
PP-n-m
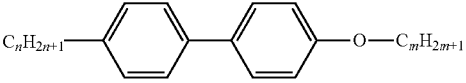
PP-n-Om
CCP-n-m
CCP-n-Om
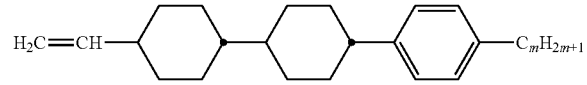
CCP-V-m
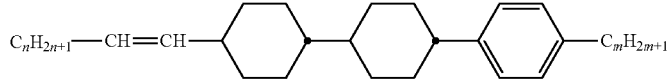
CCP-nV-m
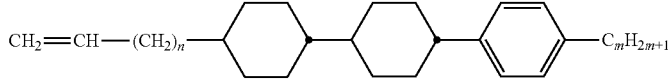
CCP-Vn-m
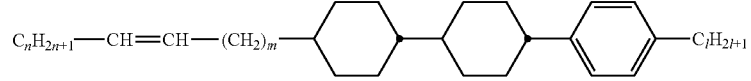
CCP-nVm-l
CPP-n-m
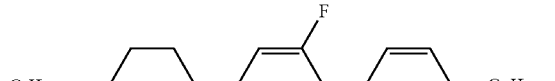
CGP-n-m
PGP-n-m TABLE D-continued
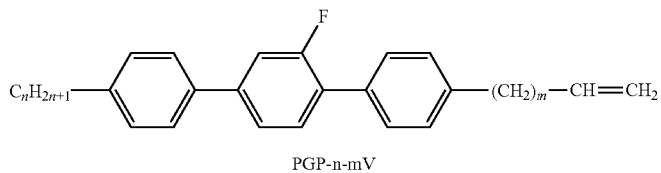
PGP-n-mV
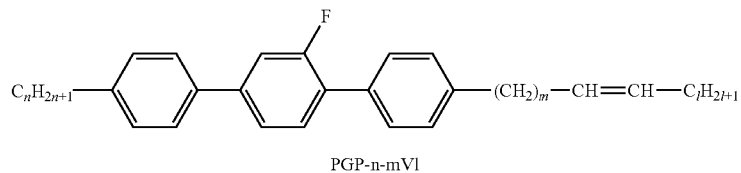
PGP-n-mVl
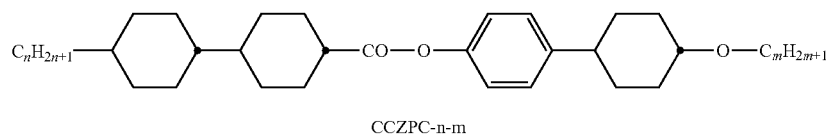
CCZPC-n-m
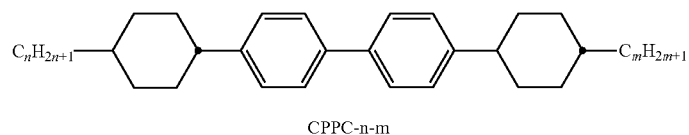
CPPC-n-m
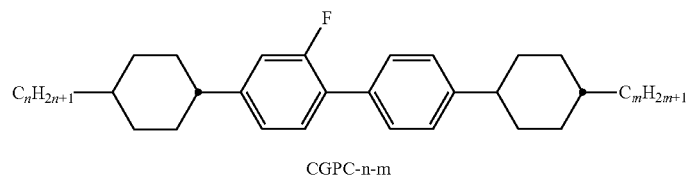
CGPC-n-m
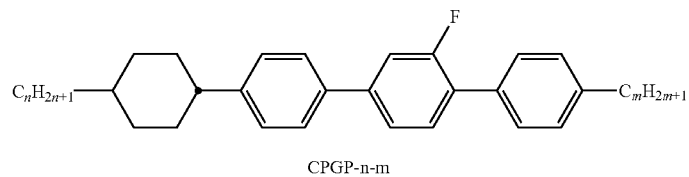
CPGP-n-m
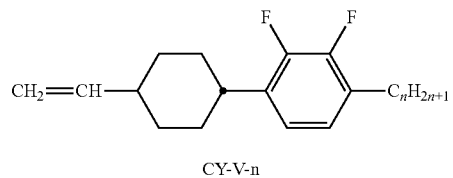
CY-V-n
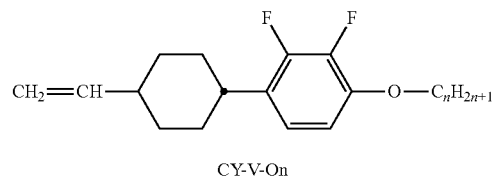
CY-V-On
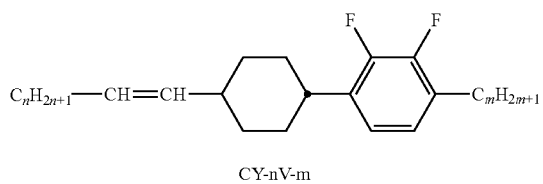
CY-nV-m TABLE D-continued
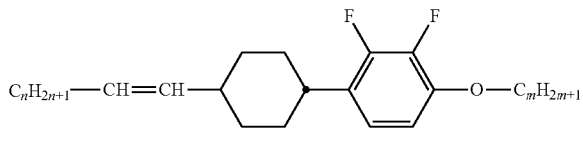
CY-nV-Om
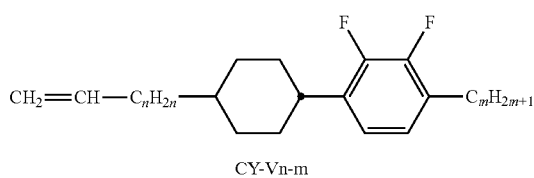
CY-Vn-m
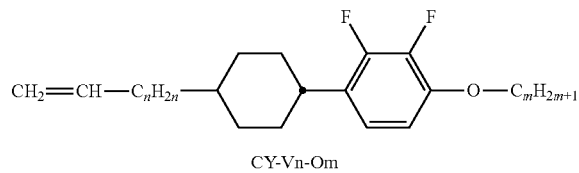
CY-Vn-Om
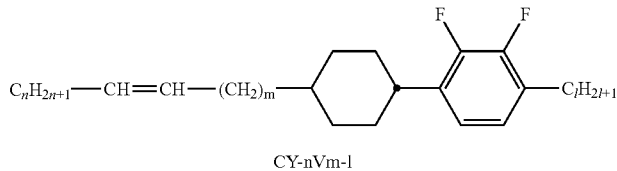
CY-nVm-l
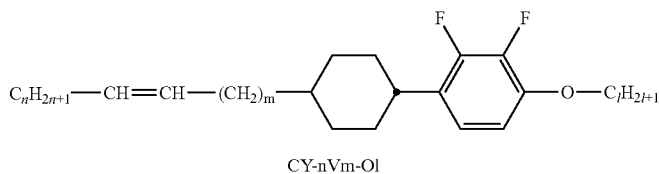
CY-nVm-Ol
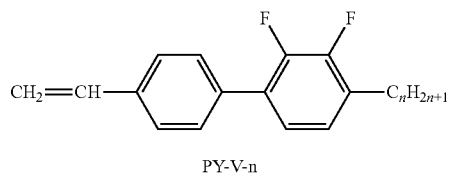
PY-V-n
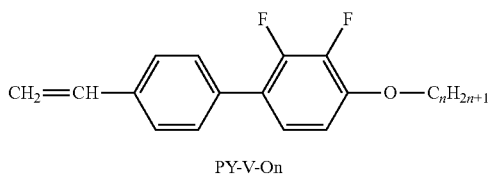
PY-V-On
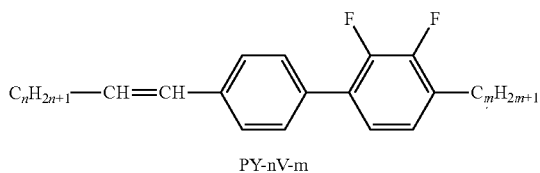
PY-nV-m
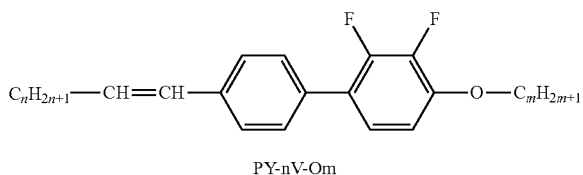
PY-nV-Om TABLE D-continued
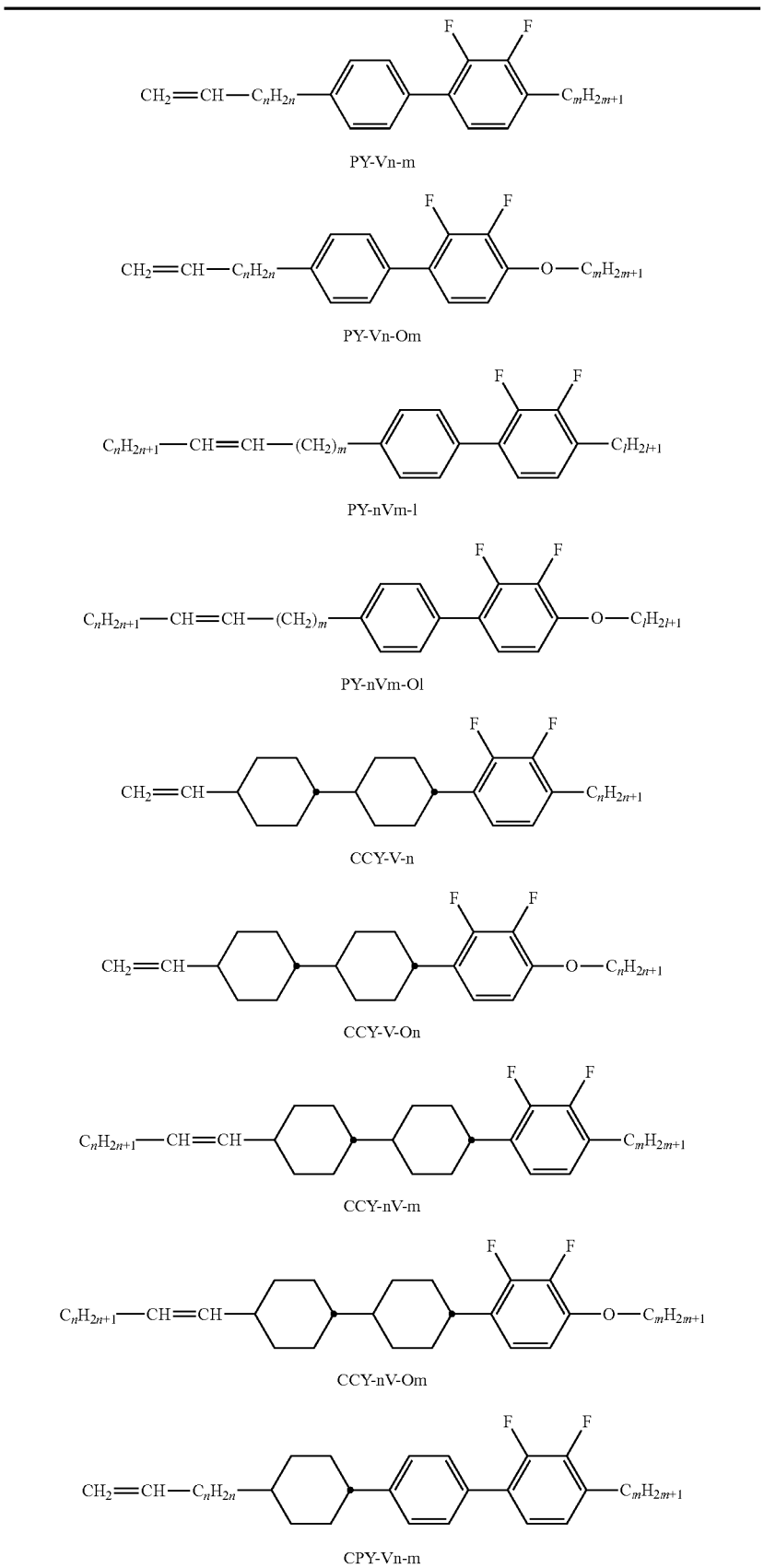

TABLE D-continued
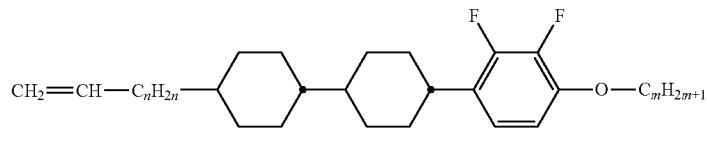
CCY-Vn-Om
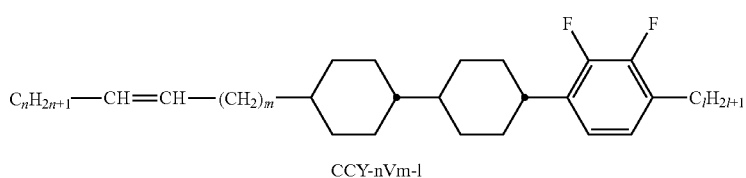
CCY-nVm-l
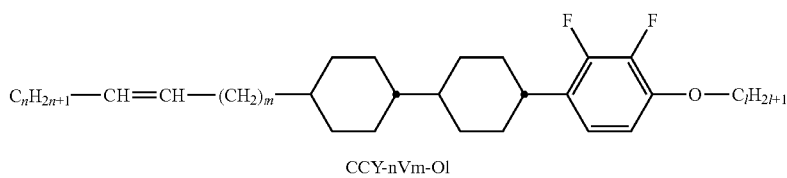
CCY-nVm-Ol
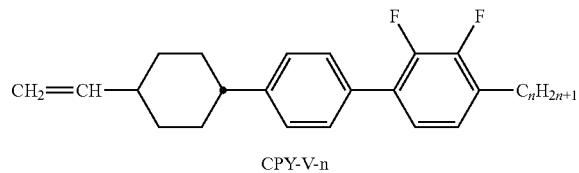
CPY-V-n
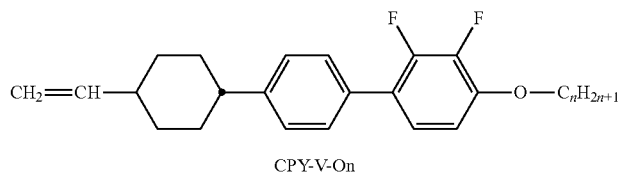
CPY-V-On
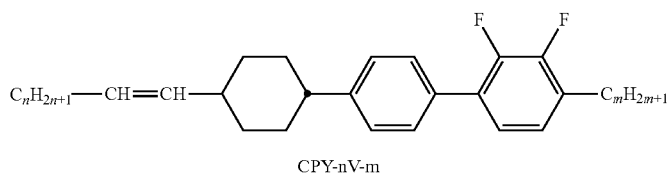
CPY-nV-m
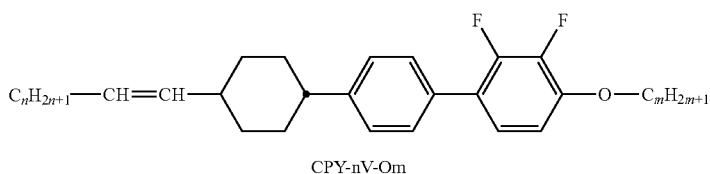
CPY-nV-Om
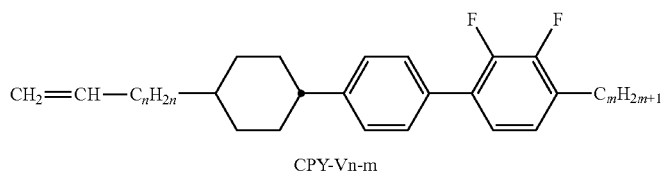
CPY-Vn-m
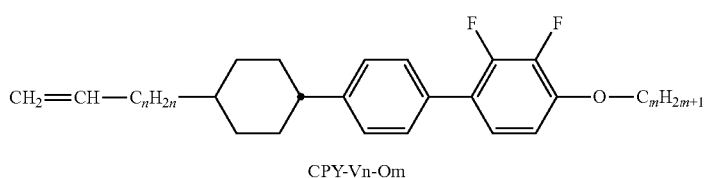
CPY-Vn-Om TABLE D-continued
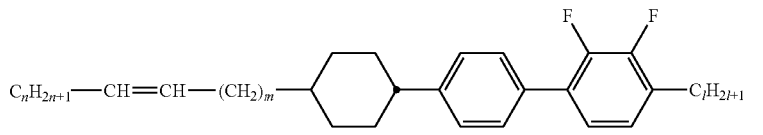
CPY-nVm-l
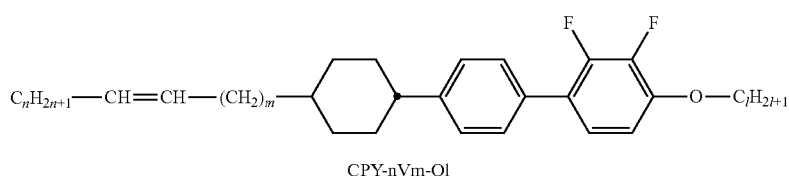
CPY-nVm-Ol
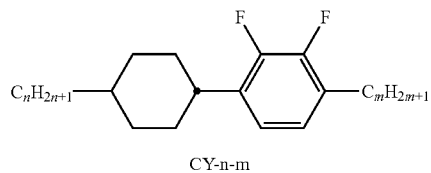
CY-n-m
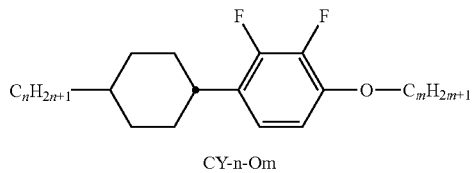
CY-n-Om
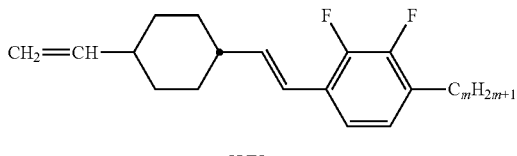
CVY-n-m
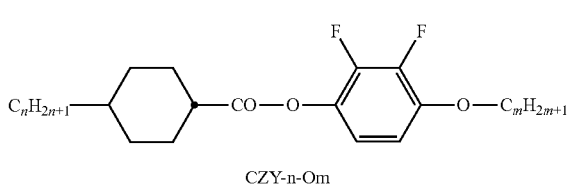
CZY-n-Om
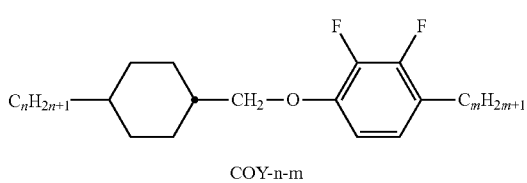
COY-n-m
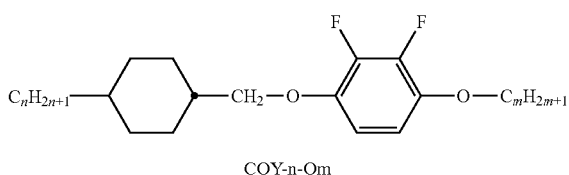
COY-n-Om
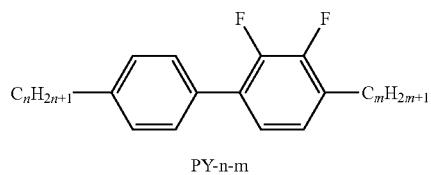
PY-n-m TABLE D-continued
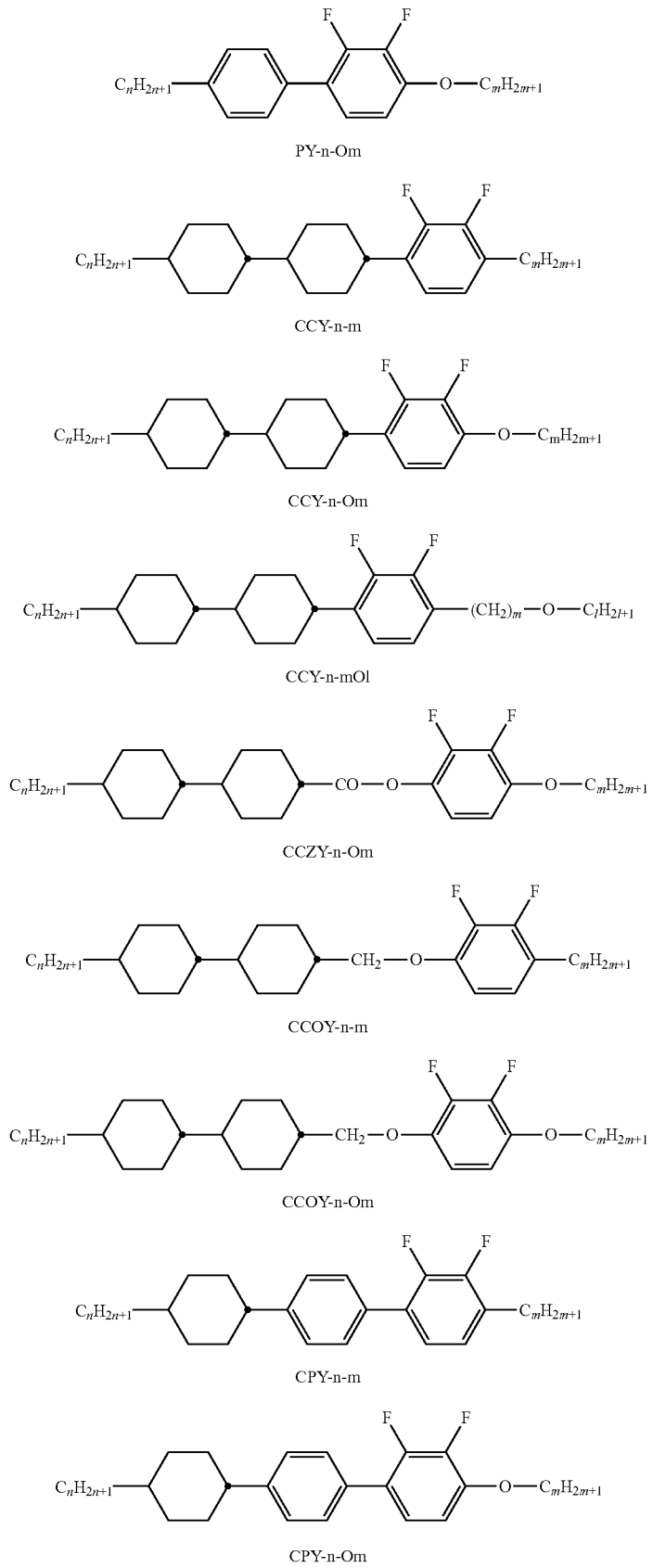

TABLE D-continued
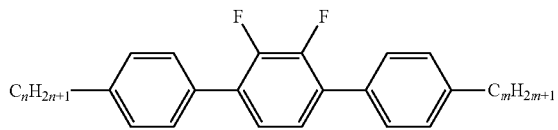
PYP-n-m
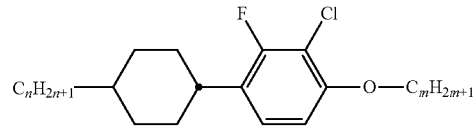
CP(F,Cl)-n-Om
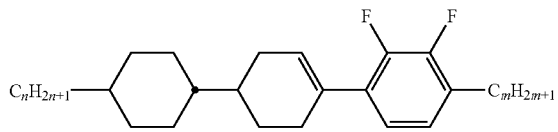
CLY-n-m
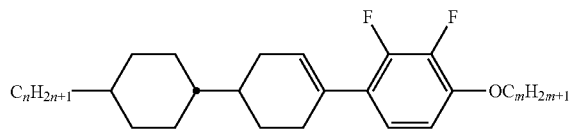
CLY-n-Om
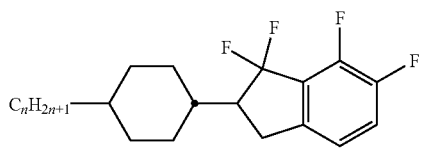
CK-n-F
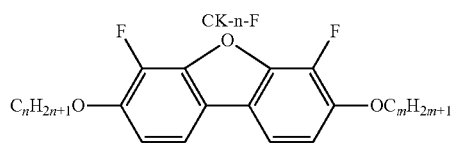
B-nO-Om
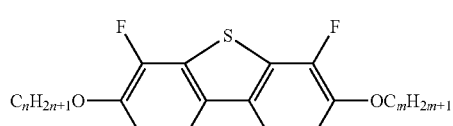
B(S)-nO-Om
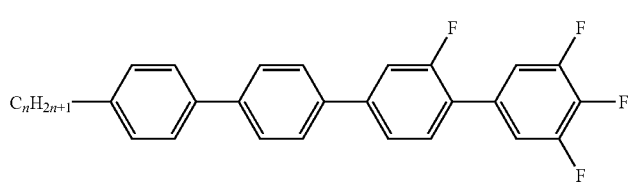
PPGU-n-F
BCH-nm Table E specifies chiral dopants that are used with preference in the mixtures according to the invention.
TABLE E
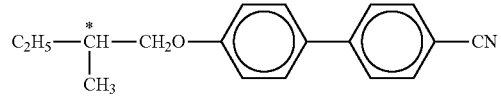
C 15
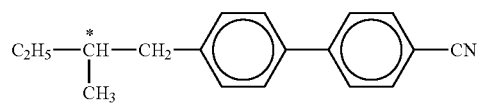
CB 15
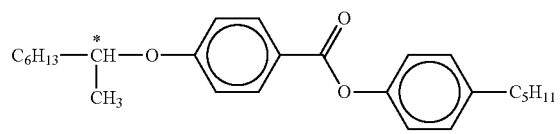
CM 21
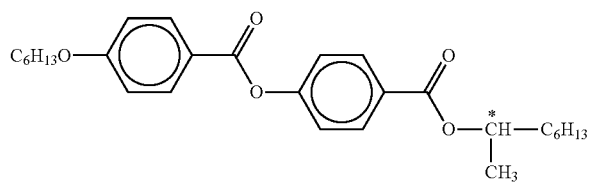
R S-811 / S-811
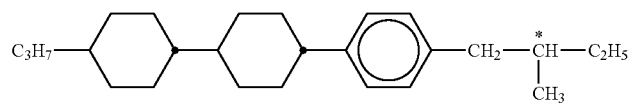
CM 44
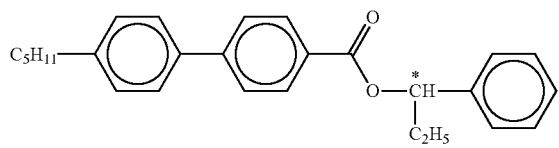
CM 45
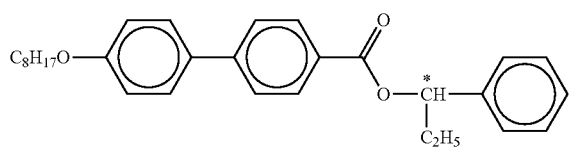
CM 47
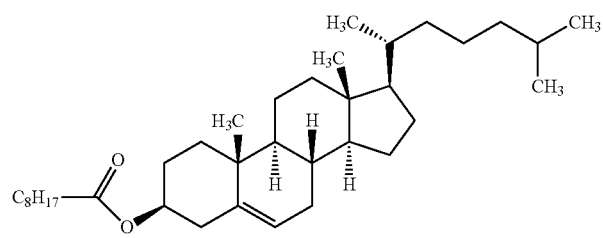
CN TABLE E-continued

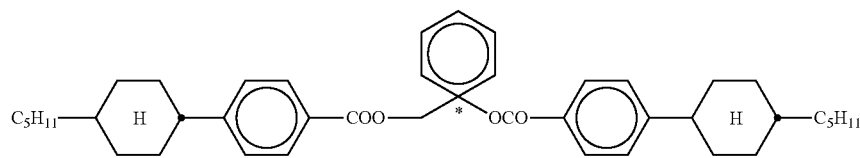

R-1011 / S-1011

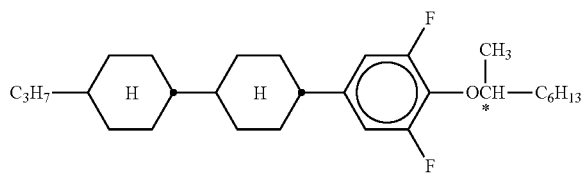

R-2011 / S-2011

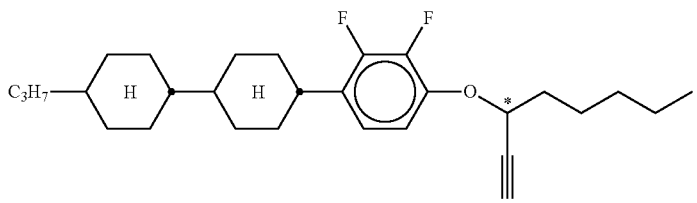

R-3011 / S-3011

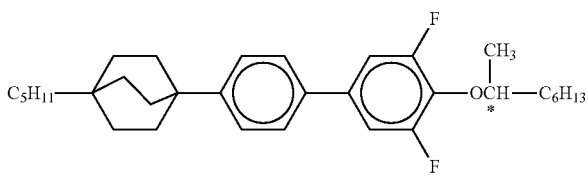

R-4011 / S-4011

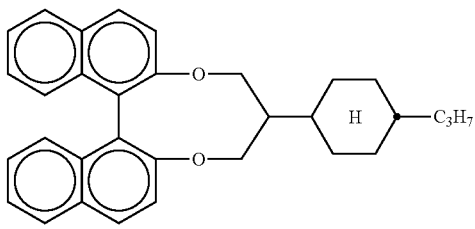

R-5011 / S-5011

In a preferred embodiment of the present invention, the media according to the invention comprise one or more compounds selected from the group of the compounds from Table E.

Table F below specifies stabilizers which can be used in the mixtures according to the invention in addition to the compounds of the formula I. In this context, n is an integer in the range from 1 to 12. The phenol derivatives shown in particular are particularly advantageously usable as additional stabilizers, especially as antioxidants.

TABLE F
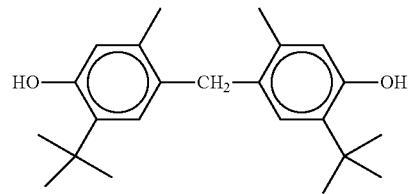
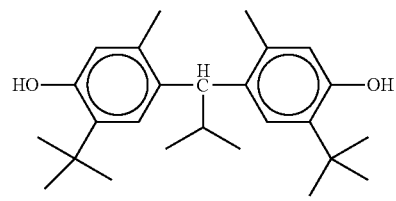
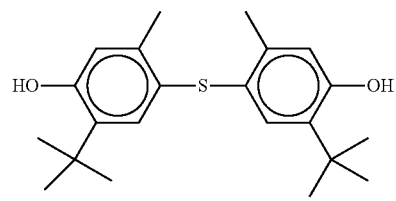
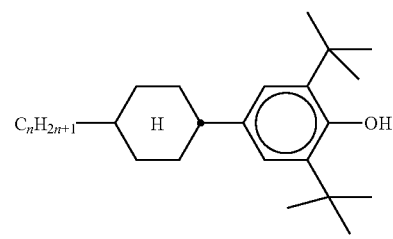
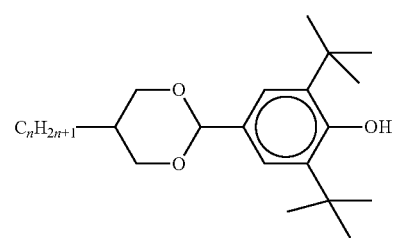
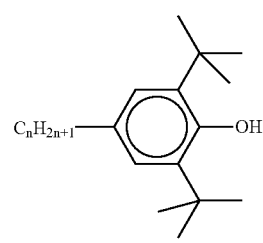
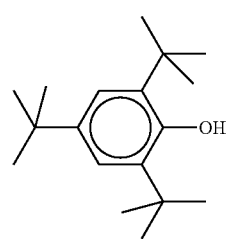

TABLE F-continued
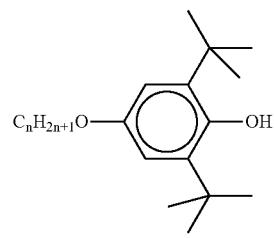
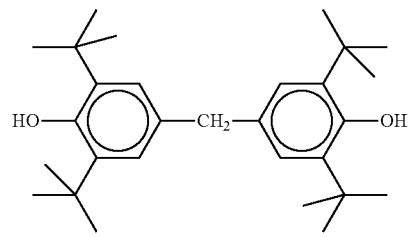
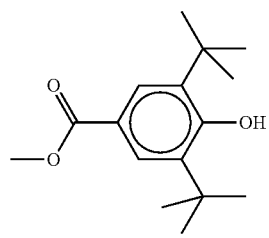
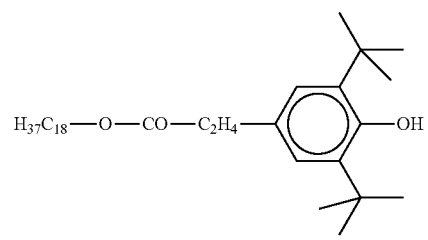
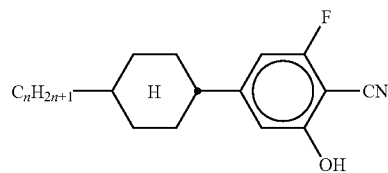
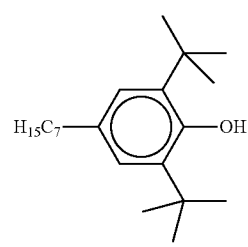
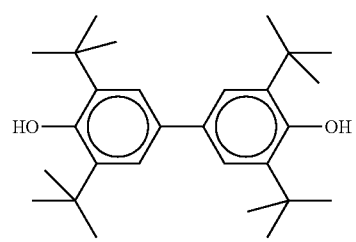

TABLE F-continued
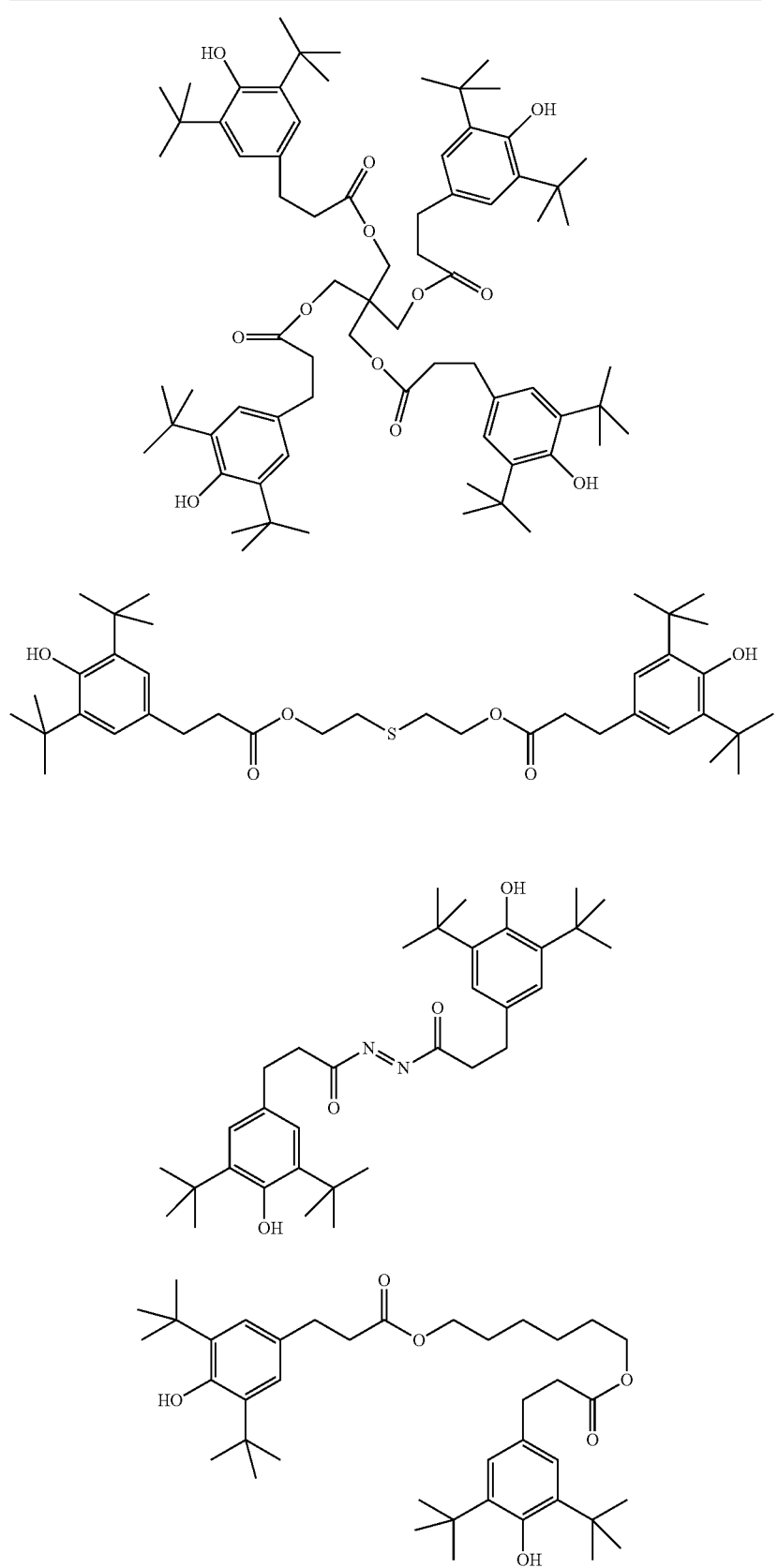

TABLE F-continued
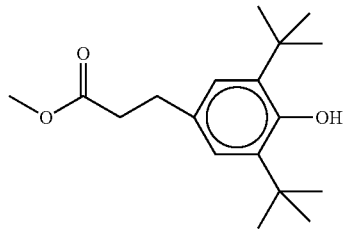
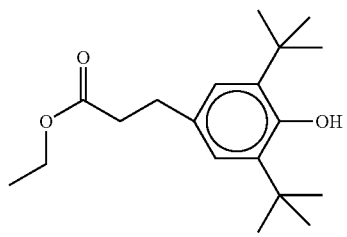
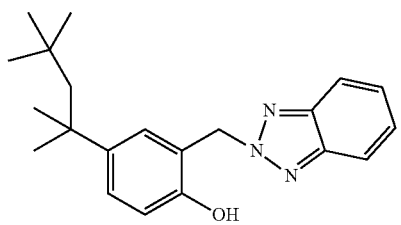 [SMILES: CC(C)(C)CC(C)(C)c1ccc(O)c(Cn2nc3ccccc3n2)c1]
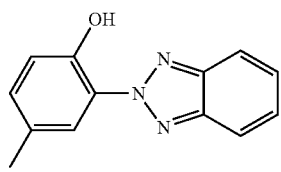 [SMILES: Cc1ccc(O)c(-n2nc3ccccc3n2)c1]
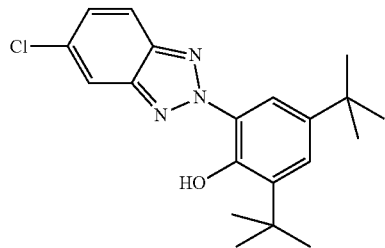 [SMILES: CC(C)(C)c1cc(-n2nc3ccc(Cl)cc3n2)c(O)c(C(C)(C)C)c1]
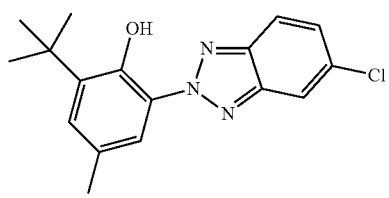 [SMILES: Cc1cc(-n2nc3ccc(Cl)cc3n2)c(O)c(C(C)(C)C)c1]

TABLE F-continued
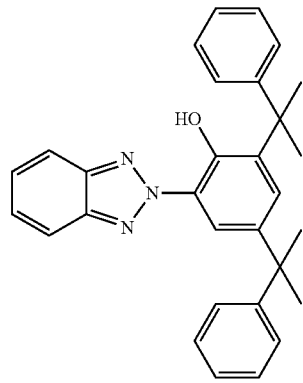 [SMILES: CC(C)(c1ccccc1)c1cc(-n2nc3ccccc3n2)c(O)c(C(C)(C)c2ccccc2)c1]
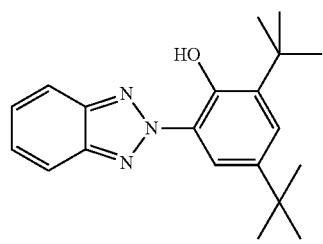 [SMILES: CC(C)(C)c1cc(-n2nc3ccccc3n2)c(O)c(C(C)(C)C)c1]
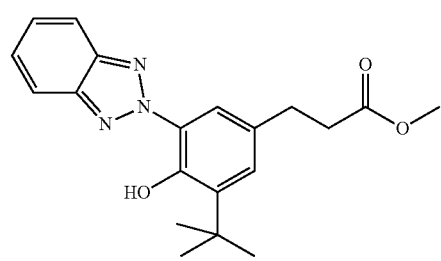 [SMILES: COC(=O)CCc1cc(-n2nc3ccccc3n2)c(O)c(C(C)(C)C)c1]
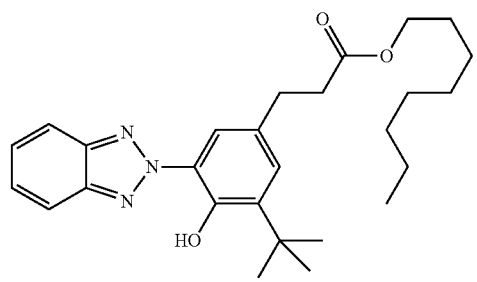 [SMILES: CCCCCCCCOC(=O)CCc1cc(-n2nc3ccccc3n2)c(O)c(C(C)(C)C)c1]

TABLE F-continued
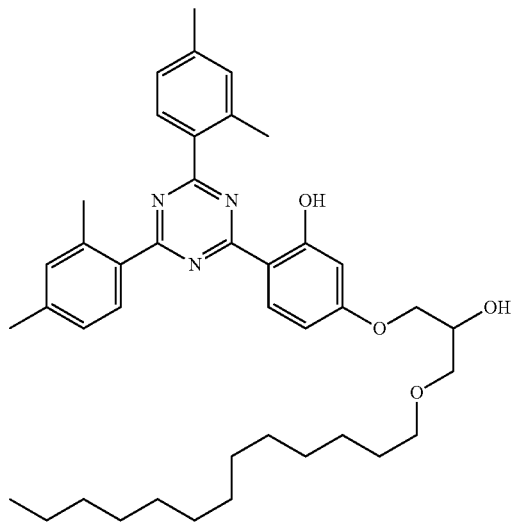 [SMILES: CCCCCCCCCCCCCOCC(O)COc1ccc(-c2nc(-c3ccc(C)cc3C)nc(-c3ccc(C)cc3C)n2)c(O)c1]
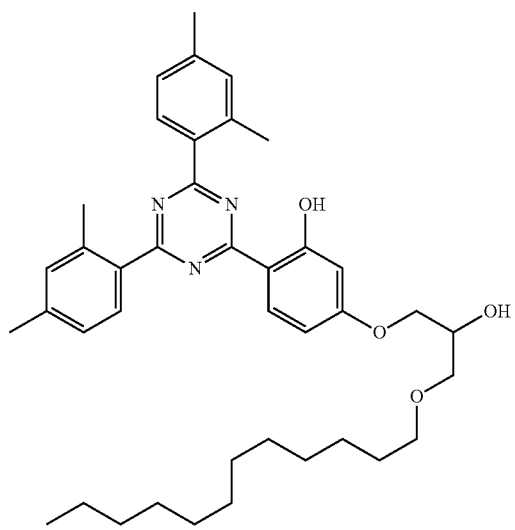 [SMILES: CCCCCCCCCCCCOCC(O)COc1ccc(-c2nc(-c3ccc(C)cc3C)nc(-c3ccc(C)cc3C)n2)c(O)c1]
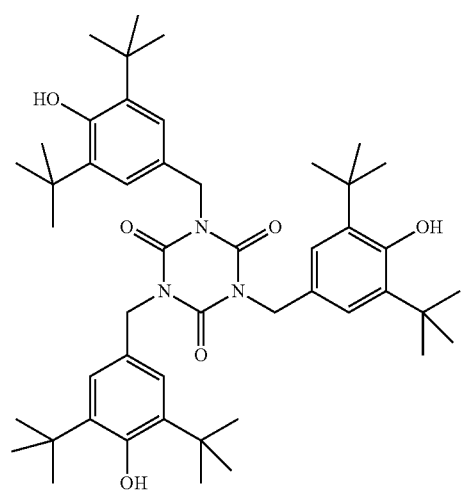 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]

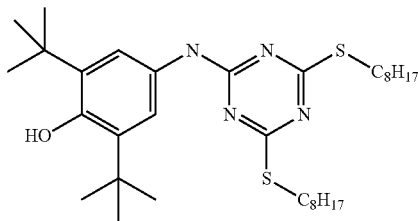

In a preferred embodiment of the present invention, the media according to the invention comprise one or more compounds selected from the group of compounds from Table F, especially one or more compounds selected from the group of compounds of the two formulae

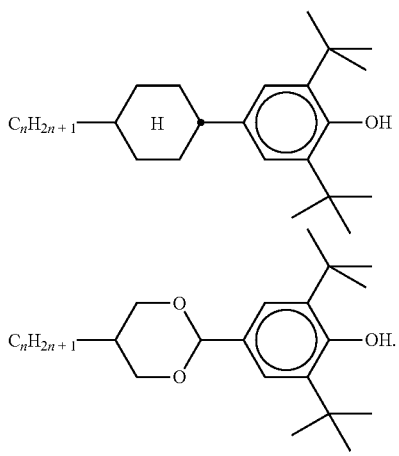

EXAMPLES AND COMPARATIVE EXAMPLES

The examples which follow elucidate the present invention without restricting it in any way. However, it will be clear to the person skilled in the art which properties are achievable and in which areas they are modifiable. More particularly, the various properties and combinations thereof that can preferably be achieved are thus illustrated.

SYNTHESIS EXAMPLES

Synthesis Example I-1

Synthesis of 4-[3-(2-ethyl-4-{3-[(2,2,6,6-tetramethylpiperidin-4-yl)oxy]propyl}phenyl)propoxy]-2,2,6,6-tetramethylpiperidine (Compound of the Formula I-1)

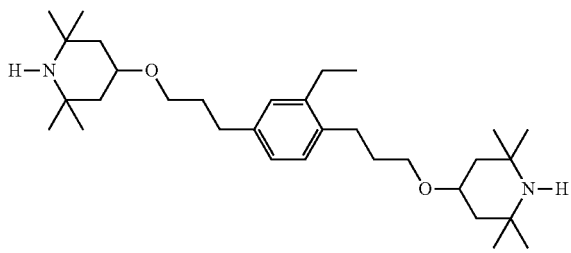

i) Synthesis of 3[3-ethyl-4-(3-hydroxypropyl)phenyl]propan-1-ol (2)

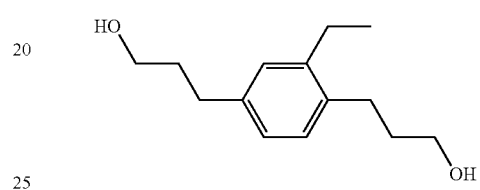

11.0 g (103.8 mmol) of sodium carbonate are initially charged in 50 ml of water. 10.0 g (32.2 mmol) of 4-bromo-2-ethyl-1-iodobenzene, 15.0 g (105.6 mmol) of 2-butoxy-[1,2]oxaborolane and 0.50 ml (3.67 mmol) of triethylamine are dissolved in 250 ml of tetrahydrofuran and added to the reaction solution and degassed under an argon stream for 40 min. Then 170 mg (0.96 mmol) of palladium(II) chloride (59% Pd, anhydrous) and 0.90 g (1.92 mmol) of 2-dicyclohexylphosphino-2,6-diisopropoxy-1,1-biphenyl are added and the mixture is stirred under reflux for 18 h. On completion of conversion, the reaction mixture is cooled down to room temperature and admixed with water and methyl tert-butyl ether (MtBE), and the phases are separated. The aqueous phase is extracted with MtBE, and the combined organic phases are washed with saturated sodium chloride solution, dried over sodium sulphate, filtered and concentrated under reduced pressure. The crude product is filtered with dichloromethane/methanol through silica gel (300 g, 50 μm Combiflash system), and the product fractions are concentrated under reduced pressure.

The desired product is obtained as a yellowish oil.

ii) Synthesis of 3-{3-ethyl-4-[3-(methanesulphonyloxy)propyl]phenyl}propyl methanesulphonate (3)

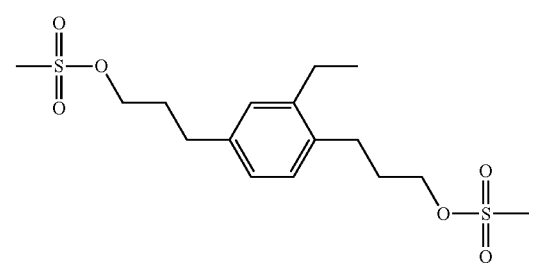

18.2 g (81.9 mmol) of alcohol 2 and 1.0 g (8.2 mmol) of 4-(dimethylamino)pyridine are initially charged in 100 ml of dichloromethane (DCM), and 25 ml (309.7 mmol) of pyridine are added. The reaction mixture is cooled to 3-4° C., and 15.0 ml (193.4 mmol) of methanesulphonyl chloride are added dropwise. 5 min after addition, the cooling bath is removed and then the mixture is stirred at room temperature for 2 hours. On completion of conversion, the reaction mixture is poured cautiously onto water and the phases are separated. The water phase is extracted with DCM, and the combined organic phases are washed with 2 N hydrochloric acid and water, dried over sodium sulphate, filtered and concentrated under reduced pressure. The oily crude product is filtered through 1 litre (l) of silica gel with (DCM:MTB ether 98:2 to 95:5 to 9:1), and the product fractions are concentrated under reduced pressure.

The product is obtained as a colourless oil.

iii) Synthesis of 4-[3-(3-ethyl-4-{3-[(1-oxyl-2,2,6,6-tetramethylpiperidin-4-yl)oxy]propyl}phenyl)propoxy]-2,2,6,6-tetramethylpiperidin-1-oxyl (free radical) (4)

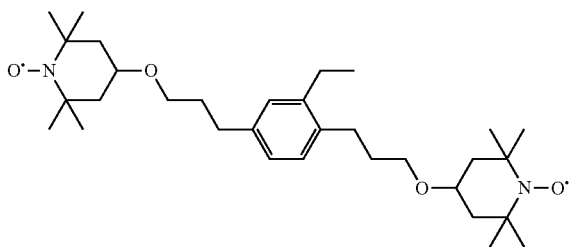

4

To 6.20 g (155 mmol) of sodium hydride (60% in paraffin oil) at room temperature (RT) are cautiously added 50 ml of N,N-dimethylformamide (DMF), and the mixture is heated to 40° C. At this temperature, a solution of 27.0 g (157 mmol) of 4-hydroxy-TEMPO (free-radical) is added dropwise (gentle evolution of hydrogen gas). On completion of addition and after evolution of gas has ended, the mixture is stirred at 40° C. for another 2 hours and then cooled down to room temperature. Then a solution of 23.6 g (62.4 mmol) of mesylate 3 in 100 ml of DMF is added within 10 min (the temperature rises here by 5° C. to 30° C.) and then the mixture is stirred at room temperature for 48 h. The reaction solution is cautiously poured onto ice-water and extracted with MTB ether. The phases are separated and the water phase is extracted with MTB ether. The organic phases are combined, dried over sodium sulphate, filtered and concentrated under reduced pressure. The crude product is obtained as a red oil and is filtered through 1.3 l of silica gel with a mixture of heptane (H)/ethyl acetate (EA) (2:1). The product fractions are concentrated under reduced pressure and the product is obtained as a red solid. The mixture is filtered once again through 1 l of silica gel with H:EA (3:1 to 2:1), and the product obtained is crystallized from 250 ml of heptane and 10 ml of ethanol at −20° C.

The product is obtained as an orange solid.

iv) Synthesis of 4-[3-(3-ethyl-4-{3-[(2,2,6,6-tetramethylpiperidin-4-yl)oxy]propyl}phenyl)propoxy]-2,2,6,6-tetramethylpiperidine (Compound of the Formula I-1)

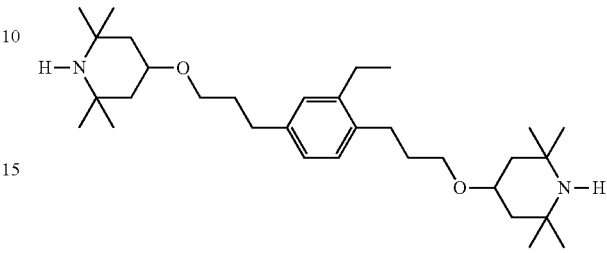

I-1

21.4 g (40.3 mmol) of free radical 4 are dissolved in 200 ml of tetrahydrofuran (THF), and hydrogenation is effected with 10 g of sponge nickel catalyst (watery) (Johnson Matthey GmbH A-7000) under a 5 bar hydrogen atmosphere and at 50° C. for 16 hours. A further two lots of 10 g of catalyst are added (after filtration) and reduction is effected under a 5 bar hydrogen atmosphere at 50° C. for a further 34 hours. The catalyst is filtered out of the reaction solution which is concentrated and filtered with MTBE through 500 ml of Alox (basic) and concentrated under reduced pressure. The crude product is dissolved cautiously in 100 ml of 2N hydrochloric acid and extracted twice with MTB ether. Subsequently, the aqueous phase (hydrochloride product present) is adjusted cautiously to pH 9-10 with 32% NaOH solution and the water phase is extracted repeatedly with MTBE. The combined organic phases are washed with water, dried over sodium sulphate, filtered and concentrated under reduced pressure. The colourless oil obtained is dried at 0.4 mbar for 4 hours.

Phases: $T_g$ −43° C. isotropic
$^1$H NMR (500 MHz, CDCl$_3$)
δ=0.68 ppm s (broad) (2H, 2×NH), 1.03 (dt, 3.78, 11.74 Hz, 4H), 1.14, 1.15, 1.18, 1.18 (4S, 24 H, CH$_3$), 1.24 (t, 7.54 Hz, 3 H, CH$_3$), 1.89 (m$_c$, 4H), 1.96 (dd, 3.97, 12.6 Hz, 4 H), 2.61-2.71 (m, 6 H), 3.52 (2 t$_{(masked)}$, 7.53 Hz, 4 H), 3.66 (m$_c$, 2 H, CH), 6.96 (dd, 1.59, 7.71 Hz, 1 H, arom.-H), 7.03 (s (broad), 1 H, arom.-H), 7.09, (d, 7.72 Hz, 1 H, arom.-H).

Synthesis Example I-6

Synthesis of 4-[3-(2,5-difluoro-4-{3-[(2,2,6,6-tetramethylpiperidin-4-yl)oxy]propyl}phenyl)propoxy]-2,2,6,6-tetramethylpiperidine (Compound of the Formula I-6)

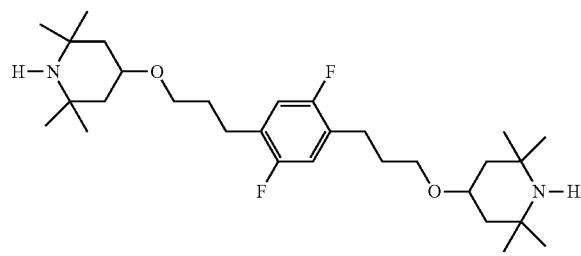

I-6

Compound I-6 is prepared analogously to Synthesis Example I-1 for compound I-1, proceeding from commercially available 1,4-dibromo-2,5-difluorobenzene.

Phases: Tm (melting point)=79° C. isotropic
$^{1}$H NMR (500 MHz, CDCl$_{3}$)
δ=0.69 ppm (s$_{(broad)}$, 2 H, NH), 1.01 (dd, 12.3, 12.3 Hz, 4 H, CH$_{2}$), 1.14, 1.18 (2×s (superimposed with 2×NH) 26 H, CH$_{3}$, NH), 1.86 (q, 7.24 Hz, 4 H, CH$_{2}$), 1.94 (dd, J=3.97, 12.61 Hz, 4 H, CH$_{2}$), 2.67 (t, J=7.49 Hz, 4H, CH$_{2}$), 3.49 (t, J=6.32 Hz, 4 H, CH$_{2}$), 3.61-3.69 (m, 2 H, CH), 6.84 (t, J=7.74 Hz, 2H, arom-H).

Synthesis Example I-9

Synthesis of 2,2,6,6-tetramethyl-4-({10-[(2,2,6,6-tetramethylpiperidin-4-yl)oxy]decyl}oxy)piperidine (Compound of the Formula I-9)

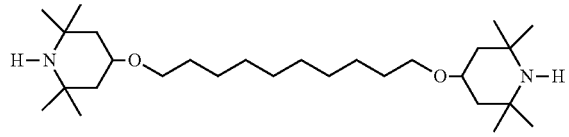

I-9

41.9 g (266 mmol) of 2,2,6,6-tetramethylpiperidin-4-ol are dissolved in 700 ml of toluene, and 28.7 g (1.2 mol) of NaH are added in portions. The mixture is stirred at room temperature for 15 min, and then 40.0 g (133 mmol) of 1,10-dibromodecane are added. The reaction mixture is stirred under reflux for 16 hours, cooled down to room temperature and quenched cautiously with water (evolution of hydrogen). The organic phase is removed, washed with water, dried over sodium sulphate and concentrated under reduced pressure. The oily residue obtained is purified by column chromatography on silica gel with heptane and then with methyl tert-butyl ether (MTB-E).

Phases: Tm (melting point)=36° C. isotropic
$^{1}$H NMR (500 MHz, CDCl$_{3}$)
δ=0.76 ppm (s$_{(broad)}$, 2 H, NH), 1.00 (t, J=11.77 Hz, 4 H, CH$_{2}$), 1.14 (s, 12H, CH$_{3}$), 1.18 (s, 12 H, CH$_{3}$), 1.23-1.37 (m, 12 H, CH$_{2}$), 1.56 (quint, 7.23 Hz, 4 H, CH$_{2}$), 1.95 (dd, J=3.98, 12.65 Hz, 4 H, CH$_{2}$), 3.46 (t, 6.76 Hz, 4 H, CH$_{2}$), 3.65 (m$_{c}$, 2H, CH).

Synthesis Example I-12

Synthesis of 4-{2-[2-fluoro-6-(2-phenylethyl)-3-{3-[(2,2,6,6-tetramethylpiperidin-4-yl)oxy]propyl}phenoxy]ethoxy}-2,2,6,6-tetramethylpiperidine (Compound of the Formula I-12)

I-12

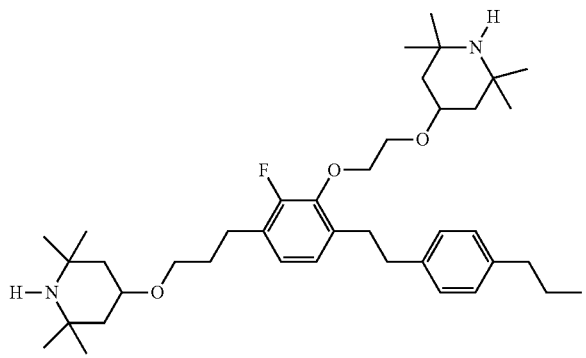

i) Synthesis of [2-(6-bromo-2-fluoro-3-iodophenoxy)ethoxy](tert-butyl)dimethylsilane (5)

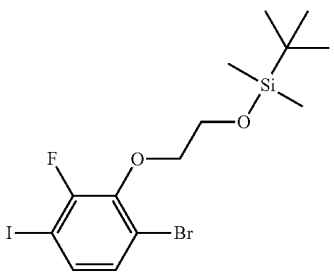

5

43.3 g (135.6 mmol) of commercially available 6-bromo-3-fluoro-3-iodophenol, 38.10 g (159.3 mmol) of (2-bromoethoxy)-tert-butyldimethylsilane are dissolved in 130 ml of N,N-dimethylformamide (DMF). 66.95 g (203.4 mmol) of caesium carbonate are added to the reaction mixture which is then stirred at 50° C. for 16 hours. The reaction mixture is poured onto ice-water and extracted repeatedly with ethyl acetate (EA), and the organic phases are combined, dried over sodium sulphate, filtered and concentrated under reduced pressure. The crude product is obtained as a brown liquid and is filtered through silica gel with heptane and heptane/toluene (10:1). The product fractions are concentrated under reduced pressure and the colourless oil obtained is separated from residues of DMF at 160° C. and a vacuum of 6 mbar.

ii) Synthesis of [2-(6-bromo-3-{3-[(tert-butyldimethylsilyl)oxy]prop-1-yn-1-yl}-2-fluorophenoxy)ethoxy](tert-butyl)dimethylsilane (6)

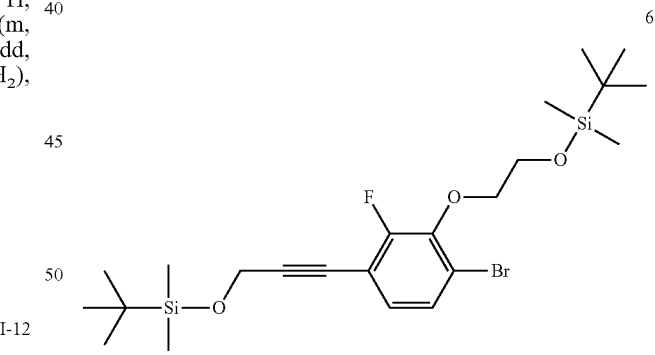

6

28.0 g (58.9 mmol) of bromide 5 are initially charged in 300 ml of triethylamine at room temperature (RT) and degassed. 1.30 g (1.85 mmol) of bis(triphenylphosphine)palladium(II) chloride (15.2% Pd) and 350 mg (1.84 mmol) of copper(I) iodide are added and, at room temperature, a solution of 20.0 g (117 mmol) of tert-butyldimethyl-prop-2-ynyloxysilane in 150 ml of degassed triethylamine is added dropwise. The reaction mixture warms up to 31° C. in the course of dropwise addition and a thick suspension is formed, which is stirred at room temperature for a further 2 hours. The reaction mixture is filtered with suction, and the filtrate is concentrated under reduced pressure and dissolved with methyl tert-butyl ether (MTB-E). The filter residue is extracted with MTB-E. The combined organic phases are washed with ammonium chloride and sodium chloride solution, dried over sodium sulphate, filtered and concentrated under reduced pressure. The crude product is obtained as a dark oil which is purified on silica gel with heptane/toluene (9:1 to 1:1). The product obtained occurs as an orange oil.

iii) Synthesis of tert-butyl[2-(3-{3-[(tert-butyldimethylsilyl)oxy]prop-1-yn-1-yl}-2-fluoro-6-(2-phenylethynyl)phenoxy)ethoxy]dimethylsilane (7)

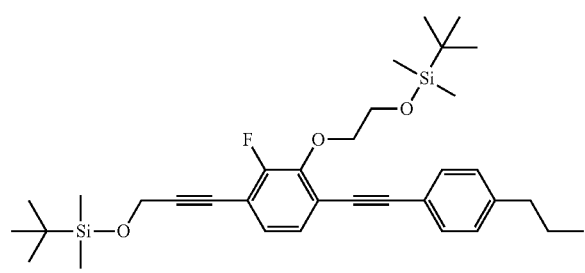

7

24.1 g (46.6 mmol) of bromide 6 and 8.00 g (55.5 mmol) of 1-ethynyl-4-propylbenzene are dissolved in 300 ml of diisopropylamine and degassed for 30 min. 500 mg (2.23 mmol) of palladium(II) acetate, 700 mg (2.41 mmol) of tri-tert-butylphosphonium tetrafluoroborate and 350 mg (1.84 mmol) of copper(I) iodide are added to the reaction mixture which is stirred at 80° C. for one hour. The reaction mixture darkens and a solid precipitates out. The mixture is cooled down to room temperature, filtered and concentrated under reduced pressure. The filtrate is taken up in MTB ether, and the ammonium salts filtered off with suction are rinsed with MTB ether until the filtrate is colourless. The organic phases are combined, washed with ammonium chloride and sodium chloride solution, dried over sodium sulphate, filtered and concentrated under reduced pressure. The crude product is obtained as a black oil which is filtered through silica gel with heptane/toluene (7:3 to 1:1). The product fractions are combined and concentrated under reduced pressure. The product is obtained as an orange semicrystalline solid.

iv) Synthesis of tert-butyl[2-(3-{3-[(tert-butyldimethylsilyl)oxy]propyl}-2-fluoro-6-(2-phenylethyl)phenoxy)ethoxy]dimethylsilane (8)

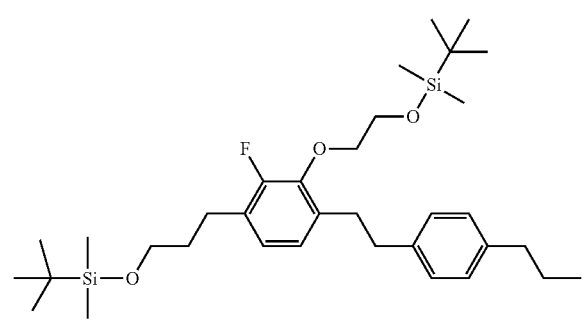

8

22.2 g (38.2 mmol) of compound 7 and 2.00 g of sponge nickel catalyst (Johnson Matthey, in water, A-700) are dissolved in 220 ml of tetrahydrofuran (THF) and stirred under a hydrogen atmosphere at room temperature and standard pressure for 20.5 hours. The reaction mixture is filtered and the solution is concentrated under reduced pressure. The crude product is purified using silica gel with heptane/chlorobutane (1:1 to 1:2). The product fractions are concentrated under reduced pressure and the reaction product is obtained as an orange oil.

v) Synthesis of 3-[2-fluoro-3-(2-hydroxyethoxy)-4-(2-phenylethyl)phenyl]propan-1-ol (9)

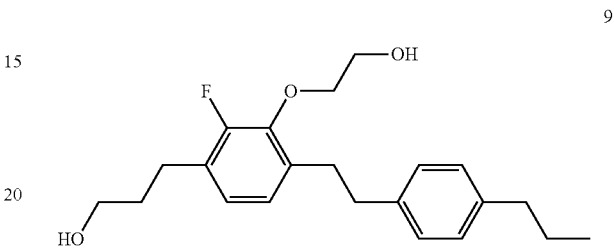

9

17.3 g (27.7 mmol) of compound 8 are dissolved in 200 ml of tetrahydrofuran and cooled down to 2° C. 80.0 ml (80 mmol) of a 1 molar solution of tetrabutylammonium fluoride are added dropwise and the mixture is stirred at room temperature for a further 3 hours. The reaction solution is poured onto an ice-cold sodium hydrogencarbonate/MTBE mixture and stirred briefly, and the phases are separated. The water phase is extracted with MTB ether, and the combined organic phases are washed with sodium chloride solution, dried over sodium sulphate, filtered and concentrated under reduced pressure. The reaction product is obtained as an orange oil which is purified using silica gel with dichloromethane/methanol (95:5 to 9:1). The crude product obtained is crystallized from heptane at −25° C., and compound 9 is obtained as beige crystals.

$^1$H NMR (500 MHz, CDCl$_3$)

δ=0.96 ppm (t, J=7.35 Hz, 3 H, CH$_3$), 1.32 (s$_{(broad)}$, 1 H, OH), 1.66 (sext., J=7.41 Hz, 2 H, CH$_2$CH$_3$), 1.86-1.95 (m$_c$, 2 H, CH$_2$), 2.07 (s$_{(broad)}$, 1 H, OH), 2.58 (dd, J=7.54 Hz, 2 H, CH$_2$), 2.75 (t$_{(broad)}$, J=8.29 Hz, 2 H, CH$_2$), 2.91 (m$_c$, 4 H), 3.71 (t, J=6.37 Hz, 2 H, CH$_2$), 3.92 (dd$_{(broad)}$, 4.61 Hz, 2 H, CH$_2$), 4.08 (dd$_{(broad)}$, 4.08 Hz, 2 H, CH$_2$), 6.84-6.92 (m, 2 H), 7.12 (s, 4 H).

vi) Synthesis of 4-{-2-[2-fluoro-6-(2-phenylethyl)-3-{3-[(2,2,6,6-tetramethylpiperidin-4-yl)oxy]propyl}phenoxy]ethoxy}-2,2,6,6-tetramethylpiperidine (Compound of the Formula I-12)

I-12

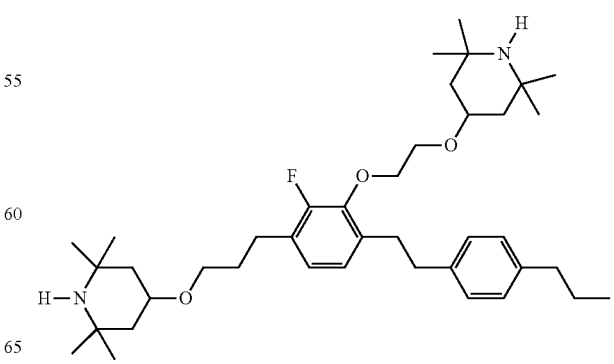

Proceeding from compound 9, compound I-12 is prepared analogously to the synthesis example I-1 shown. The product is obtained as a colourless oil.

Phases: $T_g$ –31° C. isotropic $^1$H NMR (500 MHz, CDCl$_3$)

δ=0.61-0.78 ppm (2 s$_{(broad, overlapping)}$, 2 H, OH), 0.86 (t, J=7.36 Hz, 3 H, CH$_3$), 0.92 (d, J=11.3 Hz, 2 H, CH$_2$), 0.96 (d, J=11.22 Hz, 2 H, CH$_2$), 1.04 (s, 6 H, CH$_3$), 1.08 (s, 6 H, CH$_3$), 1.09 (s, 6 H, CH$_3$), 1.12 (s, 6 H, CH$_3$), 1.55 (sext, J=7.57 Hz, 2 H, CH$_2$CH$_3$), 1.79 (quint, J=6.93 Hz, 2 H, CH$_2$), 1.89 (m$_c$, 4 H), 2.48 (t, J=7.8 Hz, 2 H, CH$_2$), 2.62 (t, J=7.51 Hz, 2 H, CH$_2$), 2.82 (m$_c$, 4 H, CH$_2$), 3.43 (t, J=6.42 Hz, 2 H, CH$_2$), 3.58 (m$_c$, 1 H, CH), 3.61-3.78 (m, 3 H, CH$_2$, CH), 4.08 (t, J=5.1 Hz, 2 H, CH$_2$), 6.69-7.78 (m, 2 H), 7.01 (d, J=8 Hz, 2 H), 7.07 (d, J=7.99 Hz).

Liquid-crystal mixtures having the compositions and the properties as specified in the tables which follow are produced and examined. The improved or favourable stability of the mixtures comprising compounds of the formula I is shown by corresponding comparisons with unstabilized base mixtures or differently stabilized mixtures.

Reference Example 1, Examples 1.1-1.12 and Comparative Examples 1.a-1.c

The following mixture (M-1) is prepared and examined.

| Mixture M-1 | | |
|---|---|---|
| Composition | | |
| Compound | | Concentration |
| No. | Abbreviation | /% by mass |
| 1 | CC-3-V | 32.00 |
| 2 | CC-3-V1 | 11.00 |
| 3 | CC-3-2V1 | 4.50 |
| 4 | PP-1-2V1 | 2.00 |
| 5 | CCP-3-OT | 7.50 |
| 6 | CCP-5-OT | 1.50 |
| 7 | PUQU-3-F | 1.50 |
| 8 | APUQU-2-F | 7.00 |
| 9 | APUQU-3-F | 7.00 |
| 10 | PGUQU-3-F | 3.00 |
| 11 | PGUQU-4-F | 8.00 |
| 12 | PGUQU-5-F | 2.00 |
| 13 | DPGU-4-F | 5.00 |
| 14 | DGUQU-4-F | 8.00 |
| Σ | | 100.0 |
| Physical properties | | |
| T(N, I) [° C.)] = 85.0 | | |
| $n_e$(20° C., 589 nm) = 1.587 | | |
| Δn(20° C., 589 nm) = 0.109 | | |
| $\varepsilon_\perp$(20°, 1 kHz) = 3.7 | | |
| Δε(20°, 1 kHz) = 15.3 | | |
| $k_{11}$(20° C.) [pN] = 14.4 | | |
| $k_{33}$(20° C.) [pN] = 15.1 | | |
| $V_0$(20° C.) [V] = 1.01 | | |

The mixture M-1 is divided into 16 portions and examined as described hereinafter.

The first portion of the mixture M-1 is used as prepared in Reference Example 1 (Ref.).

To each of three of the remaining portions is added TINUVIN®770, called T770 hereinafter, i.e. a compound of the formula

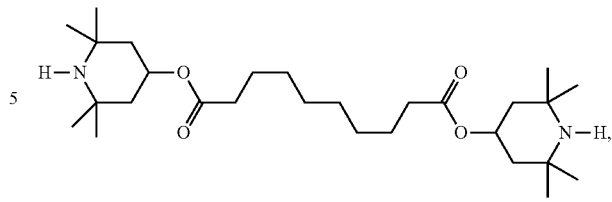

in each case in a concentration as listed in Table 1 below. The mixtures M-1.a, M-1.b and M-1.c thus produced are used in Comparative Examples 1.a to 1.c (Comp.).

According to the invention, one compound of the formulae I-1, I-6-, I-9 and I-12 as shown above is added to each of the remaining 12 portions, each in a concentration as listed in Table 1 below. The mixtures M-1.1 to M-1.12 thus produced are used in Inventive Examples 1.1 to 1.12.

TABLE 1

| | Mixture | Stabilizer | Concentration of the stabilizer [ppm] |
|---|---|---|---|
| 1 (Ref.) | M-1 | — | — |
| 1.a (Comp.) | M-1.a | T770 | 100 |
| 1.b (Comp.) | M-1.b | T770 | 500 |
| 1.c (Comp.) | M-1.c | T770 | 1000 |
| 1.1 | M-1.1 | I-1 | 100 |
| 1.2 | M-1.2 | I-1 | 500 |
| 1.3 | M-1.3 | I-1 | 1000 |
| 1.4 | M-1.4 | I-6 | 100 |
| 1.5 | M-1.5 | I-6 | 500 |
| 1.6 | M-1.6 | I-6 | 1000 |
| 1.7 | M-1.7 | I-9 | 100 |
| 1.8 | M-1.8 | I-9 | 500 |
| 1.9 | M-1.9 | I-9 | 1000 |
| 1.10 | M-1.10 | I-12 | 100 |
| 1.11 | M-1.11 | I-12 | 500 |
| 1.12 | M-1.12 | I-12 | 1000 |

These mixtures are examined for their stability as described hereinafter.

First of all, what is called the initial voltage holding ratio (VHR (initial)) is examined. For this purpose, the VHR is determined in test cells produced by Merck Japan. The test cells have substrates composed of soda-lime glass and have been designed with polyimide alignment layers (AL-16301 from Japan Synthetic Rubber, Japan) with a layer thickness of 50 nm that have been rubbed at right angles to one another. The layer thickness is a uniform 6.5 μm. The area of the transparent electrodes composed of ITO is 1 cm$^2$.

The VHR is determined at 20° C. (VHR$_{20}$) and after 5 minutes in an oven at 100° C. (VHR$_{100}$) in a commercially available instrument from Autronic Melchers, Germany, at 1 V and 60 Hz.

The values of VHR (initial) thus ascertained are listed in Table 2.

In addition, light stability to sunlight, i.e. stability to irradiation with UV/sunlight, is examined in a commercial "Suntest CPS" instrument from Heraeus, Germany.

For determination of VHR in relation to sunlight stability, a lamp that emits the wavelength spectrum of sunlight is used. The test is conducted at 20° C. and the irradiation time corresponds to 30 min. The sealed test cells are irradiated here with a lamp (Hoya, 340 nm cut filter, T=50% at 340 nm) at 20° C. without additional thermal stress for 0.5 hour, over the course of which the intensity measured with a 365 nm sensor is 3 J/cm$^2$. Thereafter, the voltage holding ratio in each case is determined after 5 minutes at a temperature of 100° C.

The VHR values thus ascertained for the sun test (VHR (suntest)) are likewise listed in Table 2.

TABLE 2

| | Mixture | VHR (initial) [%] | VHR (suntest) [%] |
|---|---|---|---|
| 1 (Ref.) | M-1 | 96.4 | 72.4 |
| 1.a (Comp.) | M-1.a | 98.0 | 89.3 |
| 1.b (Comp.) | M-1.b | 98.0 | 85.7 |
| 1.c (Comp.) | M-1.c | 97.8 | 85.9 |
| 1.1 | M-1.1 | 98.6 | 90.7 |
| 1.2 | M-1.2 | 98.4 | 86.5 |
| 1.3 | M-1.3 | 98.5 | 82.8 |
| 1.4 | M-1.4 | 98.7 | 86.0 |
| 1.5 | M-1.5 | 98.9 | 78.4 |
| 1.6 | M-1.6 | 99.0 | 71.9 |
| 1.7 | M-1.7 | 98.3 | 85.3 |
| 1.8 | M-1.8 | 98.4 | 72.4 |
| 1.9 | M-1.9 | 98.0 | 61.5 |
| 1.10 | M-1.10 | 98.4 | 90.2 |
| 1.11 | M-1.11 | 98.0 | 81.8 |
| 1.12 | M-1.12 | 97.9 | 75.6 |

It is found that the mixtures according to the invention can be distinctly stabilized, even if they contain the corresponding compounds of the formula I in relatively low concentrations.

In addition, light stability to backlighting is examined, by examining the mixtures in a test cell with an alignment material for planar alignment and full-area ITO electrodes for their light stability (backlighting). For determination of the VHR with respect to light stability to backlighting, sealed test cells are tested with a commercially available backlighting unit without additional thermal stress. The duration of irradiation corresponds to max. 1000 h. The results (VHR (BL)) are listed in Table 3.

TABLE 3

| | | VHR (initial) [%] | VHR (BL) [%] | | | | | |
|---|---|---|---|---|---|---|---|---|
| | | | 48 h | 168 h | 336 h | 504 h | 744 h | 1000 h |
| 1 (Ref.) | M-1 | 95.4 | 81.5 | 69.0 | 65.1 | 62.7 | 61.4 | 59.7 |
| 1.a (Comp.) | M-1.a | 97.8 | 95.9 | 90.8 | 86.5 | 82.9 | 79.3 | 76.8 |
| 1.b (Comp.) | M-1.b | 97.5 | 95.7 | 92.6 | 89.9 | 87.4 | 85.0 | 82.5 |
| 1.c (Comp.) | M-1.c | 97.3 | 96.0 | 93.9 | 90.9 | 88.5 | 86.5 | 84.8 |
| 1.1 | M-1.1 | 98.1 | 96.8 | 93.9 | 90.9 | 88.5 | 87.6 | 83.7 |
| 1.2 | M-1.2 | 98.2 | 97.4 | 95.2 | 93.0 | 91.1 | 89.8 | 87.9 |
| 1.3 | M-1.3 | 98.2 | 97.1 | 95.1 | 92.8 | 90.8 | 89.2 | 87.5 |
| 1.4 | M-1.4 | 98.7 | 97.3 | 94.2 | 91.7 | 88.8 | 86.2 | 84.0 |
| 1.5 | M-1.5 | 98.4 | 97.2 | 94.4 | 91.4 | 87.8 | 84.9 | 85.8 |
| 1.6 | M-1.6 | 98.2 | 97.1 | 93.5 | 91.6 | 89.5 | 87.6 | 86.0 |
| 1.7 | M-1.7 | 97.2 | 96.6 | 94.4 | 92.1 | 89.5 | 86.6 | 84.7 |
| 1.8 | M-1.8 | 97.4 | 95.5 | 92.3 | 89.5 | 87.3 | 85.3 | 83.9 |
| 1.9 | M-1.9 | 97.0 | 95.1 | 91.9 | 89.0 | 86.9 | 84.8 | 83.3 |
| 1.10 | M-1.10 | 98.5 | 97.5 | 93.6 | 91.7 | 89.3 | 85.4 | 82.0 |
| 1.11 | M-1.11 | 98.2 | 97.4 | 95.1 | 92.8 | 90.9 | 88.2 | 85.6 |
| 1.12 | M-1.12 | 98.1 | 96.8 | 94.2 | 91.1 | 88.5 | 85.9 | 84.1 |

It is found that the mixtures according to the invention can be distinctly stabilized with respect to backlighting as well, even if they contain the corresponding compounds of the formula I in relatively low concentrations.

For comparison and as a reference, the mixtures M-1, M-1.a, M-1.b and M-1.c are also examined with regard to their heat stability.

This is done by examining these mixtures for their heat stability in a test cell with an alignment material for planar alignment and full-area ITO electrodes. For determination of the VHR as a function of heat stability, sealed test cells are stored at 100° C. in a conventional laboratory heating cabinet for 120 h. The results (VHR (heat)) are shown in Table 4.

TABLE 4

| | Mixture | VHR (initial) [%] | VHR (heat) [%] |
|---|---|---|---|
| 1 (Ref.) | M-1 | 96.3 | 91.1 |
| 1.a (Comp.) | M-1.a | 97.7 | 90.2 |
| 1.b (Comp.) | M-1.b | 98.5 | 94.0 |
| 1.c (Comp.) | M-1.c | 97.8 | 84.9 |

Reference Example 2, Examples 2.1-2.9 and Comparative Examples 2.a-2.c

The following mixture (M-21 is prepared and examined.

| Mixture M-2 | | |
|---|---|---|
| Composition | | |
| Compound | | Concentration |
| No. | Abbreviation | /% by mass |
| 1 | CCY-3-O1 | 3.50 |
| 2 | CLY-3-O2 | 10.00 |
| 3 | CLY-3-O3 | 2.50 |
| 4 | CPY-2-O2 | 11.00 |
| 5 | CPY-3-O2 | 12.50 |
| 6 | PYP-2-3 | 4.00 |
| 7 | CC-3-V | 28.00 |
| 8 | CC-3-V1 | 12.00 |
| 9 | CY-3-O2 | 13.50 |
| 10 | CY-5-O2 | 3.00 |
| Σ | | 100.0 |
| Physical properties | | |
| $T(N, I)$ [° C.)] = 85.5 | | |
| $n_e$(20° C., 589 nm) = 1.588 | | |
| $\Delta n$(20° C., 589 nm) = 0.105 | | |
| $\varepsilon_\perp$(20°, 1 kHz) = 6.9 | | |
| $\Delta\varepsilon$(20°, 1 kHz) = −3.4 | | |
| $k_{11}$(20° C.) [pN] = 14.7 | | |
| $k_{33}$(20° C.) [pN] = 17.7 | | |
| $V_0$(20° C.) [V] = 2.41 | | |

The mixture M-2 is divided into 13 portions and examined as described hereinafter.

The first portion of the mixture M-2 is used as prepared in Reference Example 2 (Ref.).

To each of three of the remaining portions is added TINUVIN®770 (T770), in each case in a concentration as listed in Table 5 below. The mixtures M-2.a, M-2.b and M-2.c thus produced are used in Comparative Examples 2.a to 2.c (Comp.).

According to the invention, one compound of the formulae I-1, I-6 and I-9 as shown above is added to each of the remaining 9 portions, each in a concentration as listed in Table 5 below. The mixtures M-2.1 to M-2.9 thus produced are used in Inventive Examples 2.1 to 2.9.

TABLE 5

| | Mixture | Stabilizer | Concentration of the stabilizer [ppm] |
|---|---|---|---|
| 2 (Ref.) | M-2 | — | — |
| 2.a (Comp.) | M-2.a | T770 | 100 |
| 2.b (Comp.) | M-2.b | T770 | 500 |
| 2.c (Comp.) | M-2.c | T770 | 1000 |
| 2.1 | M-2.1 | I-1 | 100 |
| 2.2 | M-2.2 | I-1 | 500 |
| 2.3 | M-2.3 | I-1 | 1000 |
| 2.4 | M-2.4 | I-6 | 100 |
| 2.5 | M-2.5 | I-6 | 500 |
| 2.6 | M-2.6 | I-6 | 1000 |
| 2.7 | M-2.7 | I-9 | 100 |
| 2.8 | M-2.8 | I-9 | 500 |
| 2.9 | M-2.9 | I-9 | 1000 |

These mixtures are examined for their stability as described hereinafter.

First of all, what is called the initial voltage holding ratio (VHR (initial)) is examined as described above for the mixtures M-1 to M-1.16.

The values of VHR (initial) ascertained are listed in Table 6.

In addition, light stability against sunlight is examined as described above for the mixtures M-1 to M-1.16.

The VHR values ascertained for the sun test (VHR (suntest)) are likewise listed in Table 6.

TABLE 6

| | Mixture | VHR (initial) [%] | VHR (suntest) [%] |
|---|---|---|---|
| 2 (Ref.) | M-2 | 72.8 | 66.0 |
| 2.a (Comp.) | M-2.a | 82.4 | 81.3 |
| 2.b (Comp.) | M-2.b | 84.4 | 84.3 |
| 2.c (Comp.) | M-2.c | 83.7 | 84.6 |
| 2.1 | M-2.1 | 89.8 | 89.9 |
| 2.2 | M-2.2 | 89.9 | 89.6 |
| 2.3 | M-2.3 | 90.1 | 90.0 |
| 2.4 | M-2.4 | 89.5 | 87.3 |
| 2.5 | M-2.5 | 89.7 | 86.6 |
| 2.6 | M-2.6 | 88.3 | 84.5 |
| 2.7 | M-2.7 | 89.2 | 88.8 |
| 2.8 | M-2.8 | 89.4 | 87.6 |
| 2.9 | M-2.9 | 89.6 | 87.5 |

Surprisingly, the mixtures having negative dielectric anisotropy exhibit particularly excellent stabilization when they comprise the corresponding compounds of the formula I in accordance with the invention, wherein a relatively small amount can advantageously be sufficient.

Reference Example 3, Examples 3.1-3.6 and Comparative Examples 3.a-3.c

The following mixture (M-3) is prepared and examined.

| Mixture M-3 | | |
|---|---|---|
| Composition | | |
| Compound | | Concentration |
| No. | Abbreviation | /% by mass |
| 1 | CCY-3-O2 | 10.00 |
| 2 | CCY-5-O2 | 7.00 |
| 3 | CPY-2-O2 | 10.00 |
| 4 | CPY-3-O2 | 10.00 |
| 5 | PYP-2-3 | 5.50 |
| 6 | B-2O-O5 | 4.00 |
| 7 | CC-3-V | 32.00 |
| 8 | CC-3-V1 | 10.00 |
| 9 | CY-3-O2 | 10.00 |
| 10 | CY-5-O2 | 1.50 |
| Σ | | 100.0 |
| Physical properties | | |
| $T(N, I)\ [°\ C.] = 85.0$ | | |
| $n_e(20°\ C., 589\ nm) = 1.587$ | | |
| $\Delta n(20°\ C., 589\ nm) = 0.105$ | | |
| $\varepsilon_\perp(20°, 1\ kHz) = 6.9$ | | |
| $\Delta\varepsilon(20°, 1\ kHz) = -3.4$ | | |
| $k_{11}\ (20°\ C.)\ [pN] = 14.6$ | | |
| $k_{33}(20°\ C.)\ [pN] = 17.4$ | | |
| $V_0(20°\ C.)\ [V] = 2.37$ | | |

The mixture M-3 is divided into 10 portions and examined as described hereinafter.

The first portion of the mixture M-3 is used as prepared in Reference Example 3 (Ref.).

To each of three of the remaining portions is added TINUVIN®770 (T770), in each case in a concentration as listed in Table 7 below. The mixtures M-3.a, M-3.b and M-3.c thus produced are used in Comparative Examples 3.a to 3.c (Comp.).

According to the invention, one compound of the formulae I-1 and I-12 as shown above is added to each of the remaining 6 portions, each in a concentration as listed in Table 7 below. The mixtures M-3.1 to M-3.6 thus produced are used in Inventive Examples 3.1 to 3.6.

TABLE 7

| | Mixture | Stabilizer | Concentration of the stabilizer [ppm] |
|---|---|---|---|
| 3 (Ref.) | M-3 | — | — |
| 3.a (Comp.) | M-3.a | T770 | 100 |
| 3.b (Comp.) | M-3.b | T770 | 500 |
| 3.c (Comp.) | M-3.c | T770 | 1000 |
| 3.1 | M-3.1 | I-1 | 100 |
| 3.2 | M-3.2 | I-1 | 500 |
| 3.3 | M-3.3 | I-1 | 1000 |
| 3.4 | M-3.4 | I-12 | 100 |
| 3.5 | M-3.5 | I-12 | 500 |
| 3.6 | M-3.6 | I-12 | 1000 |

These mixtures are examined for their stability as described hereinafter.

First of all, what is called the initial voltage holding ratio (VHR (initial)) is examined as described above for the mixtures M-1 to M-1.16.

The values of VHR (initial) ascertained are listed in Table 8.

In addition, light stability against sunlight is examined as described above for the mixtures M-1 to M-1.16.

The VHR values ascertained for the sun test (VHR (suntest)) are likewise listed in Table 8.

TABLE 8

|  | Mixture | VHR (initial) [%] | VHR (suntest) [%] |
|---|---|---|---|
| 3 (Ref.) | M-3 | 68.9 | 52.0 |
| 3.a (Comp.) | M-3.a | 76.5 | 70.0 |
| 3.b (Comp.) | M-3.b | 81.0 | 75.5 |
| 3.c (Comp.) | M-3.c | 79.5 | 74.8 |
| 3.1 | M-3.1 | 85.2 | 79.0 |
| 3.2 | M-3.2 | 84.3 | 80.0 |
| 3.3 | M-3.3 | 84.7 | 80.2 |
| 3.4 | M-3.4 | 85.6 | 79.4 |
| 3.5 | M-3.5 | 86.1 | 82.0 |
| 3.6 | M-3.6 | 86.3 | 81.2 |

Surprisingly, the mixtures having negative dielectric anisotropy exhibit particularly excellent stabilization when they comprise the corresponding compounds of the formula I in accordance with the invention, wherein a relatively small amount can advantageously be sufficient.

In addition, the mixtures M-3, M-3.a to M-3.c and M-3.1 to M-3.3 are examined with regard to their heat stability. These studies are performed as already described above for the mixtures M-1, M-1.a, M-1.b and M-1.c.

The results (VHR (heat)) are shown in Table 9.

TABLE 9

|  | Mixture | VHR (initial) [%] | VHR (heat) [%] |
|---|---|---|---|
| 3 (Ref.) | M-3 | 74.0 | 56.2 |
| 3.a (Comp.) | M-3.a | 84.4 | 79.3 |
| 3.b (Comp.) | M-3.b | 84.1 | 80.1 |
| 3.c (Comp.) | M-3.c | 84.7 | 79.0 |
| 3.1 | M-3.1 | 88.1 | 84.8 |
| 3.2 | M-3.2 | 88.2 | 81.5 |
| 3.3 | M-3.3 | 89.1 | 77.3 |

It is found that the mixtures according to the invention can be distinctly stabilized with respect to heat stability as well, even if they contain the corresponding compounds of the formula I in relatively low concentrations.

Reference Example 4, Examples 4.1-4.3 and Comparative Examples 4.a-4.c

The following mixture (M-4) is prepared and examined.

Mixture M-4

Composition

| No. | Compound Abbreviation | Concentration /% by mass |
|---|---|---|
| 1 | CY-3-O2 | 12.00 |
| 2 | CY-3-O4 | 2.00 |
| 3 | CY-5-O2 | 12.00 |
| 4 | CCY-3-O1 | 6.00 |
| 5 | CCY-3-O2 | 8.00 |
| 6 | CCY-4-O2 | 8.00 |
| 7 | CPY-2-O2 | 9.00 |
| 8 | CPY-3-O2 | 9.00 |
| 9 | PYP-2-3 | 5.00 |
| 10 | CC-3-V1 | 5.00 |
| 11 | CC-3-V | 19.00 |
| 12 | BCH-32 | 5.00 |
| Σ |  | 100.0 |

Physical properties $T(N, I)\ [°\ C.] = 86.5$
$n_e(20°\ C., 589\ nm) = 1.592$
$\Delta n(20°\ C., 589\ nm) = 0.109$
$\varepsilon_\perp(20°, 1\ kHz) = 7.9$
$\Delta\varepsilon(20°, 1\ kHz) = -4.2$
$k_{11}(20°\ C.)\ [pN] = 14.6$
$k_{33}(20°\ C.)\ [pN] = 16.6$
$V_0(20°\ C.)\ [V] = 2.08$ The mixture M-4 is divided into 7 portions and examined as described hereinafter.

The first portion of the mixture M-4 is used as prepared in Reference Example 4 (Ref.).

To each of three of the remaining portions is added TINUVIN®770 (T770), in each case in a concentration as listed in Table 10 below. The mixtures M-4.a, M-4.b and M-4.c thus produced are used in Comparative Examples 4.a to 4.c (Comp.).

According to the invention, the compound of the formula I-1 as shown above is added to the remaining 3 portions, in each case in a concentration as listed in Table 10 below. The mixtures M-4.1 to M-4.3 thus produced are used in Inventive Examples 4.1 to 4.3.

TABLE 10

|  | Mixture | Stabilizer | Concentration of the stabilizer [ppm] |
|---|---|---|---|
| 4 (Ref.) | M-4 | — | — |
| 4.a (Comp.) | M-4.a | T770 | 100 |
| 4.b (Comp.) | M-4.b | T770 | 500 |
| 4.c (Comp.) | M-4.c | T770 | 1000 |
| 4.1 | M-4.1 | I-1 | 100 |
| 4.2 | M-4.2 | I-1 | 500 |
| 4.3 | M-4.3 | I-1 | 1000 |

These mixtures are examined for their stability as described hereinafter.

First of all, what is called the initial voltage holding ratio (VHR (initial)) is examined as described above for the mixtures M-1 to M-1.16.

The values of VHR (initial) ascertained are listed in Table 11.

In addition, light stability against sunlight is examined as described above for the mixtures M-1 to M-1.16.

The VHR values ascertained for the sun test (VHR (suntest)) are likewise listed in Table 11.

TABLE 11

| Mixture | VHR (initial) [%] | VHR (suntest) [%] |
|---|---|---|
| 4 (Ref.) | M-4 | 65.8 | 54.5 |
| 4.a (Comp.) | M-4.a | 70.0 | 69.0 |
| 4.b (Comp.) | M-4.b | 69.5 | 70.7 |
| 4.c (Comp.) | M-4.c | 72.2 | 70.7 |
| 4.1 | M-4.1 | 80.2 | 78.2 |
| 4.2 | M-4.2 | 79.1 | 80.1 |
| 4.3 | M-4.3 | 79.5 | 77.6 |

Surprisingly, the mixtures having negative dielectric anisotropy exhibit particularly excellent stabilization when they comprise the corresponding compounds of the formula I in accordance with the invention, wherein a relatively small amount can advantageously be sufficient.

The preceding examples can be repeated with similar success by substituting the generically or specifically described reactants and/or operating conditions of this invention for those used in the preceding examples.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

From the foregoing description, one skilled in the art can easily ascertain the essential characteristics of this invention and, without departing from the spirit and scope thereof, can make various changes and modifications of the invention to adapt it to various usages and conditions.

The entire disclosure[s] of all applications, patents and publications, cited herein and of corresponding DE Patent Application No. 102016009485.0, filed Aug. 5, 2016, are incorporated by reference herein.

The invention claimed is:

1. A compound of formula I

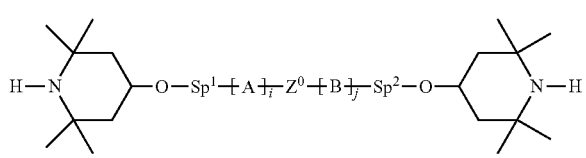

where
Sp$^1$ and Sp$^2$ are each independently a flexible linking or bridging group, which does not contain a —CO— group,
A and B are each independently:
a) trans-1,4-cyclohexylene, 1,4-cyclohexenylene or 1,4'-bicyclohexylene, in which one or two nonadjacent CH$_2$ groups are optionally replaced by —O— and/or —S— and in which one or more hydrogen atoms are optionally replaced by F, or
b) 1,4-phenylene or 1,3-phenylene, in which one or two nonadjacent CH groups are optionally replaced by N and in which one or more hydrogen atoms are optionally replaced by L, or
c)

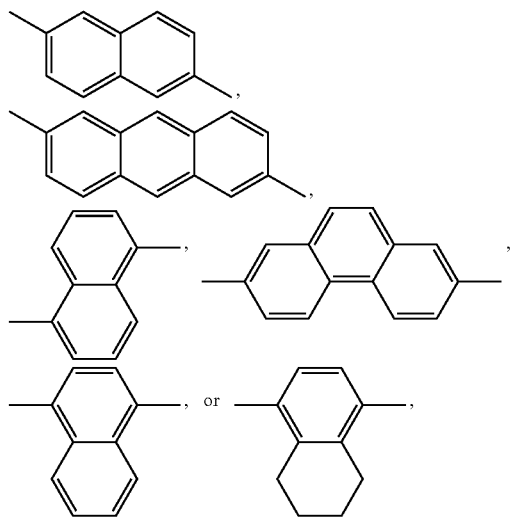

in which one or more hydrogen atoms are optionally replaced by L, and/or one or more double bonds are optionally replaced by single bonds, and/or one or more CH groups are optionally replaced by N,
i and j are each independently 0 or 1,
Z$^0$ is a single bond, —CH$_2$—, —CF$_2$—, —CO—, —O—, —NH—, —NH—(CO)—, —CH$_2$CH$_2$—, —CH=CH—, —CF$_2$O—, —OCF$_2$—, —CH$_2$O—, —OCH$_2$—, —COO—, —OCO—, —C$_2$F$_4$— or —CF=CF—,
and
L is the same or different at each instance and is F, Cl, CN or a straight-chain or branched, in each case optionally fluorinated alkyl, alkoxy, arylalkyl or alkylarylalkyl having 1 to 15 carbon atoms, in which one or more nonadjacent CH$_2$ groups are optionally replaced by —O— and/or —S—,
with the proviso that the following compound is not included

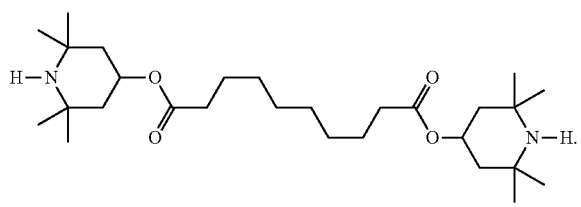

2. A compound of formula I

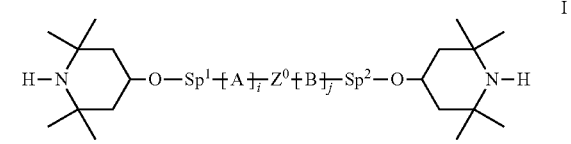

where
Sp$^1$ and Sp$^2$ are each independently alkylene having 1 to 12 carbon atoms which is optionally mono or polysubstituted by F, Cl or CN, and in which one or more nonadjacent CH$_2$ groups are optionally each independently replaced by —O—, —S—, —NH, —COO—, —OCO—, —OCO—O—, —CH═CH— or —C≡C—,
A and B are each independently:
 a) trans-1,4-cyclohexylene, 1,4-cyclohexenylene or 1,4'-bicyclohexylene, in which one or two nonadjacent CH$_2$ groups are optionally replaced by —O— and/or —S—and in which one or more hydrogen atoms are optionally replaced by F, or
 b) 1,4-phenylene or 1,3-phenylene, in which one or two nonadjacent CH groups are optionally replaced by N and in which one or more hydrogen atoms are optionally replaced by L, or
 c)

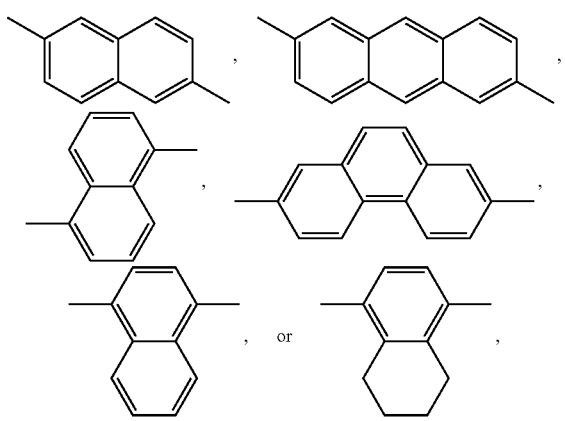

in which one or more hydrogen atoms are optionally replaced by L, and/or one or more double bonds are optionally replaced by single bonds, and/or one or more CH groups are optionally replaced by N,
i and j are each independently 0 or 1,
Z$^0$ is a single bond, —CH$_2$—, —CF$_2$—, —CO—, —O—, —NH—, —NH—(CO)—, —CH$_2$CH$_2$—, —CH═CH—, —CF$_2$O—, —OCF$_2$—, —CH$_2$O—, —OCH$_2$—, —COO—, —OCO—, —C$_2$F$_4$— or —CF═CF—,
and
L is the same or different at each instance and is F, Cl, CN or a straight-chain or branched, in each case optionally fluorinated alkyl, alkoxy, arylalkyl or alkylarylalkyl having 1 to 15 carbon atoms, in which one or more nonadjacent CH$_2$ groups are optionally replaced by —O—and/or —S—,
with the proviso that the following compound is not included

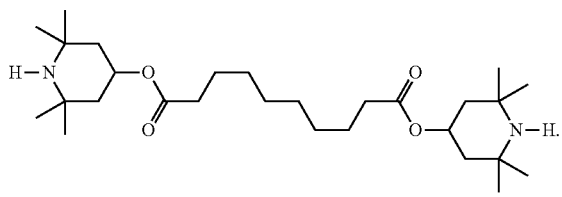

3. The compound according to claim 1 which is of formula I-A

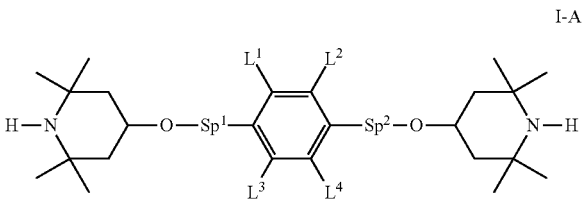

where
Sp$^1$ and Sp$^2$ are each independently a flexible linking or bridging group, which does not contain a —CO— group,
and
L$^1$ to L$^4$ are each independently H, F or straight-chain or branched, in each case optionally fluorinated alkyl having 1 to 7 carbon atoms, in which one or more nonadjacent CH$_2$ groups are optionally replaced by —O—.

4. A method for stabilization of a liquid-crystalline medium, comprising adding to said liquid-crystalline medium the compound according to claim 1.

5. A process for preparing the compound according to claim 1, comprising a reaction of 4-hydroxy-2,2,6,6-tetramethylpiperidinyloxyl.

6. A liquid-crystalline medium comprising
 a) or more compounds according to claim 1 and
 b) one or more mesogenic compounds.

7. The liquid-crystalline medium according to claim 6, wherein b) comprises one or more compounds of formulae II-1 to II-4

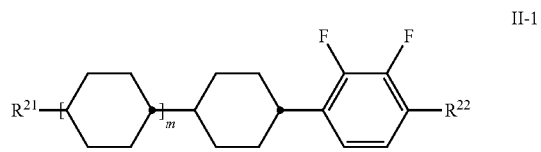

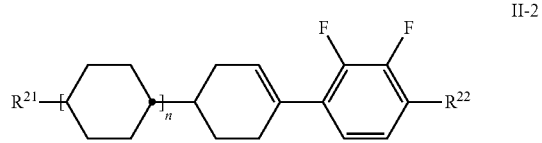

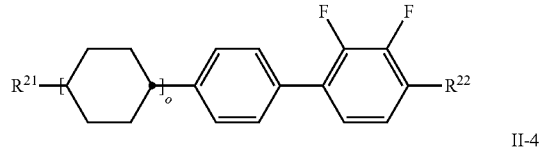

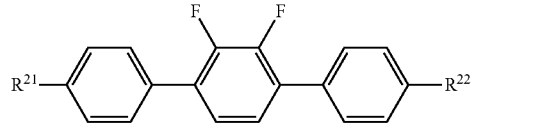

where
R$^{21}$ is an unsubstituted alkyl radical having 1 to 7 carbon atoms,
R$^{22}$ is an unsubstituted alkyl radical having 1 to 7 carbon atoms or an unsubstituted alkoxy radical having 1 to 6 carbon atoms, and m, n and o are each independently 0 or 1.

8. The liquid-crystalline medium according to claim 6, which additionally comprises one or more compounds of formula III-3 and/or formula IV

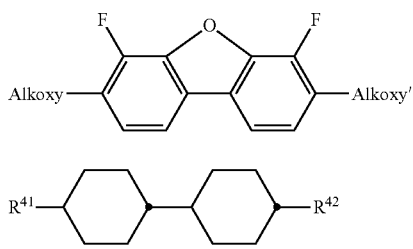

III-3

IV where

Alkoxy, Alkoxy' are independently an alkoxy radical having 1 to 5 carbon atoms, $R^{41}$ is an unsubstituted alkyl radical having 1 to 7 carbon atoms or an unsubstituted alkenyl radical having 2 to 7 carbon atoms, and $R^{42}$ is an unsubstituted alkyl radical having 1 to 7 carbon atoms, an unsubstituted alkoxy radical having 1 to 6 carbon atoms or an unsubstituted alkenyl radical having 2 to 7 carbon atoms.

9. The liquid-crystalline medium according to claim 6, wherein the total concentration of the one or more compounds of the formula I in the overall medium is 5000 ppm or less.

10. An electrooptical display or electrooptical component comprising a liquid-crystalline medium according to claim 6.

11. The compound according to claim 1, where B is trans-1,4-cyclohexylene in which one or more nonadjacent $CH_2$ groups are optionally replaced by —O— and/or —S— and in which one or more hydrogen atoms are optionally replaced by F, or 1,4-phenylene in which one or two nonadjacent CH groups are optionally replaced by N and in which one or more hydrogen atoms are optionally replaced by L.

12. The compound according to claim 1, where $Z^0$ is a single bond, —$CF_2O$— or —COO—.

13. The compound according to claim 1, where $Sp^1$ and $Sp^2$, in each case independently, are, for example, —$(CH_2)_{p1}$—, —$(CH_2CH_2O)_{q1}$—$CH_2CH_2$—, —$CH_2CH_2$—S—$CH_2CH_2$— or —$CH_2CH_2$—NH—$CH_2CH_2$—, in which p1 is an integer from 1 to 12, and q1 is an integer from 1 to 3.

14. The compound according to claim 1, which is one of the following compound of formulae I-1 to I-12:

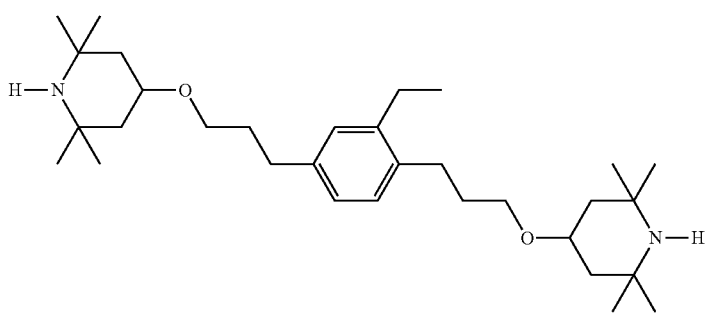

I-1

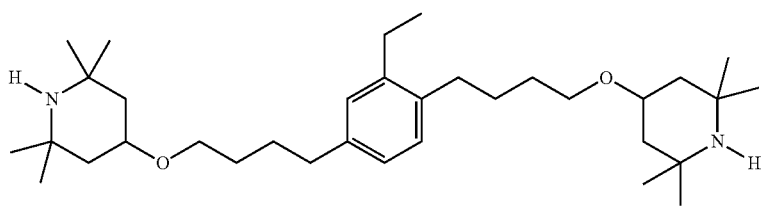

I-2

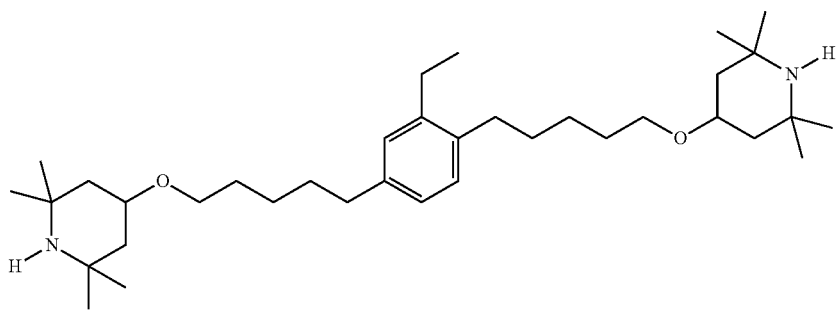

I-3

-continued
I-4
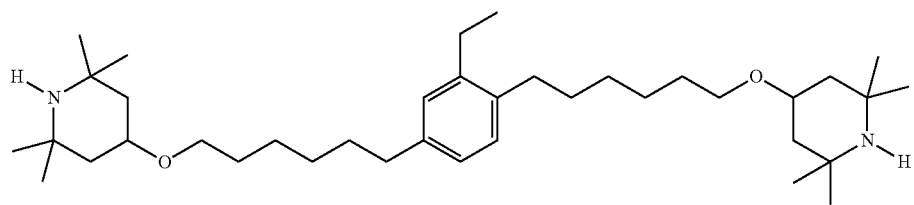
I-5
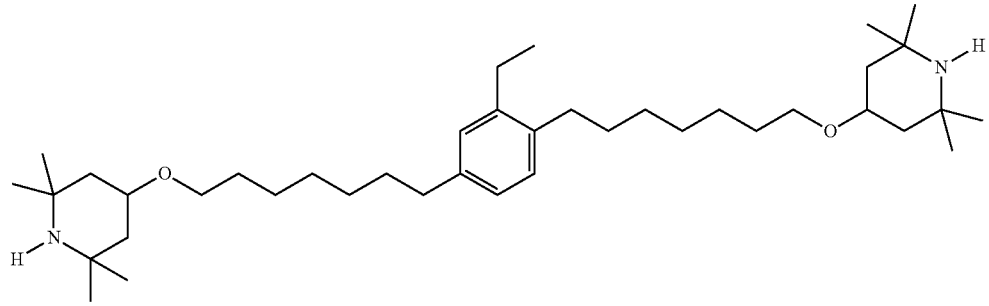
I-6
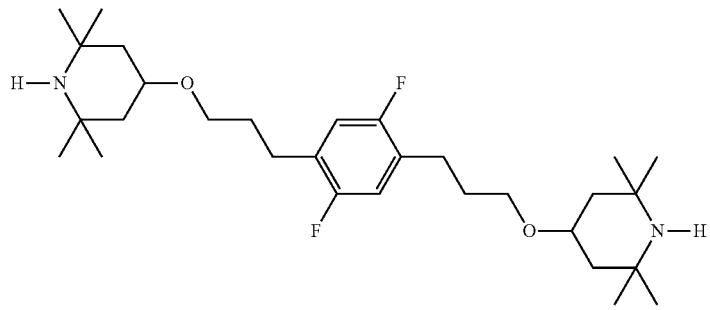
I-7
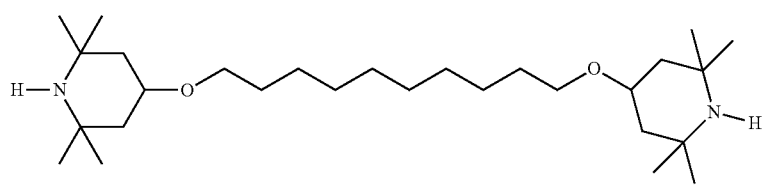
I-8
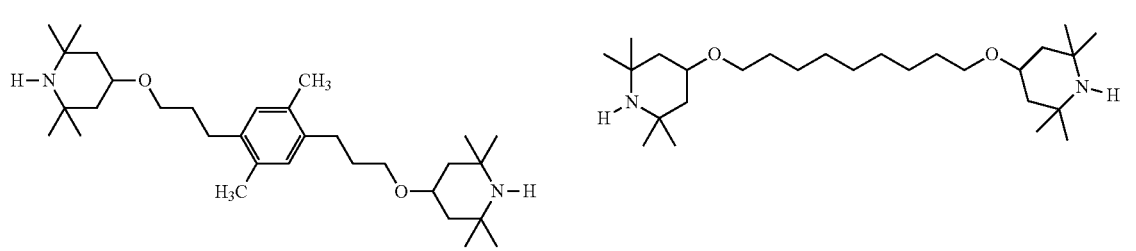
I-9
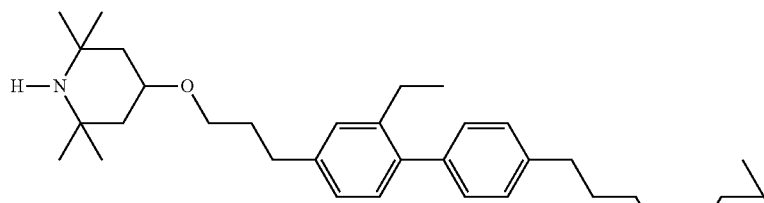
I-10
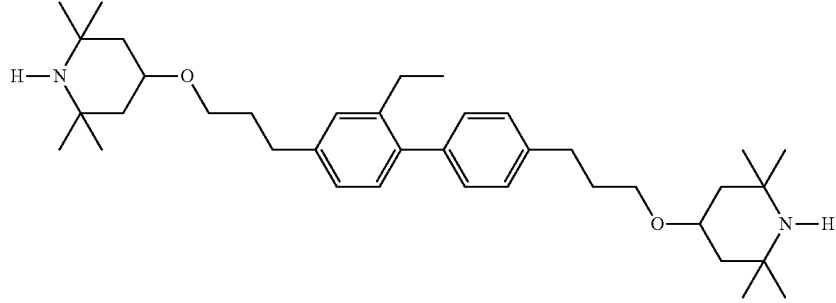

I-11

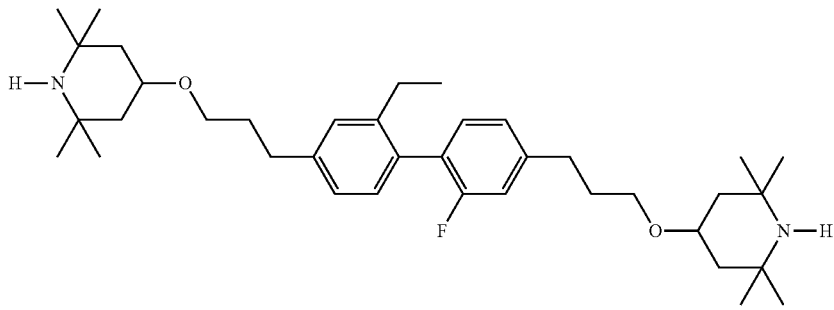

I-12

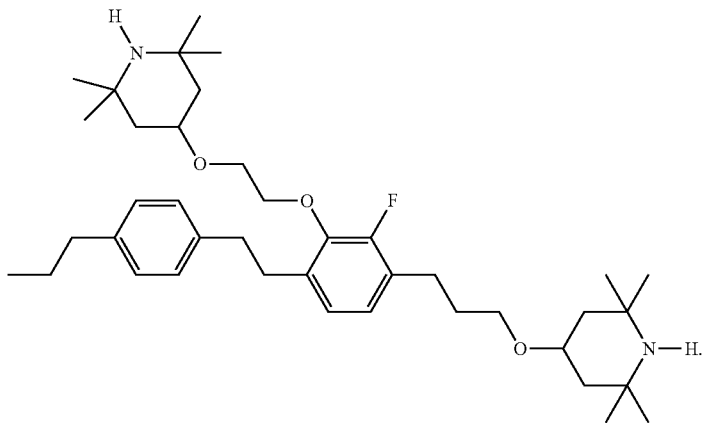

15. The compound according to claim 1, where i and j are each 0.

16. The compound according to claim 1, where i and j are each 1.

17. The compound according to claim 1, where one of i and j is 0 and the other of i and j is 1.

18. The compound according to claim 1, $Sp^1$ and $Sp^2$ are each independently alkylene having 1 to 12 carbon atoms which is optionally mono or polysubstituted by F, Cl or CN, and in which one or more nonadjacent $CH_2$ groups are optionally each independently replaced by —O—, —S—, —NH—, —CH=CH— or —C≡C—.

19. The compound according to claim 1, where the grouping $$—Sp^1—(A)_i—Z^0—(B)_j—Sp^2—$$

is not —C(O)-alkyl-C(O)—.

* * * * *